(12) United States Patent
Matsushita et al.

(10) Patent No.: US 7,342,663 B2
(45) Date of Patent: Mar. 11, 2008

(54) OPTICAL ANALYZING UNIT AND OPTICAL ANALYZING DEVICE

(75) Inventors: Tomohiko Matsushita, Hirakata (JP); Takeo Nishikawa, Kyotanabe (JP); Yuko Tsuda, Shinjuku-ku (JP); Shigemi Norioka, Ibaraki (JP); Tetsuichi Wazawa, Miyagi (JP); Shigeru Aoyama, Soraku-gun (JP)

(73) Assignee: OMRON Corporation, Kyoto-shi, Kyoto (JP)

( * ) Notice: Subject to any disclaimer, the term of this patent is extended or adjusted under 35 U.S.C. 154(b) by 0 days.

(21) Appl. No.: 10/582,188

(22) PCT Filed: Dec. 8, 2004

(86) PCT No.: PCT/JP2004/018315

§ 371 (c)(1),
(2), (4) Date: Feb. 2, 2007

(87) PCT Pub. No.: WO2005/054826

PCT Pub. Date: Jun. 16, 2005

(65) Prior Publication Data
US 2007/0211254 A1    Sep. 13, 2007

(30) Foreign Application Priority Data
Dec. 8, 2003   (JP)   ............................. 2003-409456

(51) Int. Cl.
*G01N 21/55* (2006.01)
(52) U.S. Cl. .................................................. 356/445
(58) Field of Classification Search ................ None
See application file for complete search history.

(56) References Cited

U.S. PATENT DOCUMENTS

| | | | |
|---|---|---|---|
| 6,432,364 B1 * | 8/2002 | Negami et al. | 422/82.11 |
| 6,529,277 B1 * | 3/2003 | Weitekamp | 356/445 |
| 6,956,651 B2 * | 10/2005 | Lackritz et al. | 356/445 |

FOREIGN PATENT DOCUMENTS

JP    9-033427    2/1997

(Continued)

OTHER PUBLICATIONS

Patent Abstracts of Japan; Publication number: 2000-131237; date of publication: May 12, 2000 (2 pages).

(Continued)

*Primary Examiner*—Tu T Nguyen
(74) *Attorney, Agent, or Firm*—Osha • Liang LLP

(57) ABSTRACT

At both ends of a waveguide 43 having a plurality of cores 51, light emitting elements 47 and light receiving elements 49 are disposed so as to face end faces of the cores 51. A switch 44 is overlapped over the waveguide 43. In the switch 44, switching windows 52 each can be switched between a state where light propagating through the core 51 is passed and a state where the light is reflected are arranged in the vertical and horizontal directions, and the switching windows 52 are arranged along the top faces of the cores 51. A test board 45 having a plurality of channels 60 in each of which a metallic thin film 61 is formed is disposed over the switch 44, and receptors 62 are fixed on the metallic thin film 61 in the channels 60. A specimen containing a specific ligand is passed in each of the channels 60.

14 Claims, 48 Drawing Sheets

FOREIGN PATENT DOCUMENTS

| | | |
|---|---|---|
| JP | 2000-131237 | 5/2000 |
| JP | 2001-255267 | 9/2001 |
| JP | 2002-162346 | 6/2002 |
| JP | 2003-065945 | 3/2003 |
| JP | 2003-287493 | 10/2003 |

OTHER PUBLICATIONS

Patent Abstracts of Japan; Publication number: 2001-255267; Date of publication: Sep. 21, 2001 (2 pages).
Patent Abstracts of Japan; Publication number: 2002-162346; Date of publication: Jun. 07, 2002 (2 pages).
International Search Report for PCT/JP2004/018315 dated Mar. 1, 2005 (2 pages).
Patent Abstracts of Japan 2002-162346 dated Jun. 7, 2002 (2 pages).
Patent Abstracts of Japan 2003-065945 dated Mar. 5, 2003 (2 pages).
Patent Abstracts of Japan 09-033427 dated Feb. 7, 1997 (2 pages).
Patent Abstracts of Japan 2003-287493 dated Oct. 10, 2003 (2 pages).

\* cited by examiner

[Fig. 1] (Prior Art)
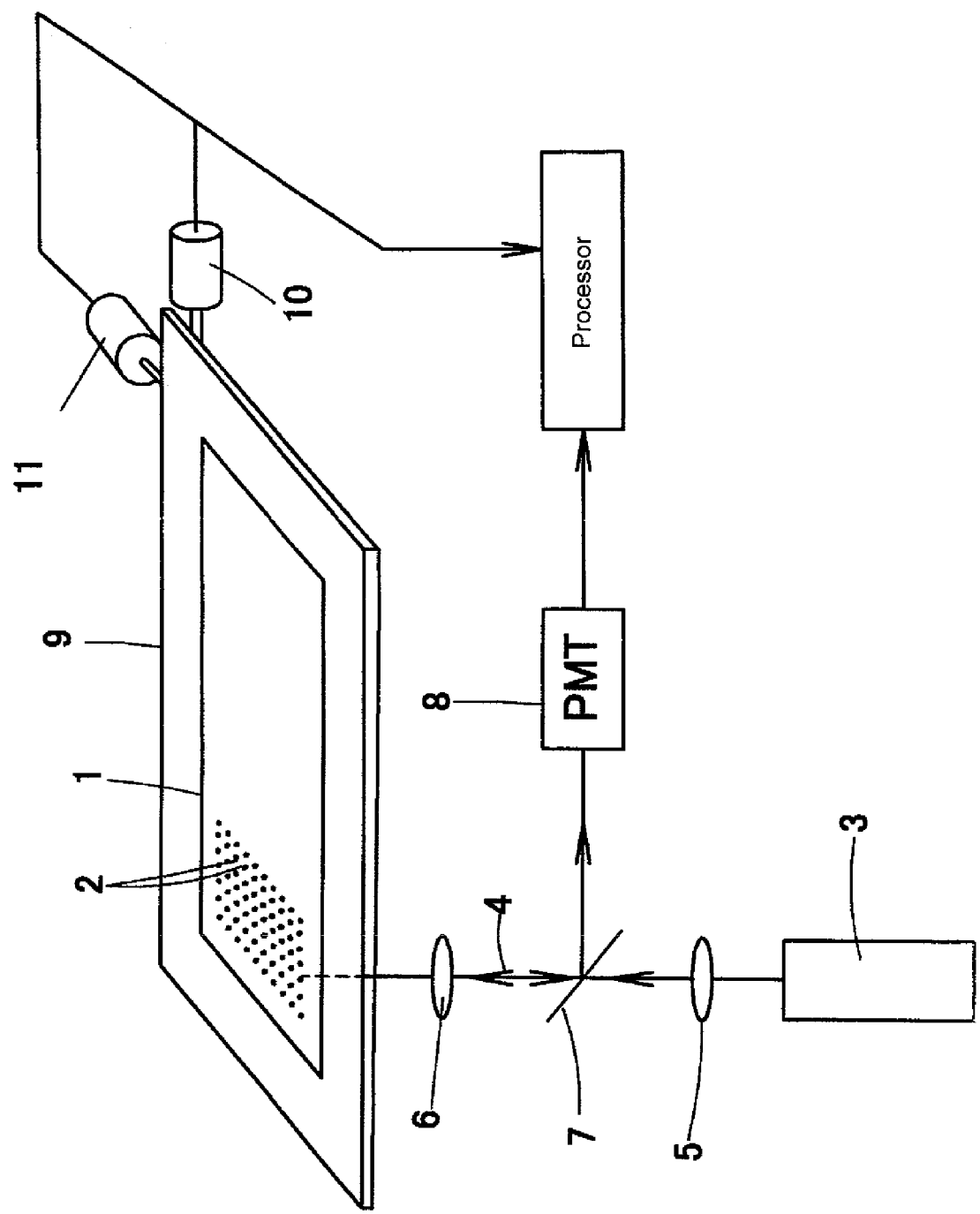

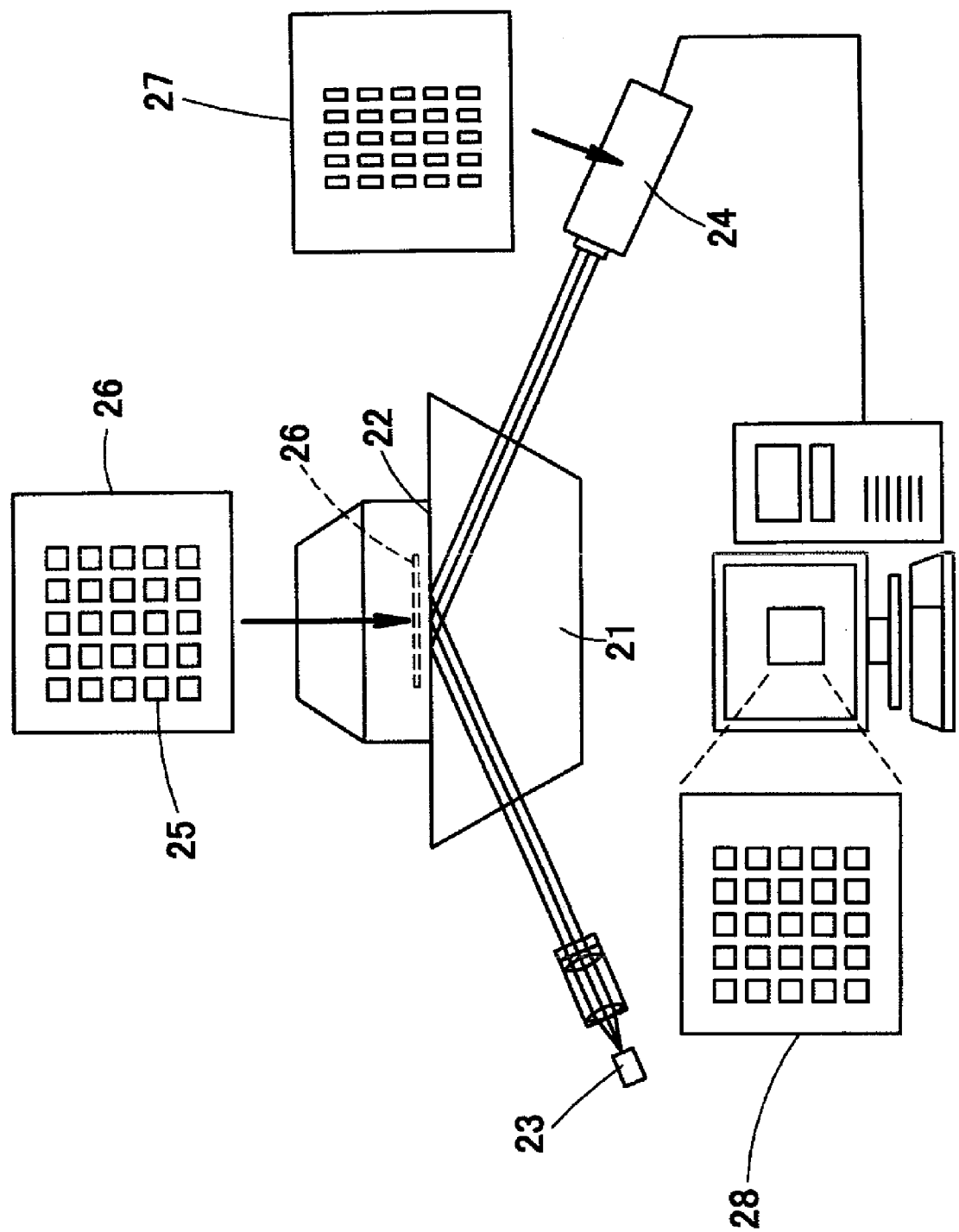
[Fig. 2] (Prior Art)

[Fig. 3] (Prior Art)
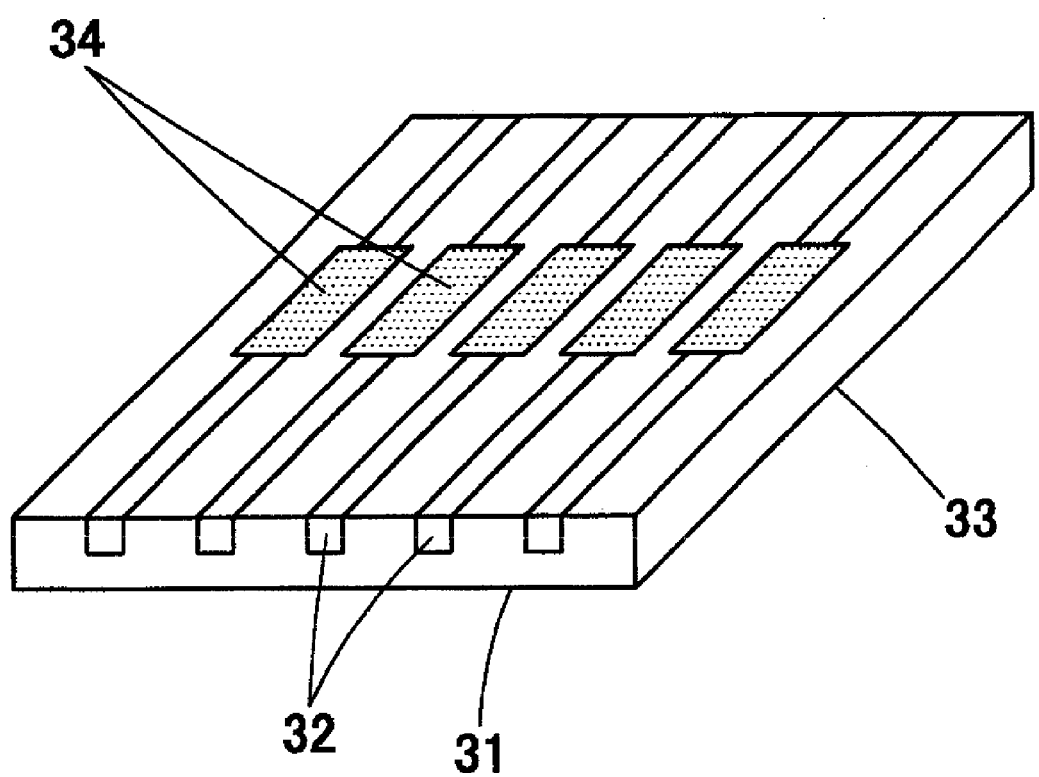

[Fig. 4]
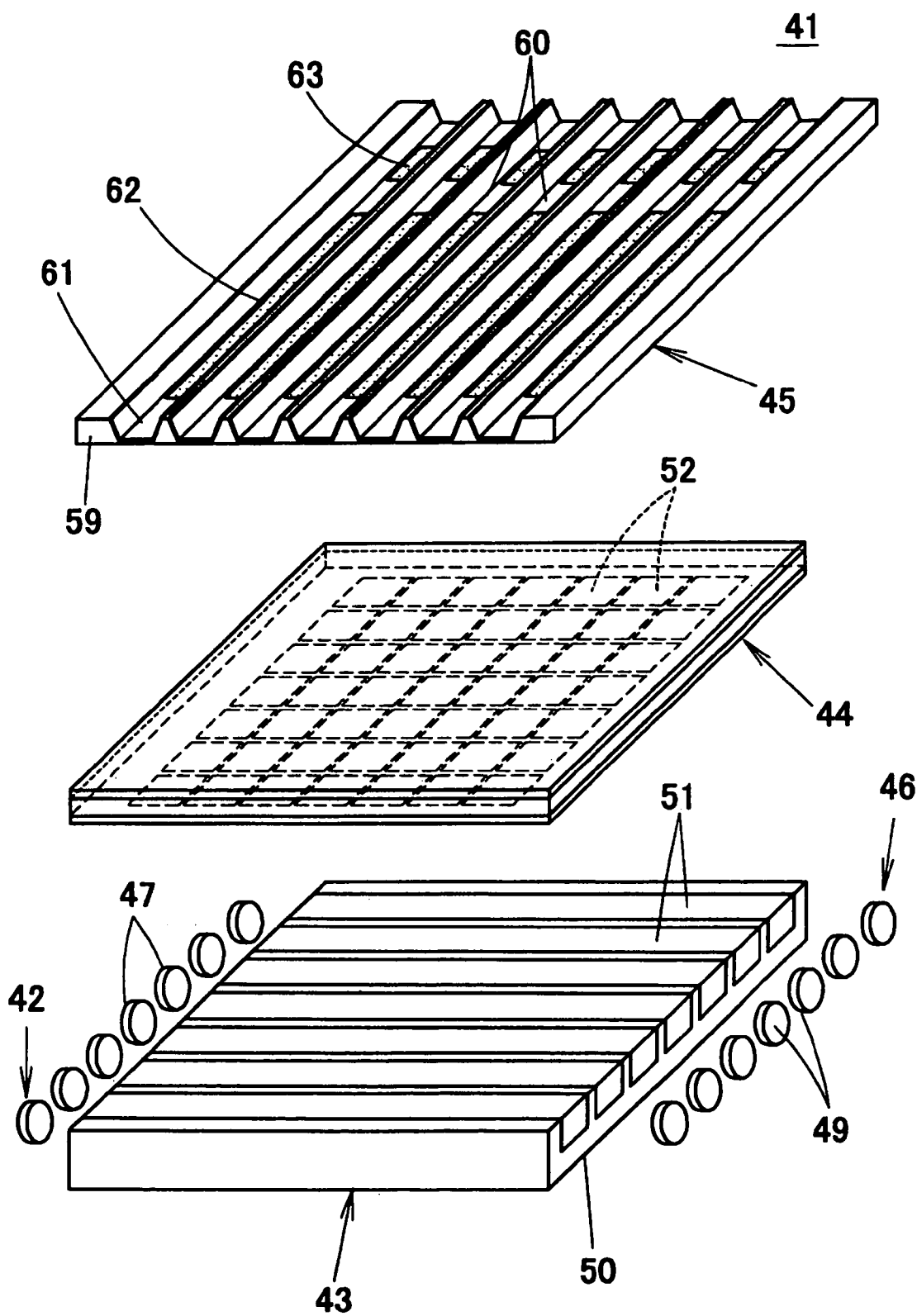

[Fig. 5]
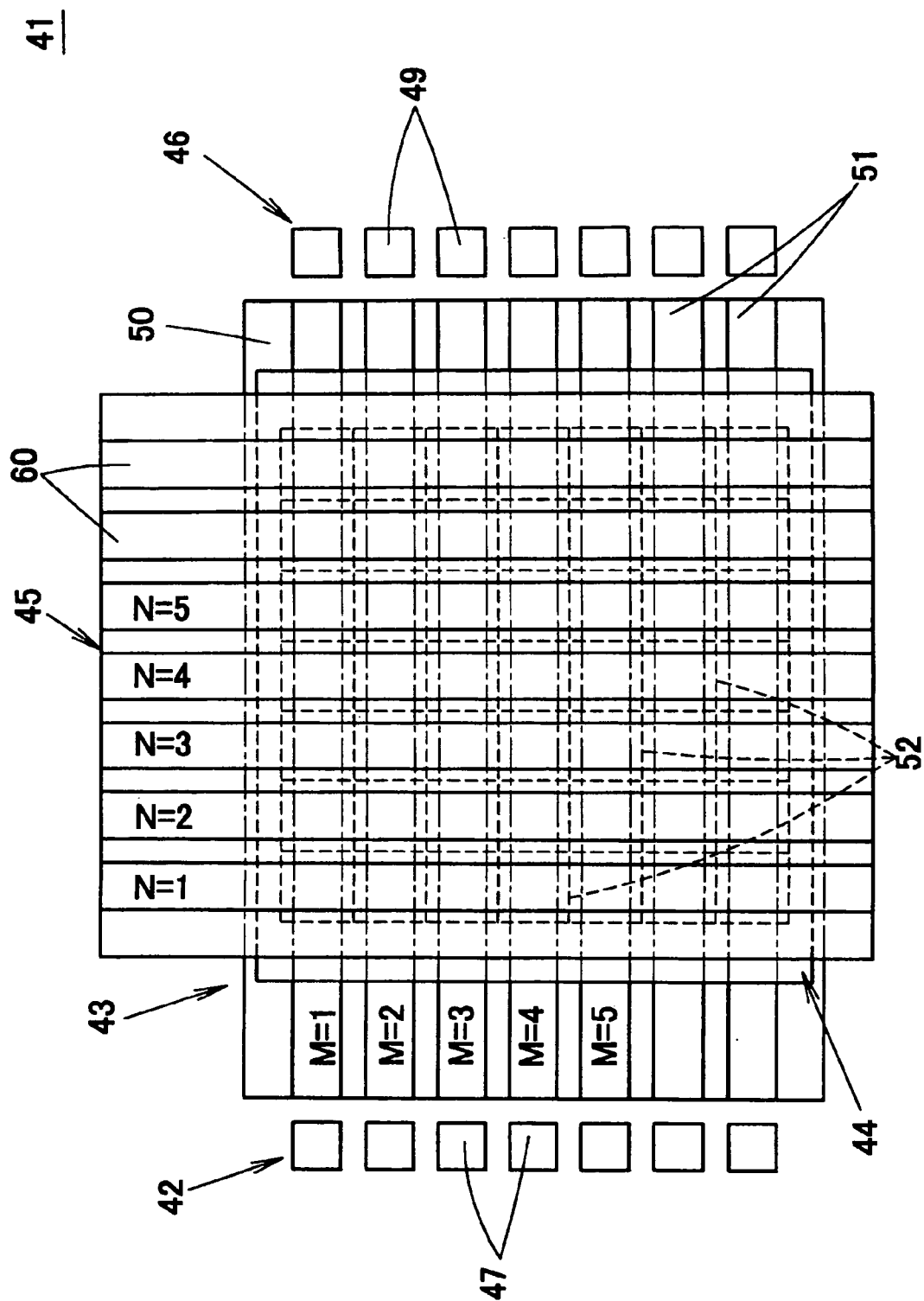

[Fig. 6]
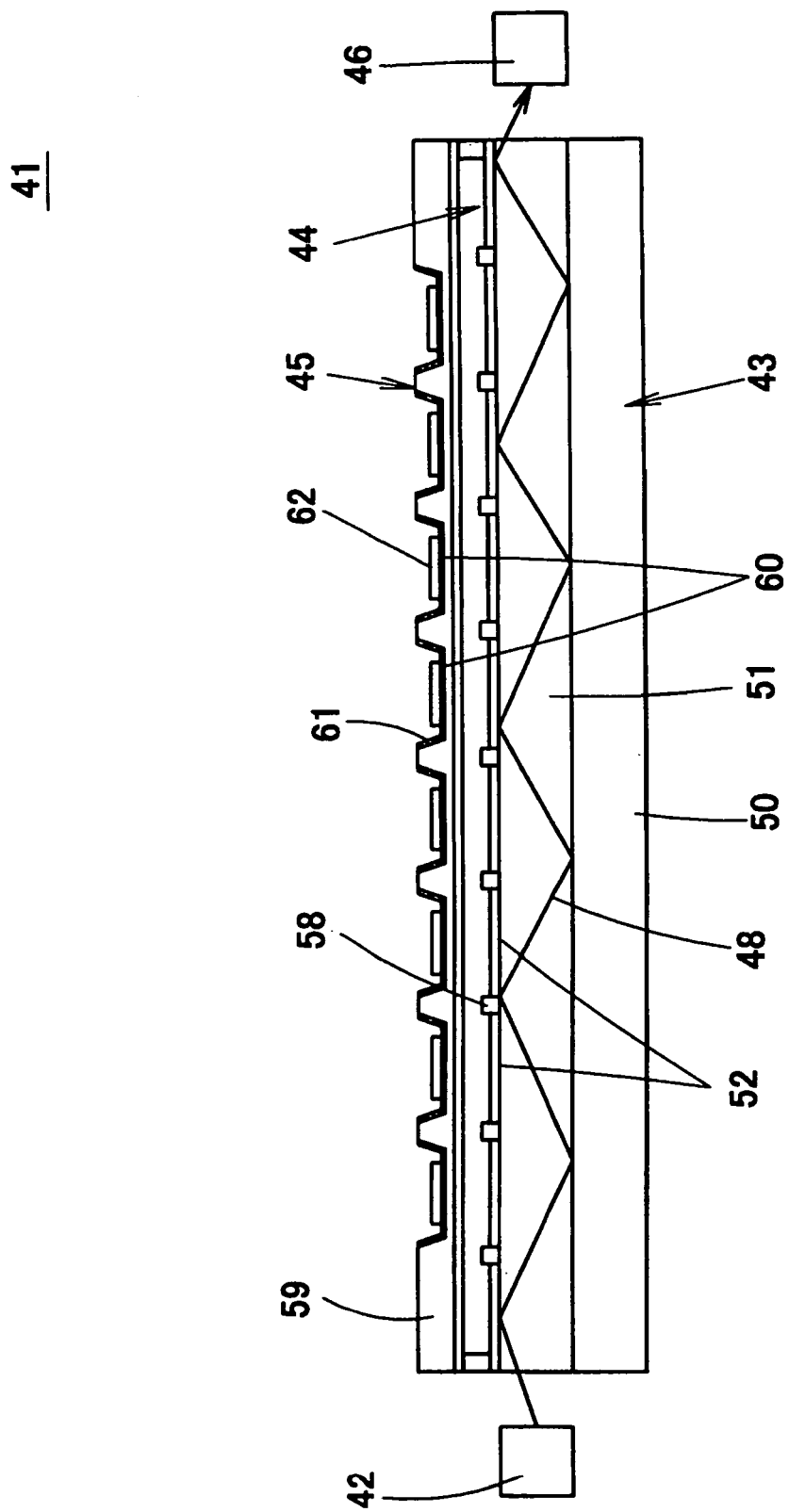

[Fig. 7]
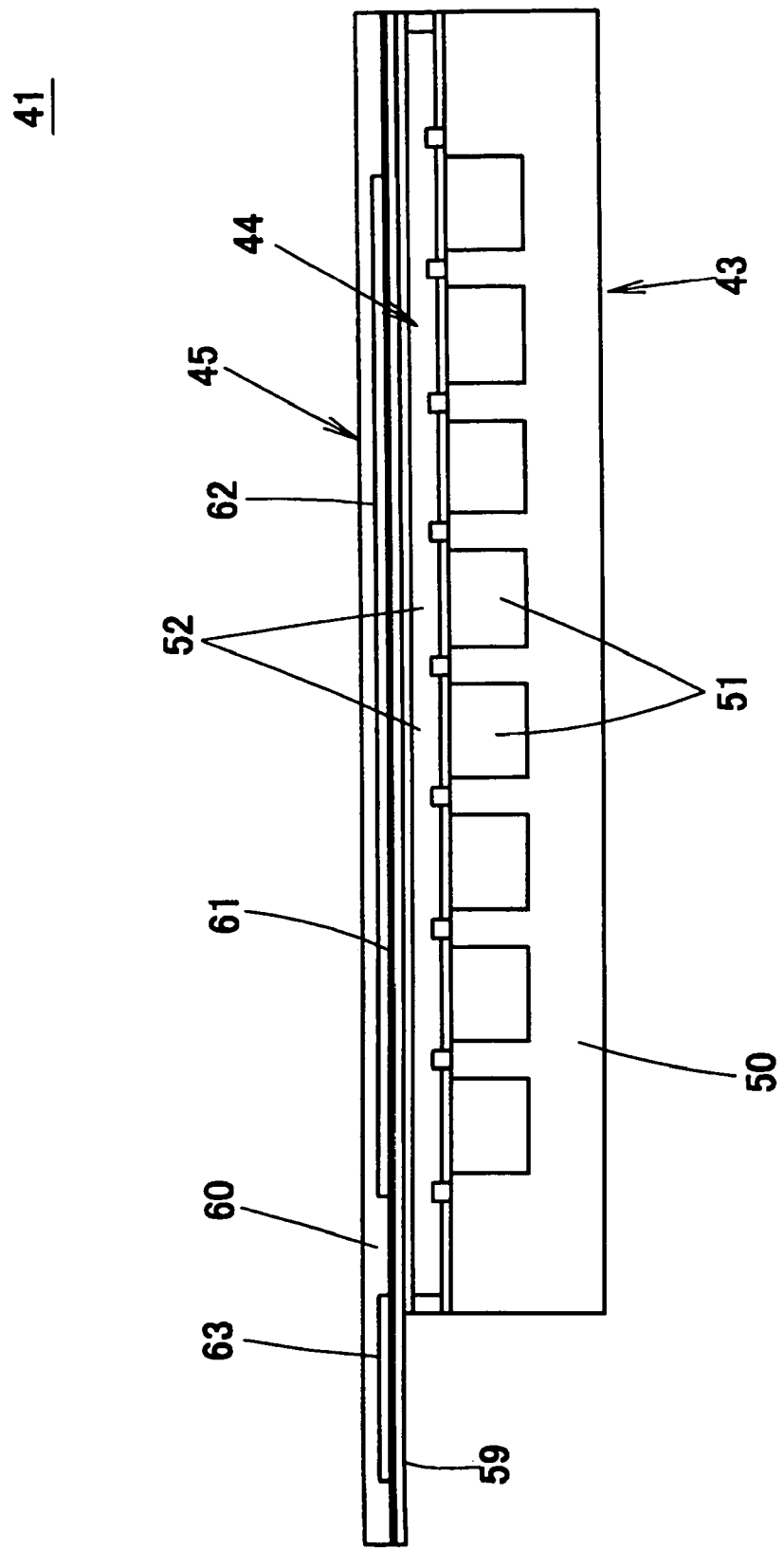

[Fig. 8]
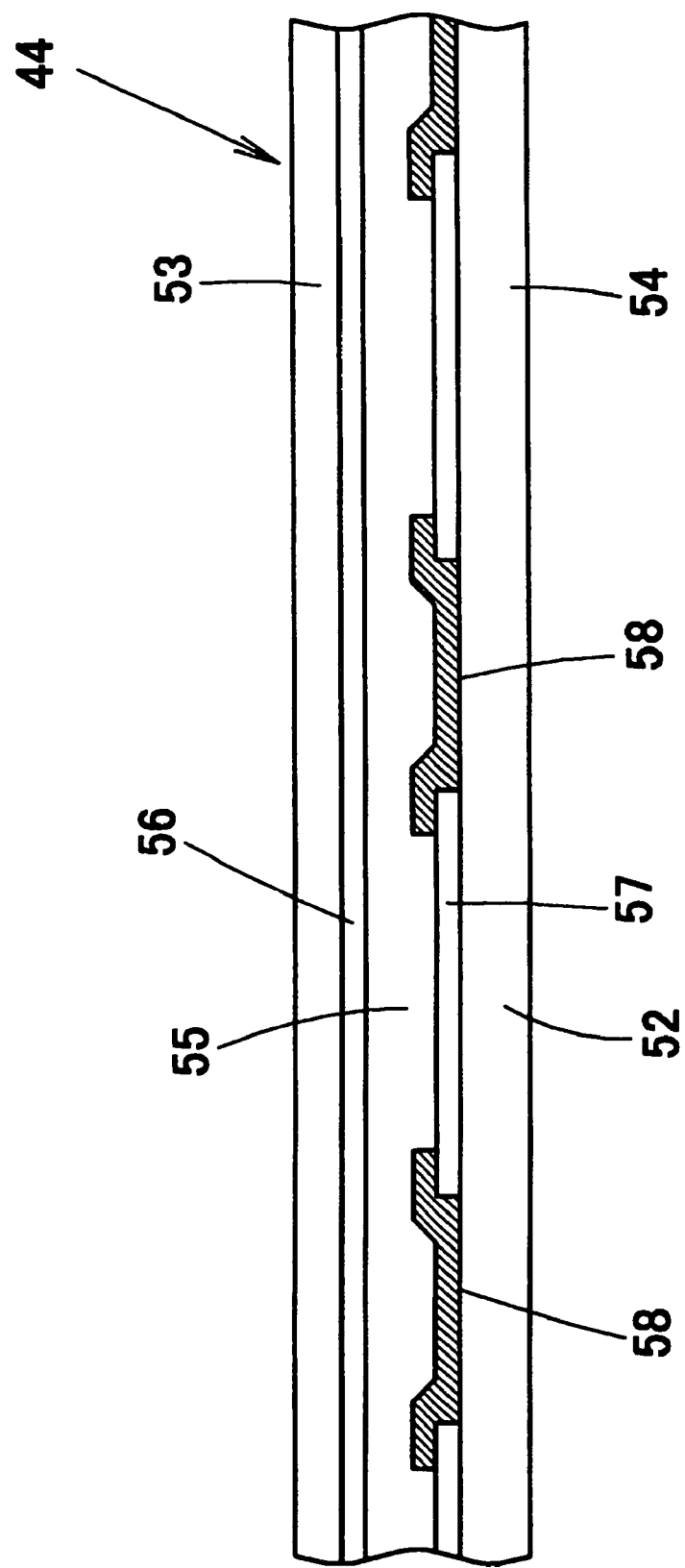

[Fig. 9]
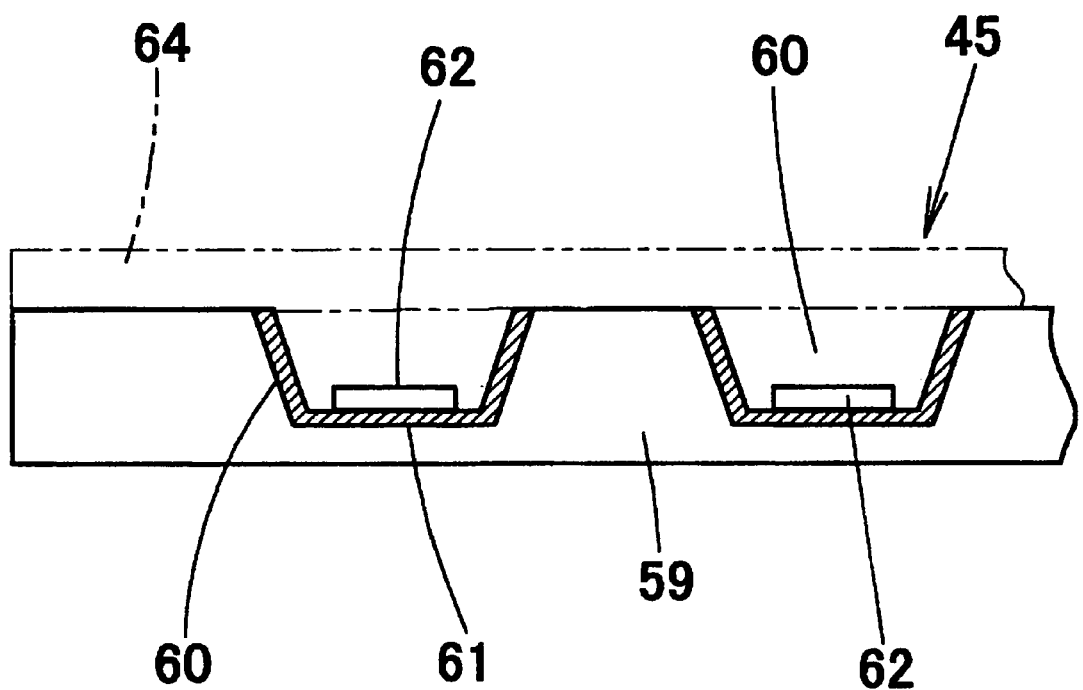

[Fig. 10]
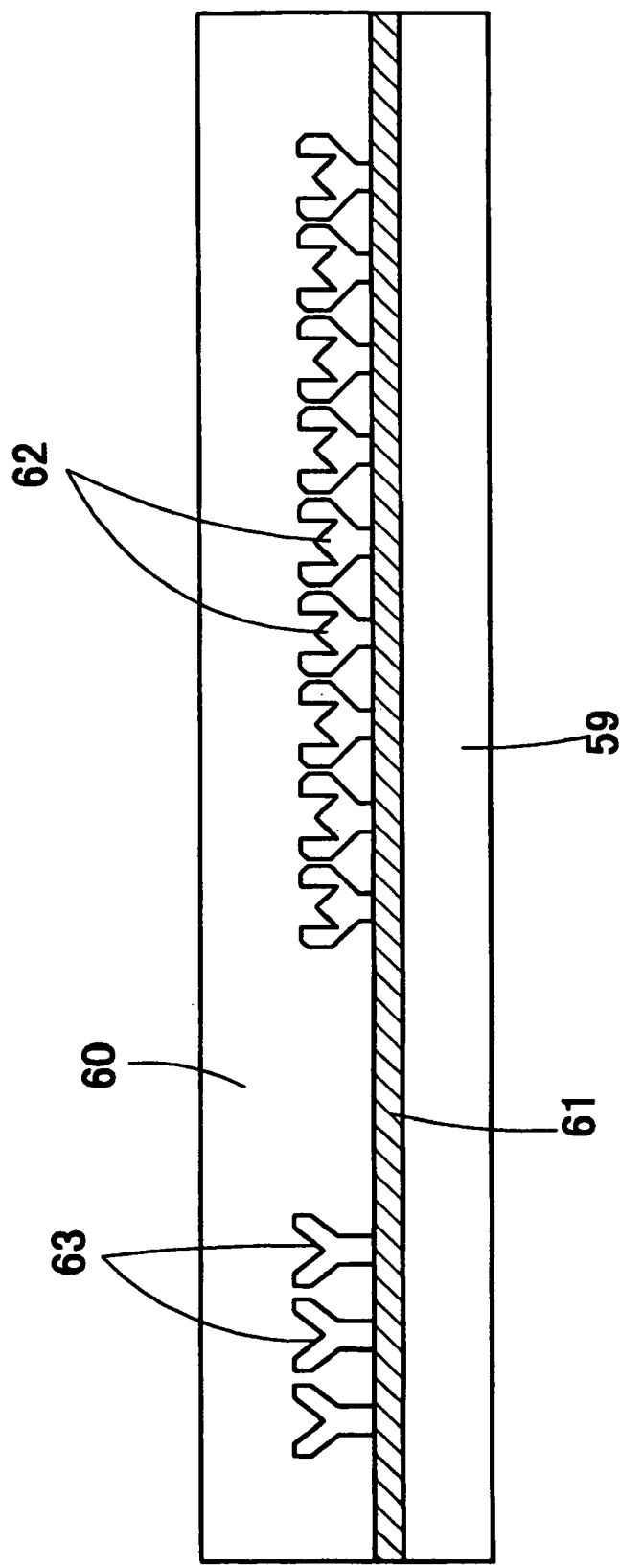

[Fig. 11]
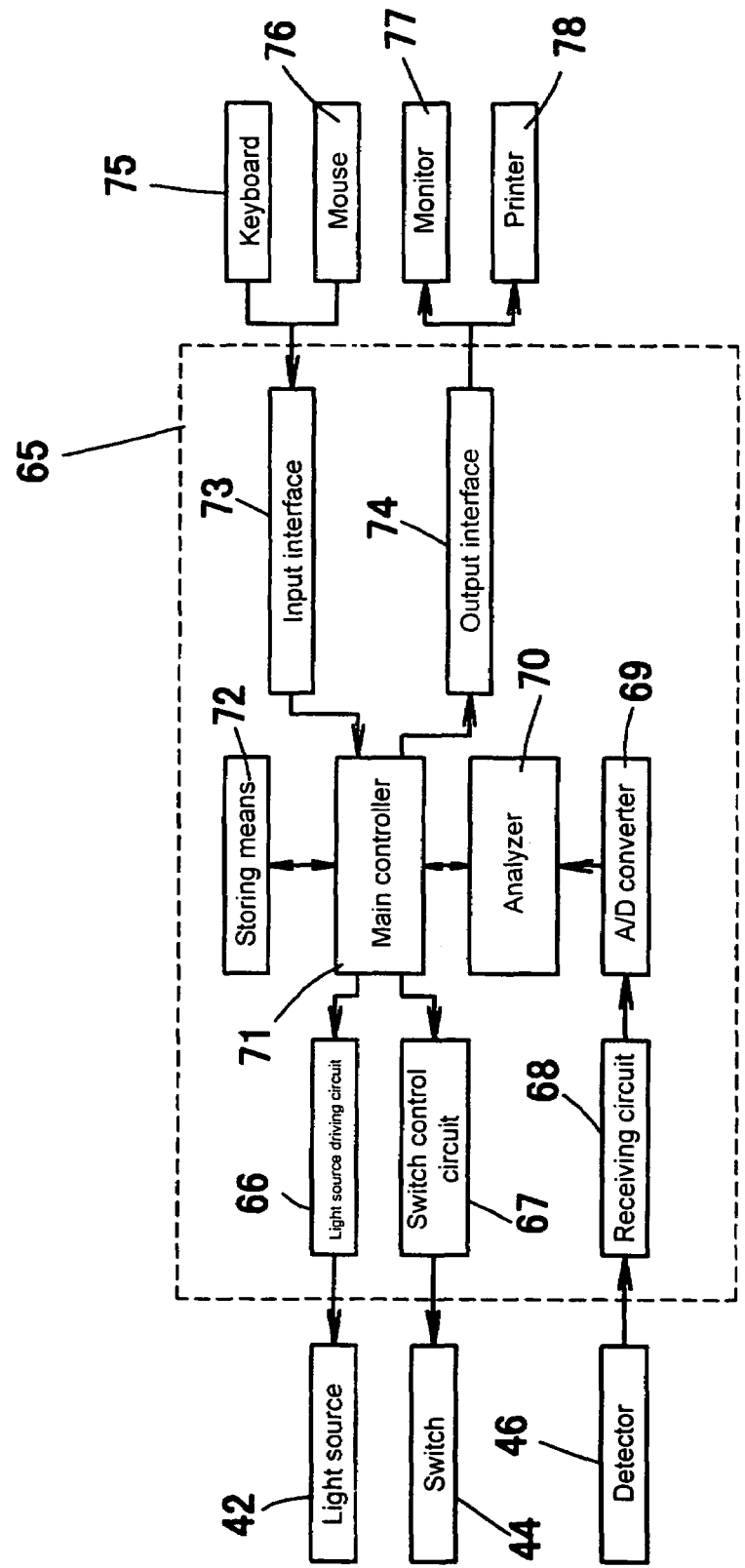

[Fig. 12]
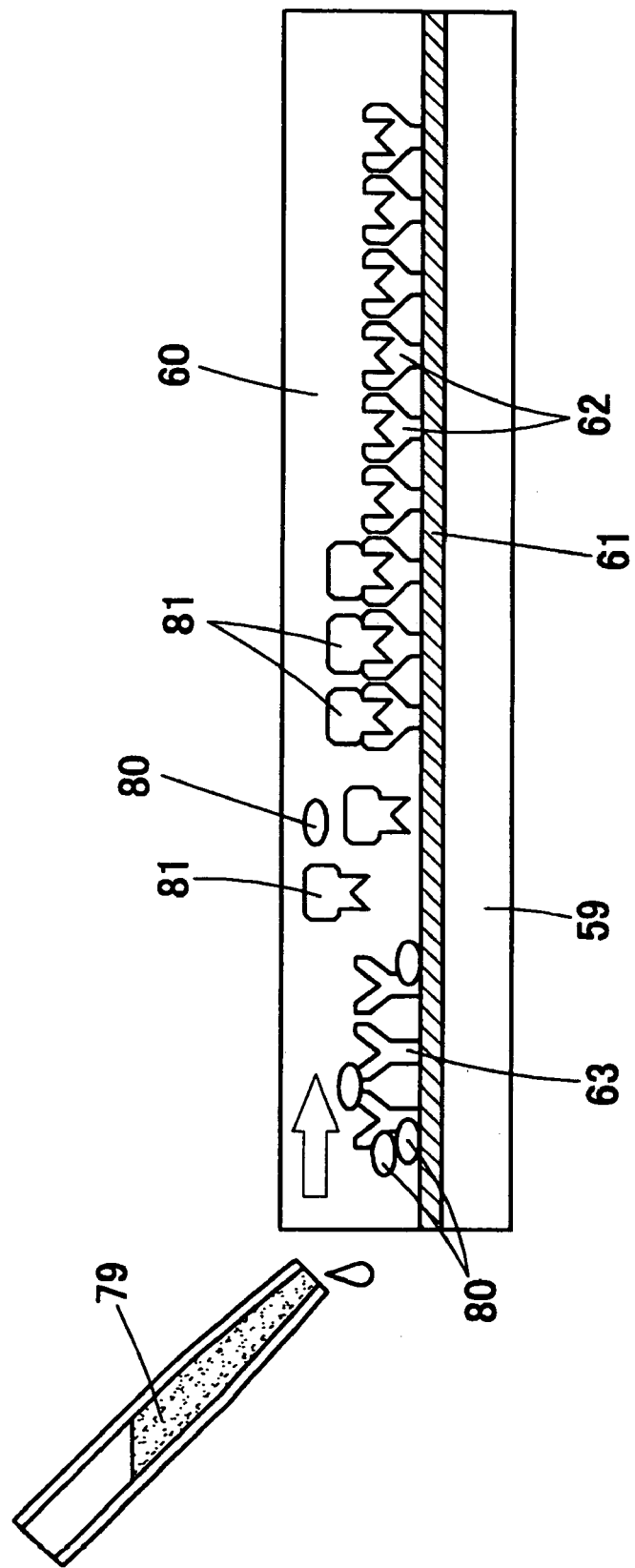

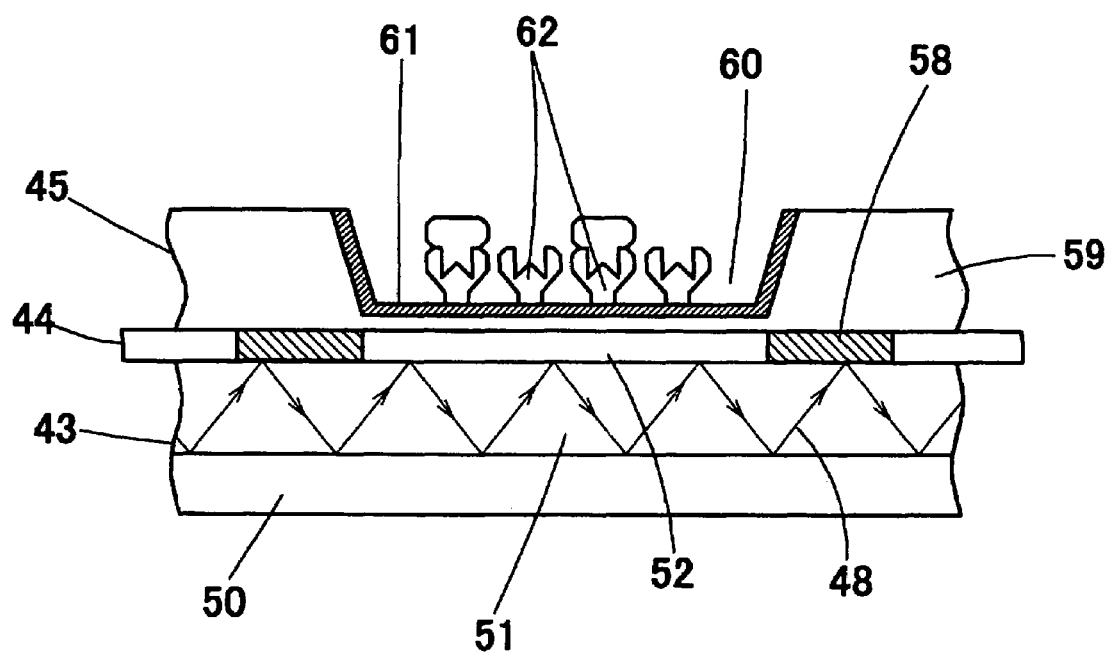
[Fig. 13]

[Fig. 14]
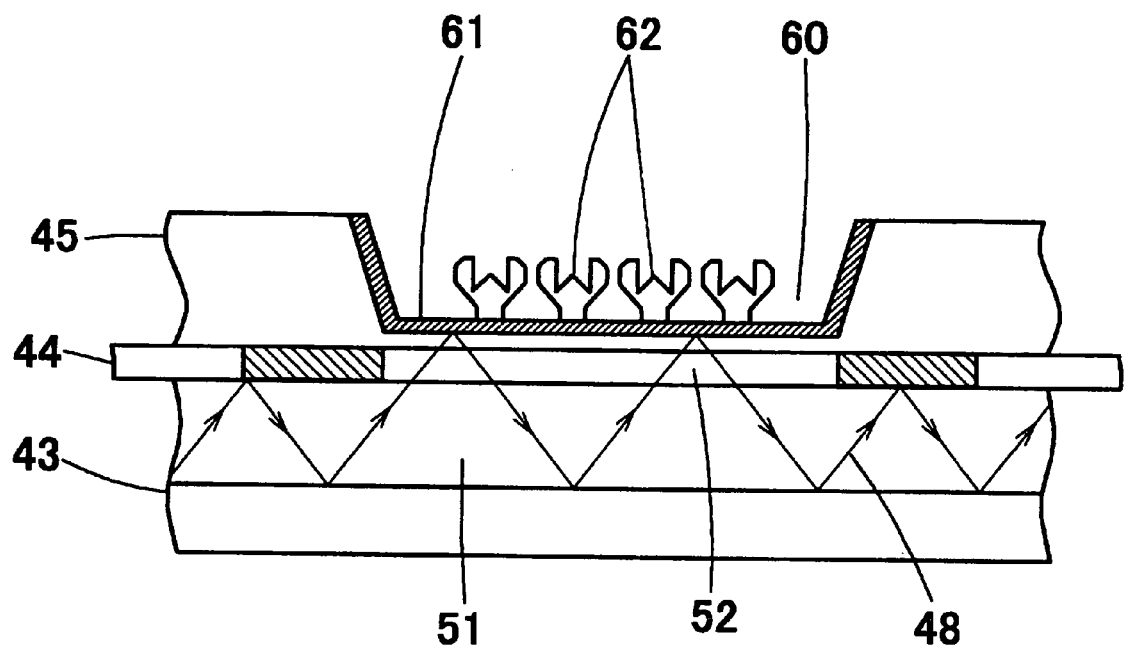

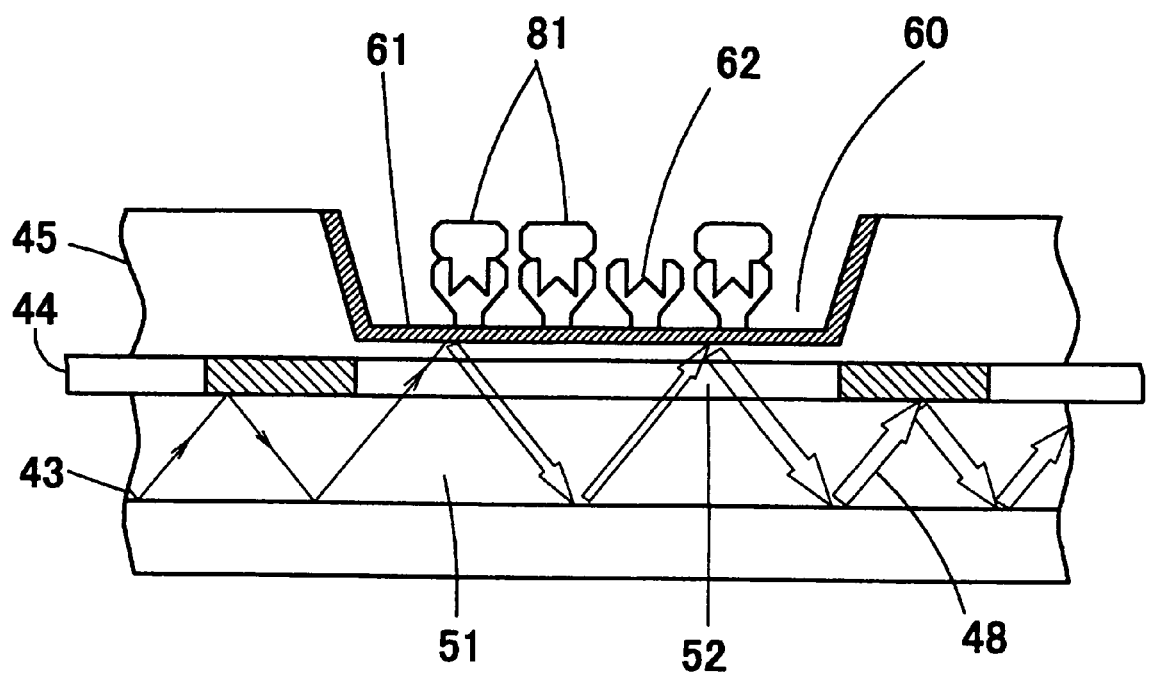
[Fig. 15]

[Fig. 16]
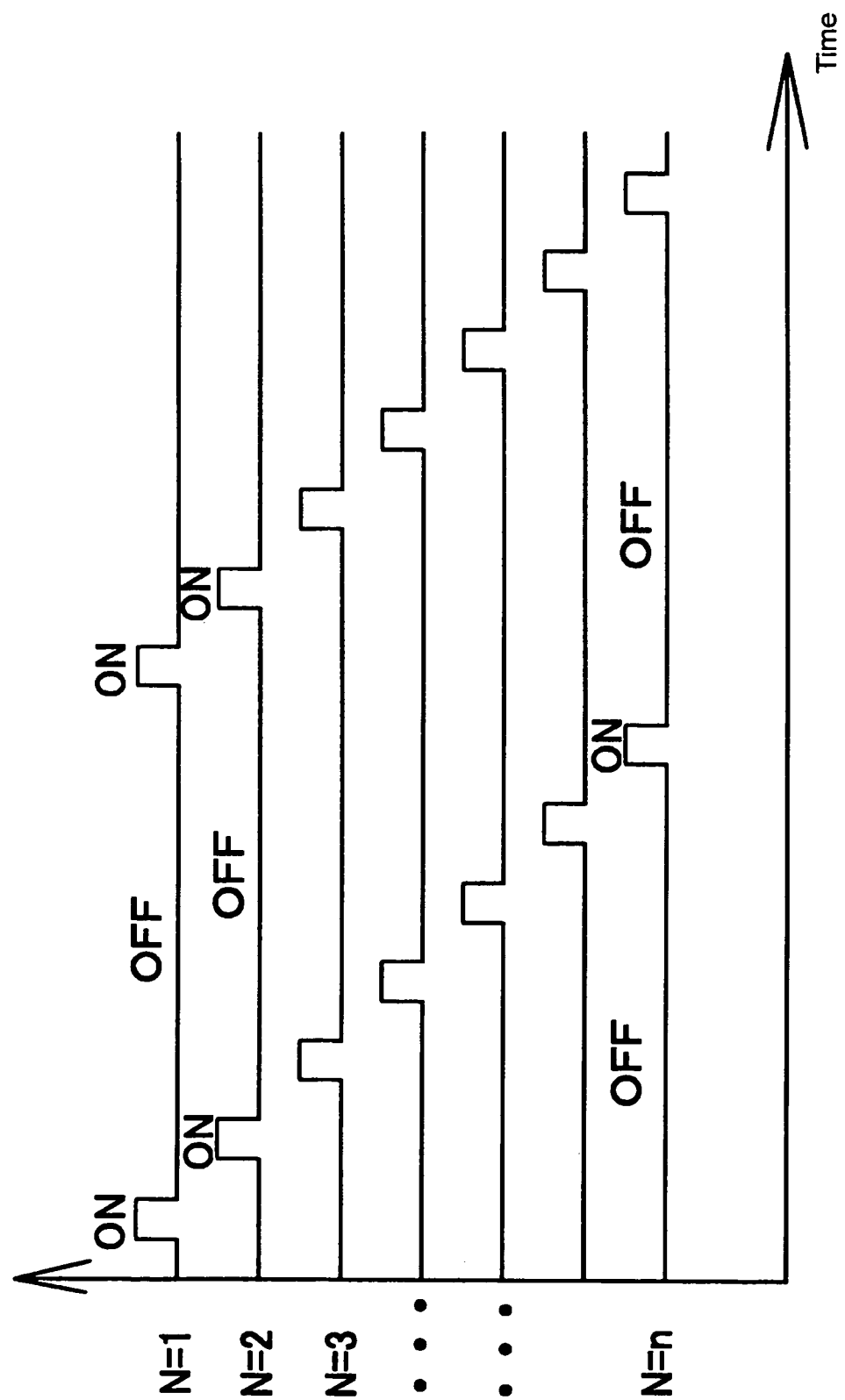

[Fig. 17]
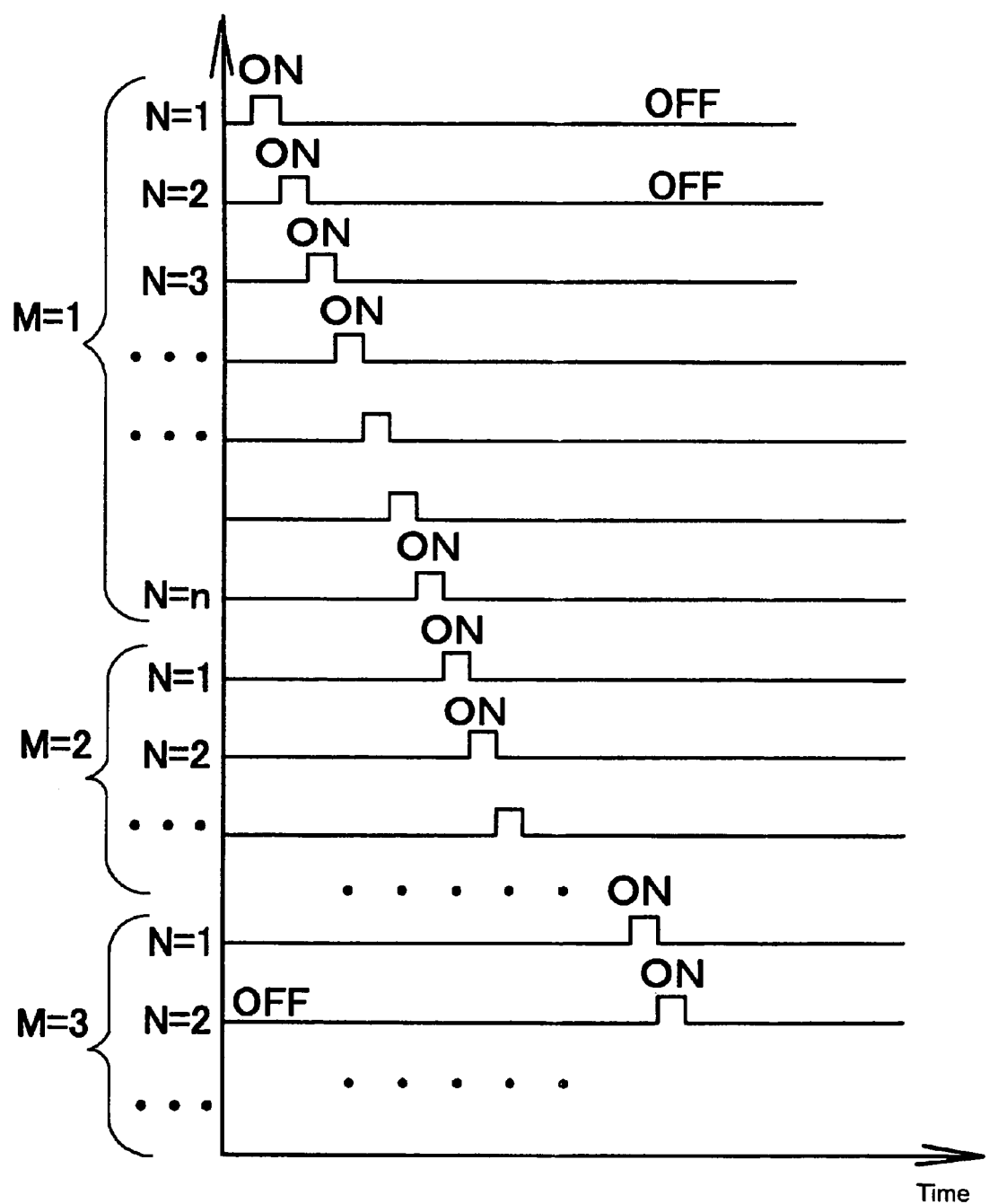

[Fig. 18]
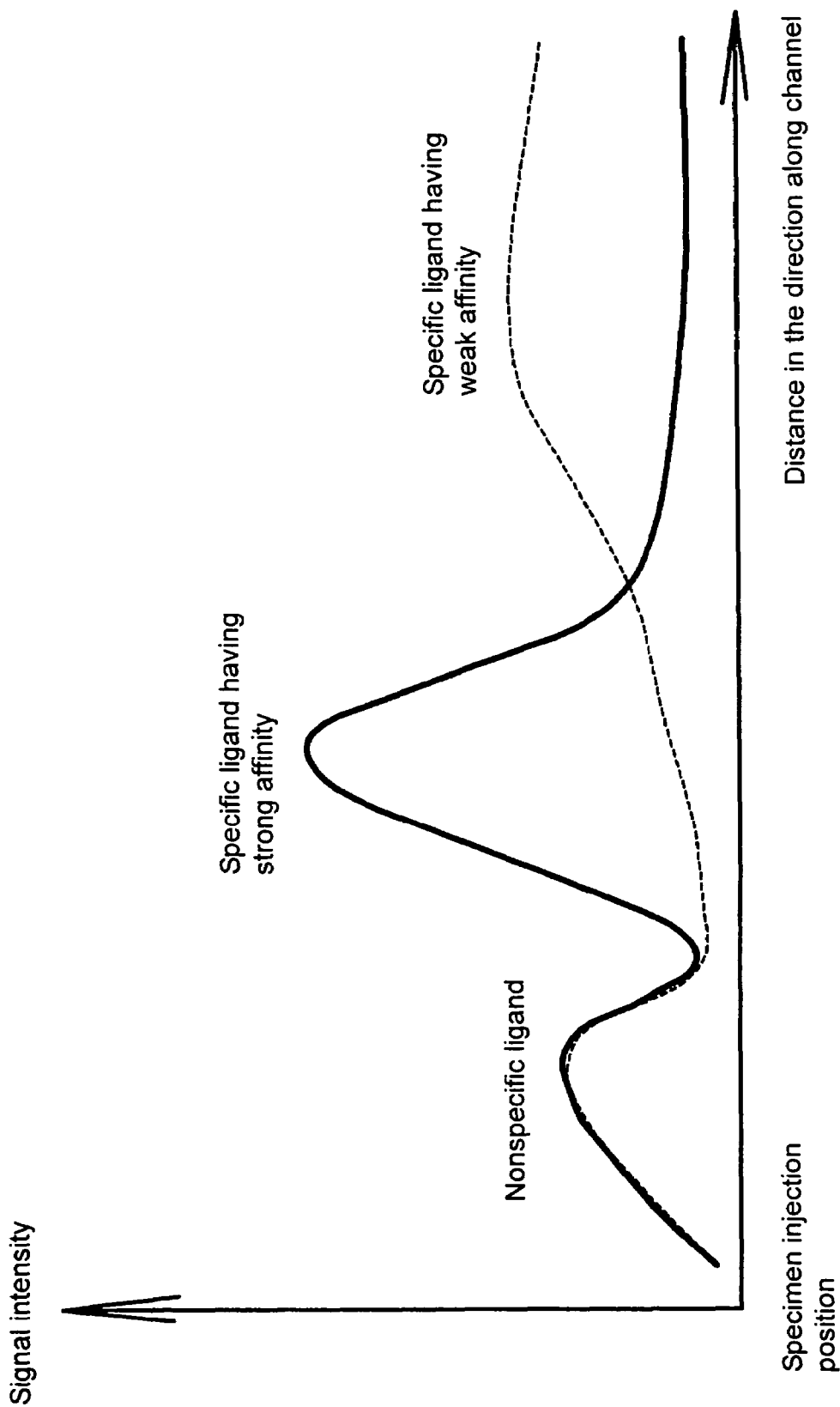

[Fig. 19]
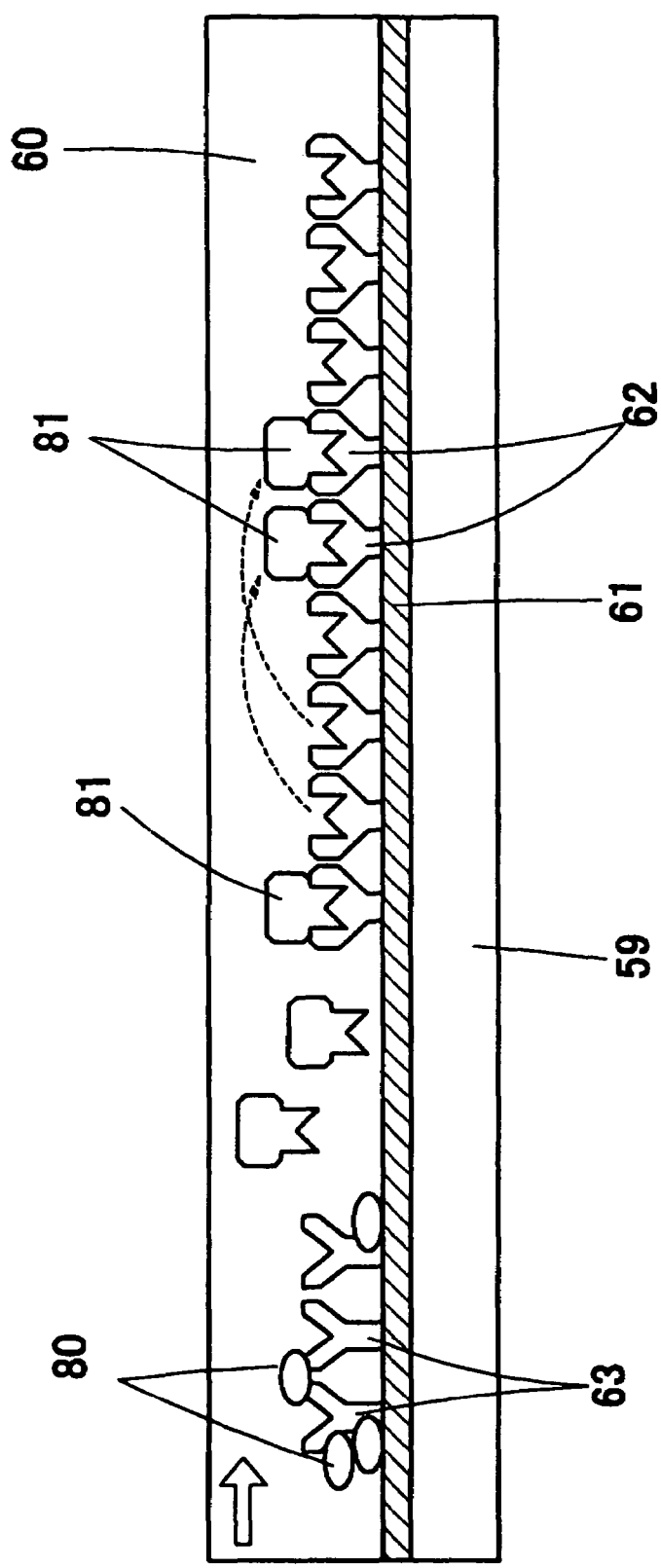

[Fig. 20]
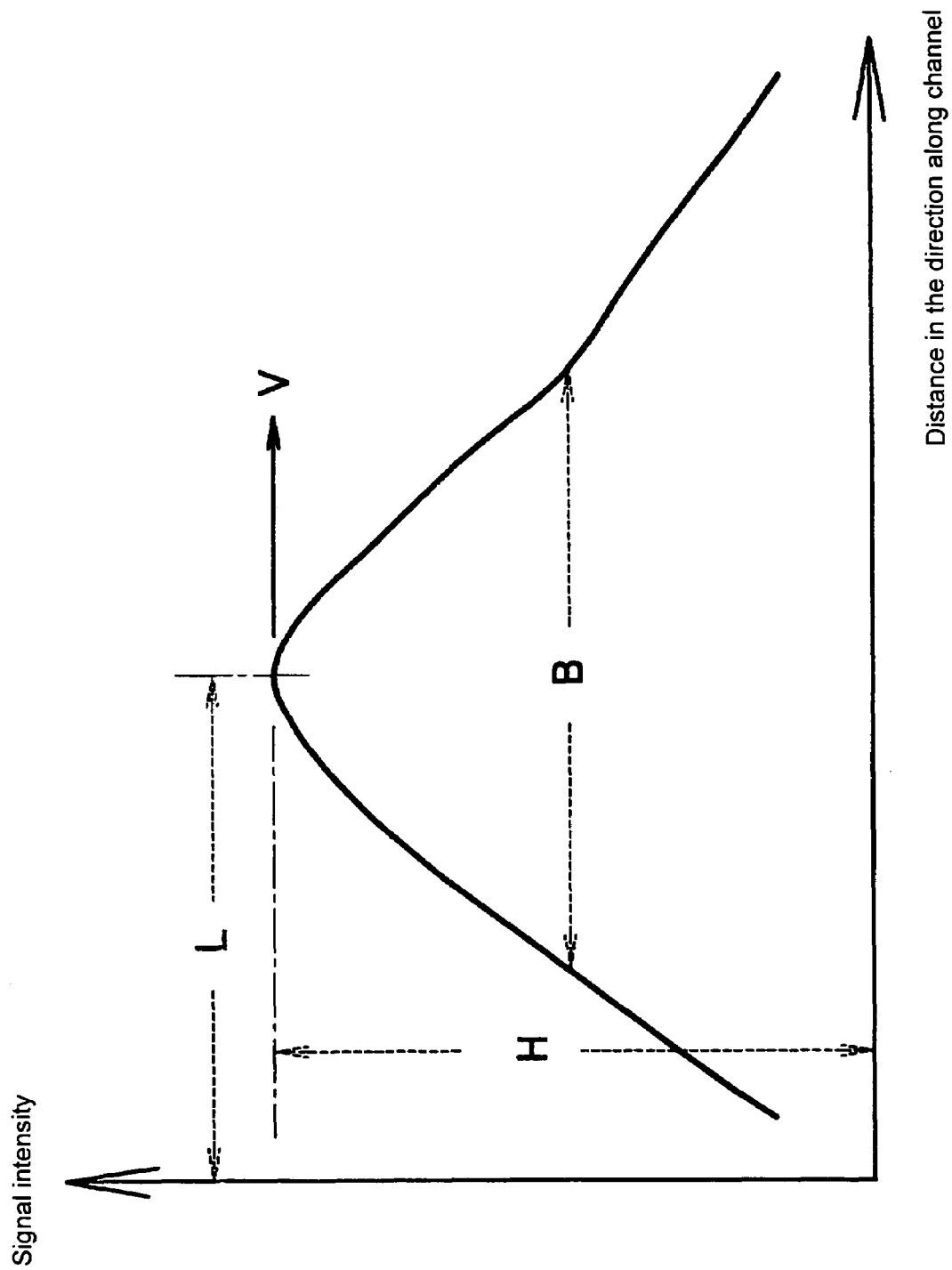

[Fig. 21]
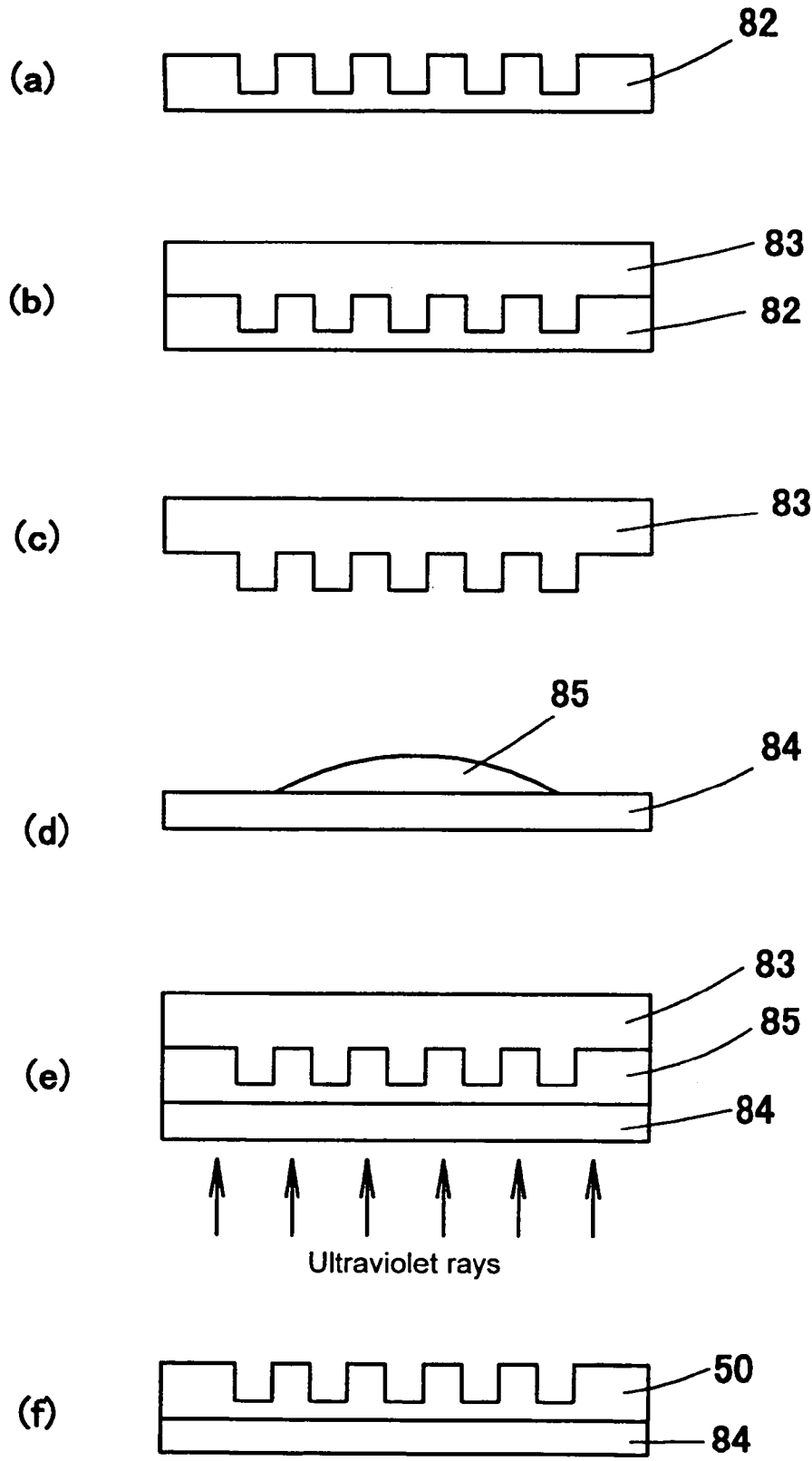

[Fig. 22]
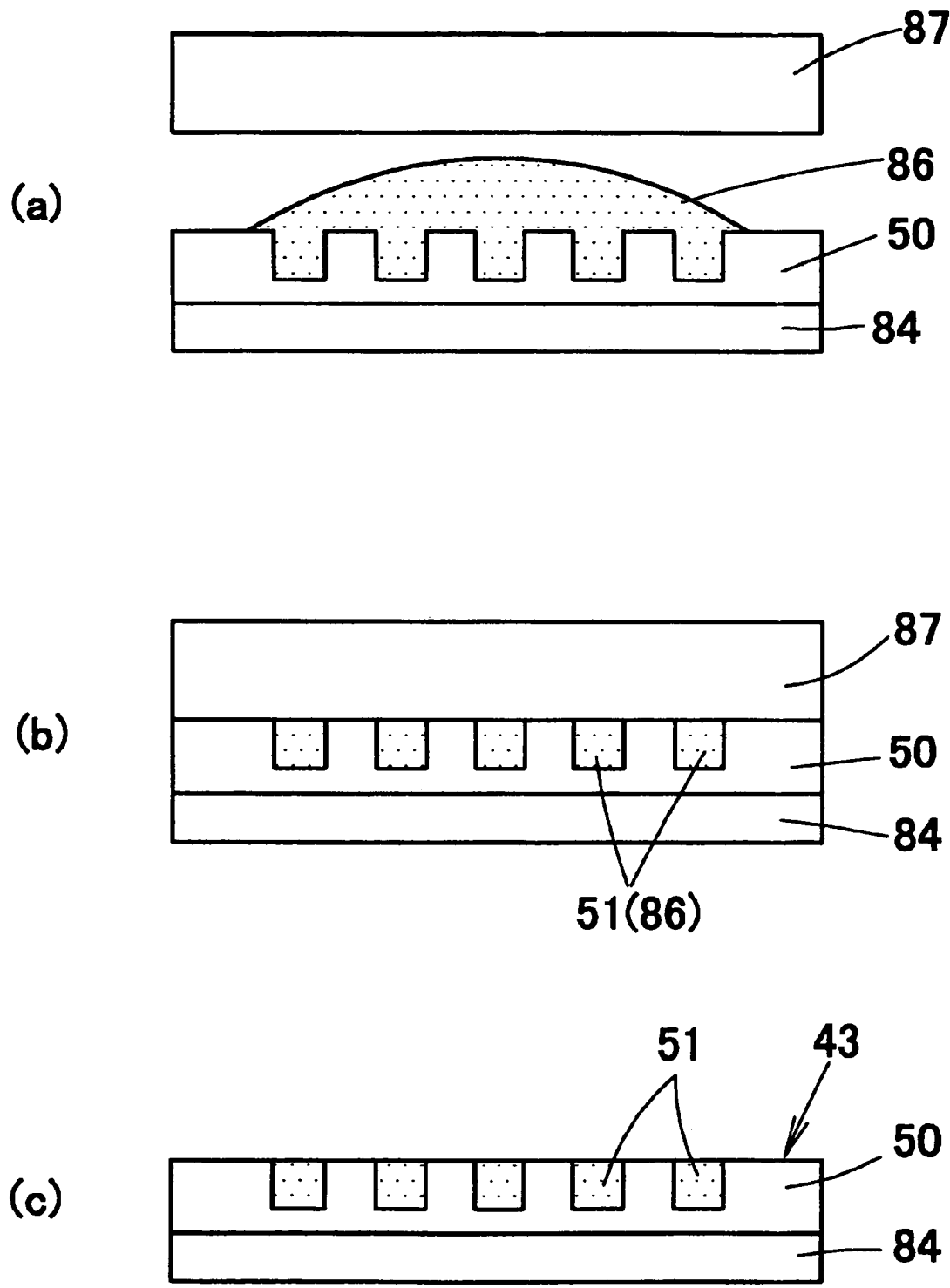

[Fig. 23]
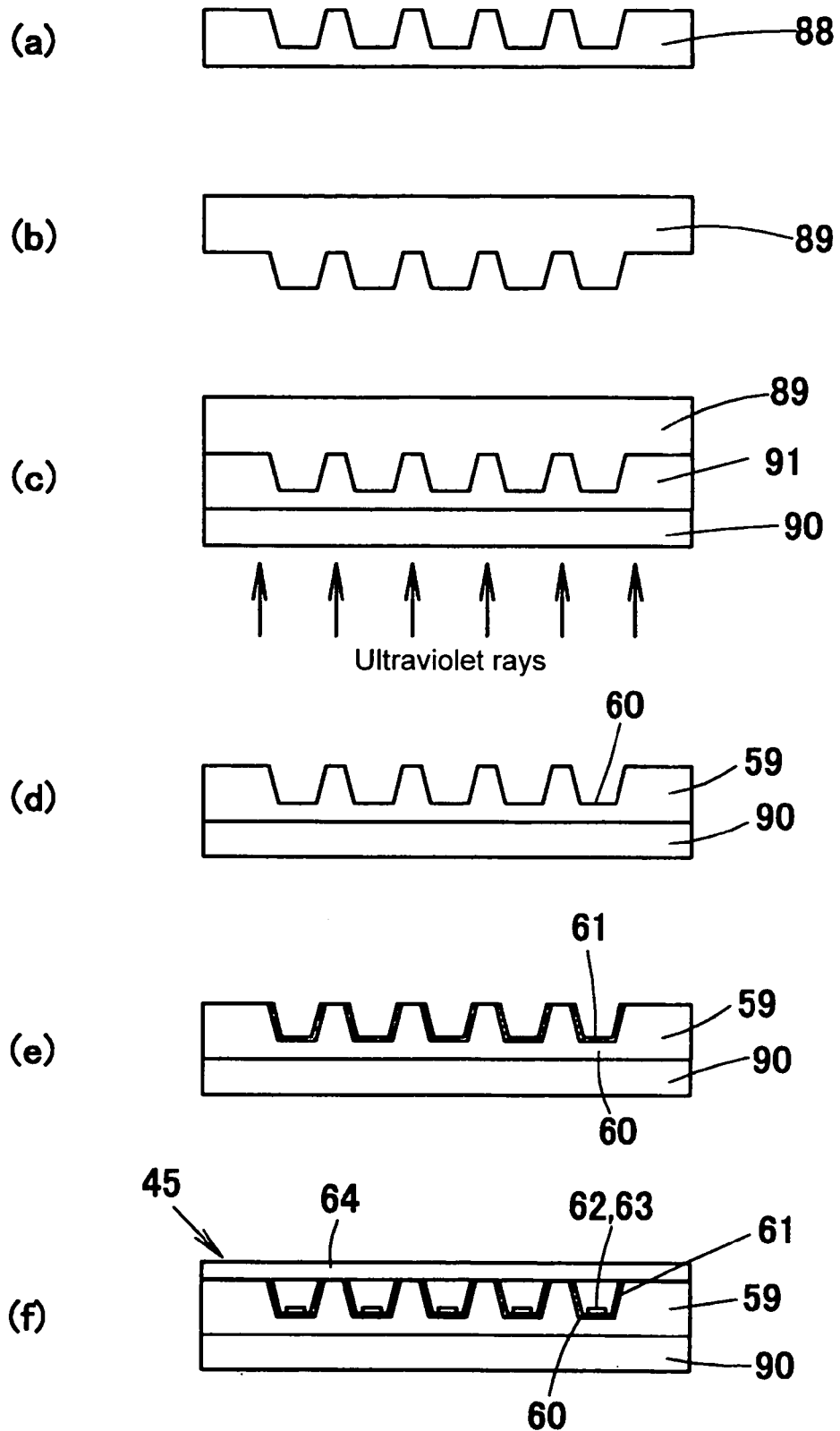

[Fig. 24]
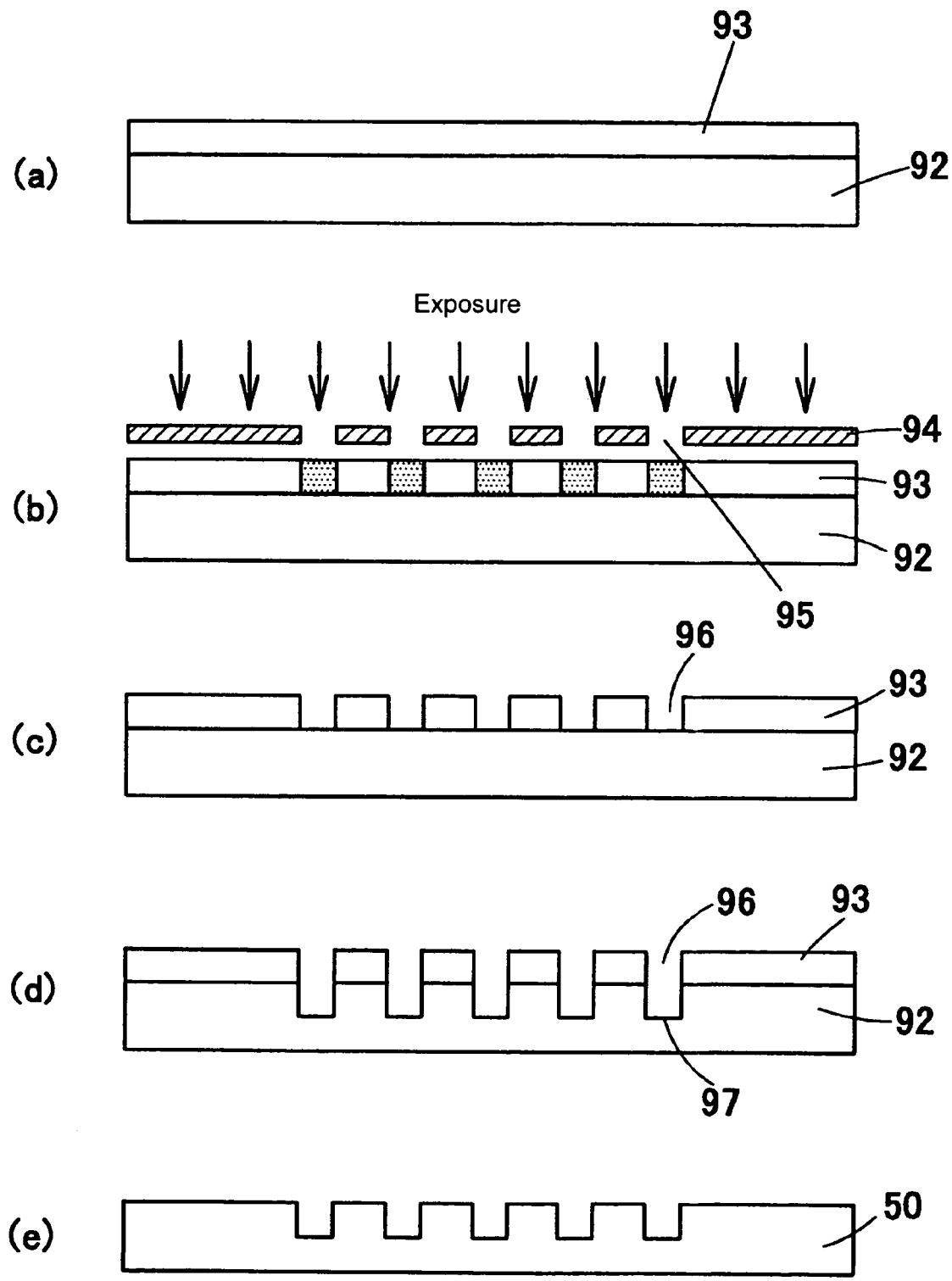

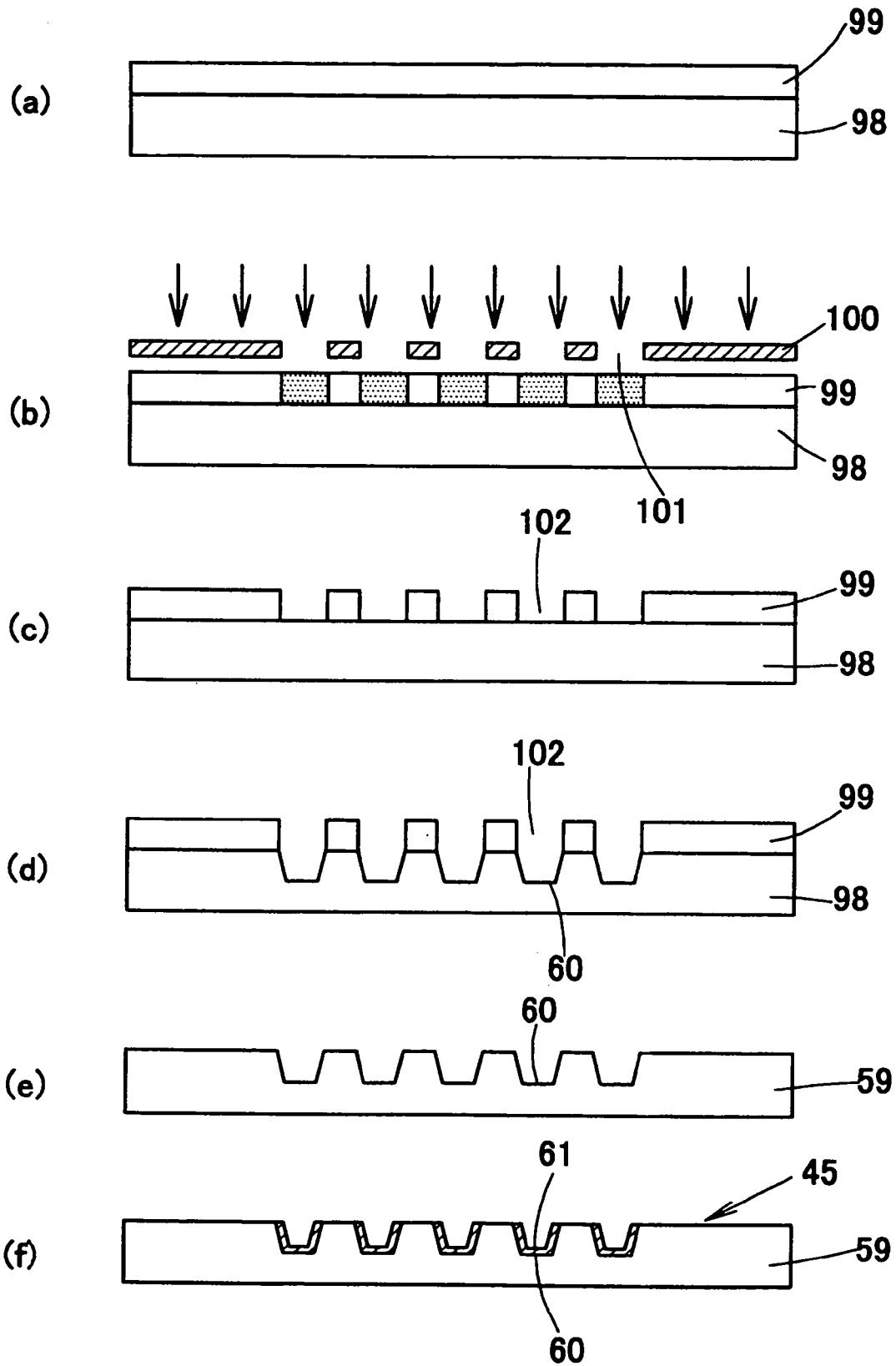
[Fig. 25]

[Fig. 26]
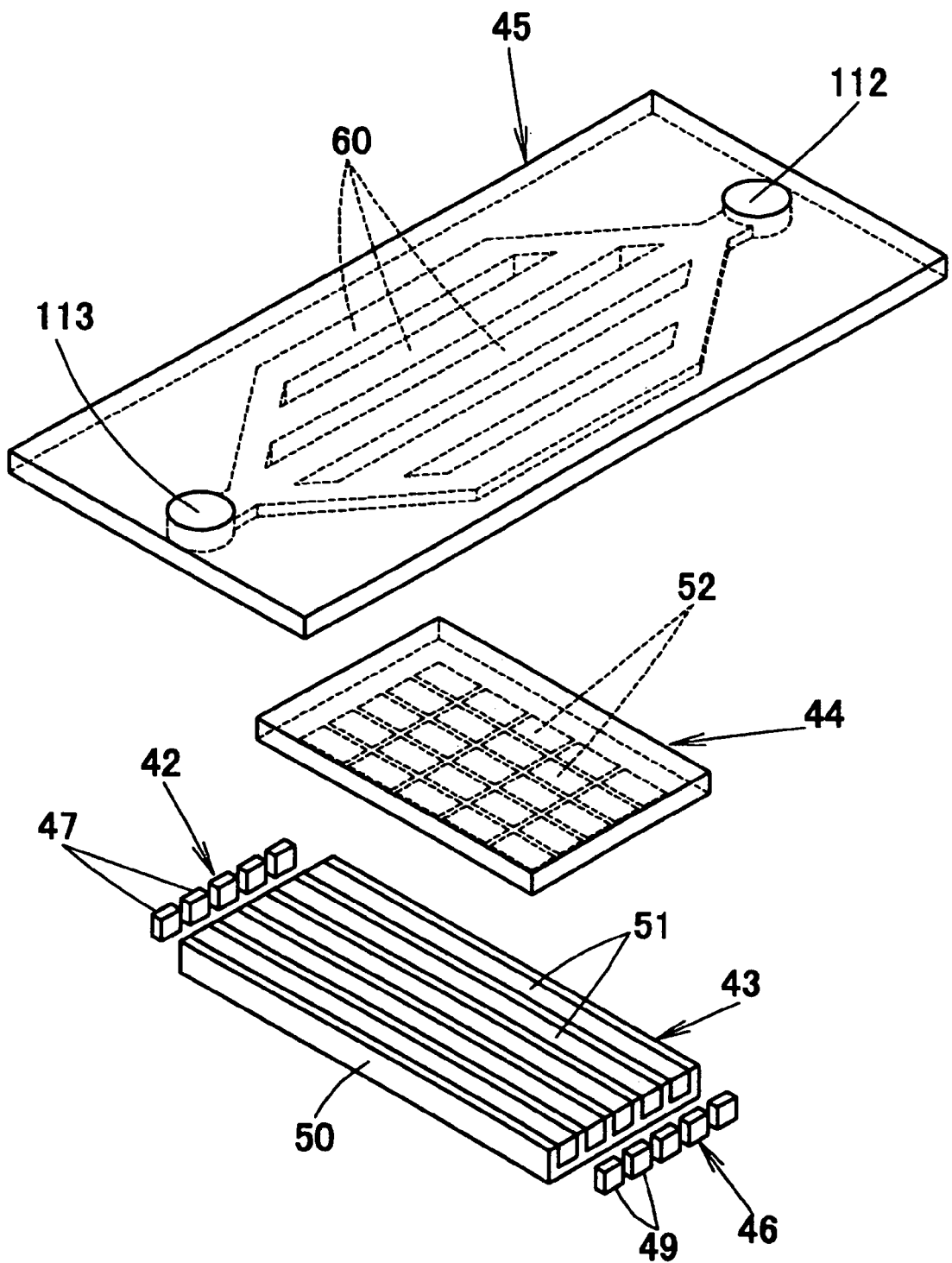

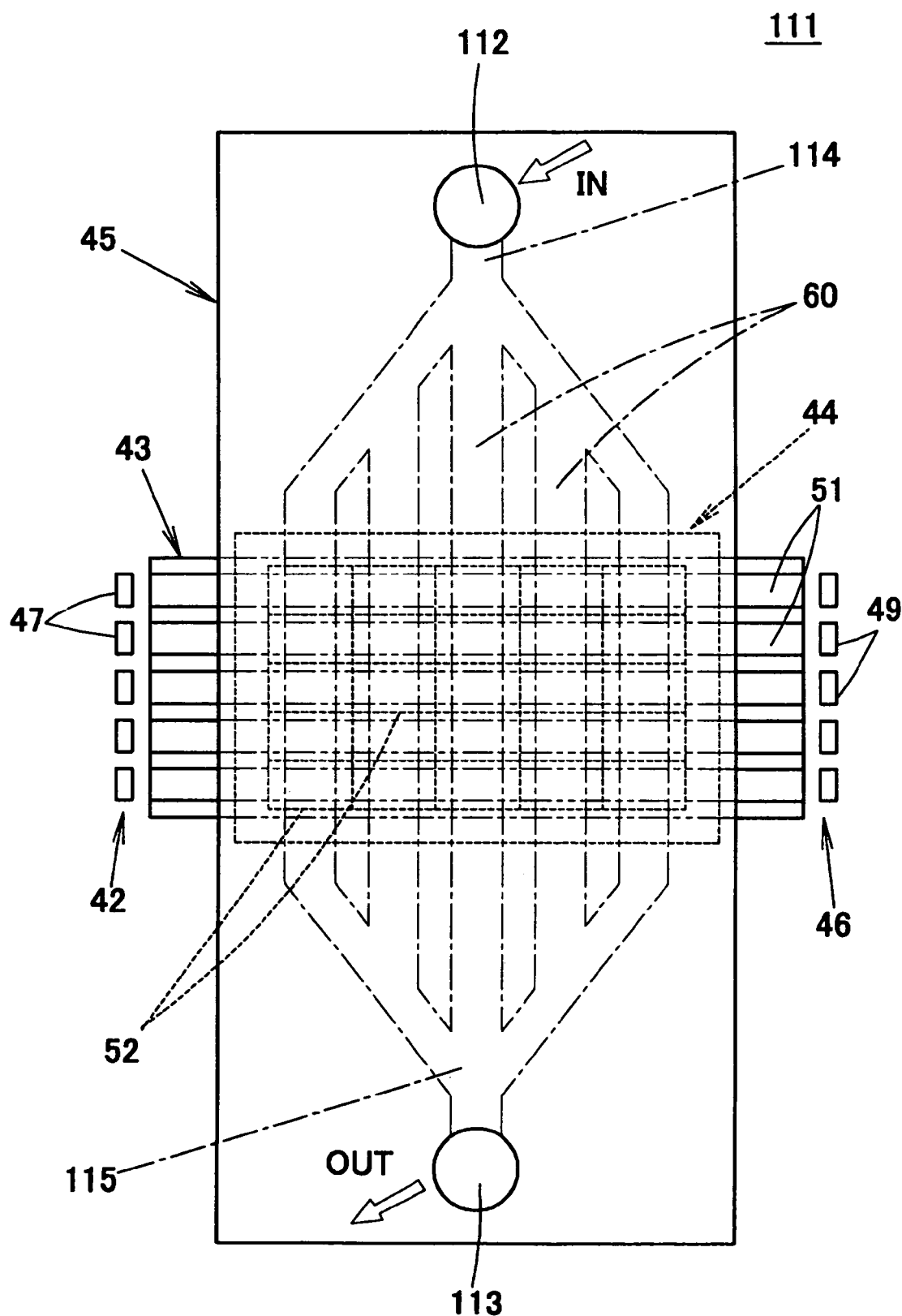
[Fig. 27]

[Fig. 28]
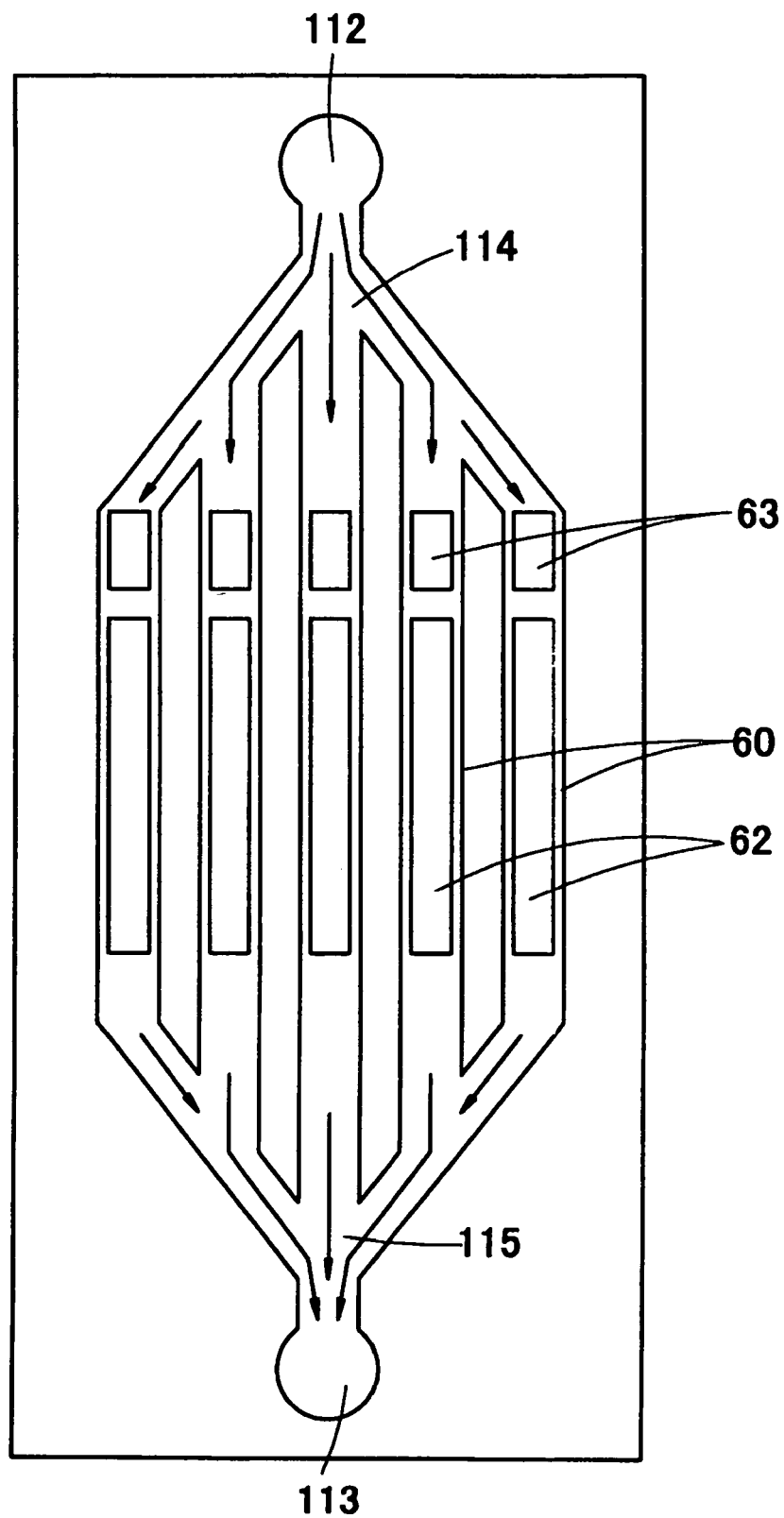

[Fig. 29]
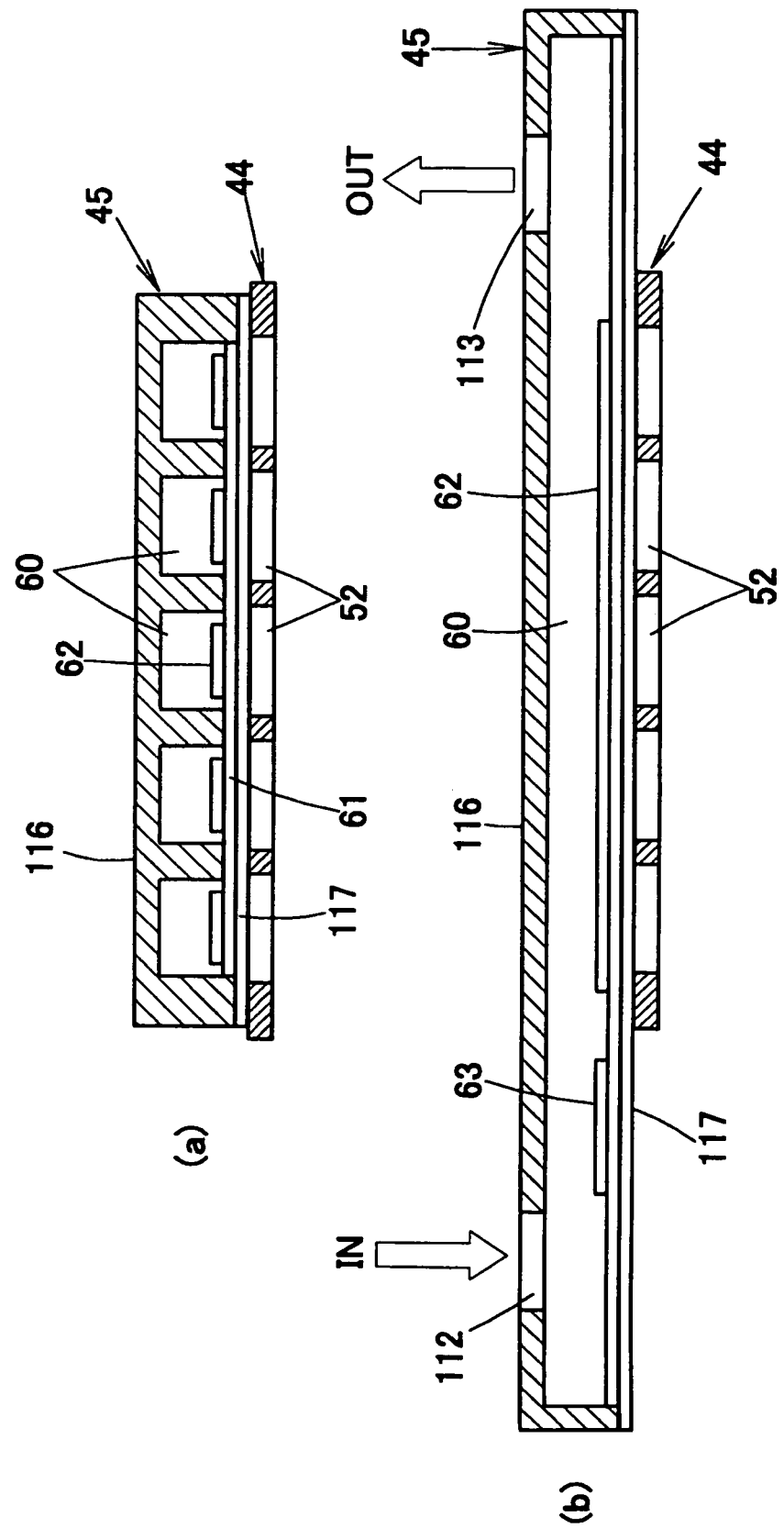

[Fig. 30]
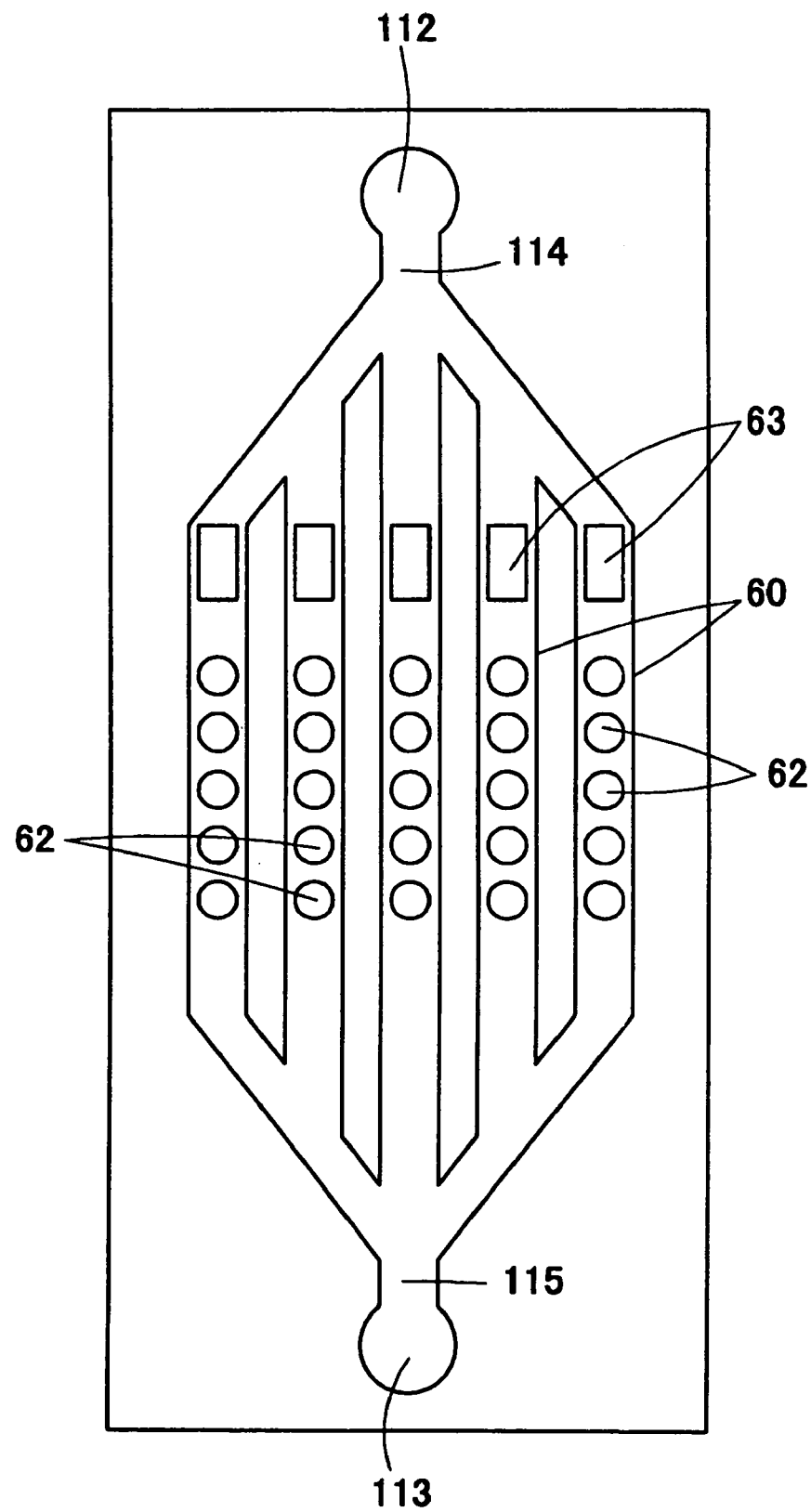

[Fig. 31]
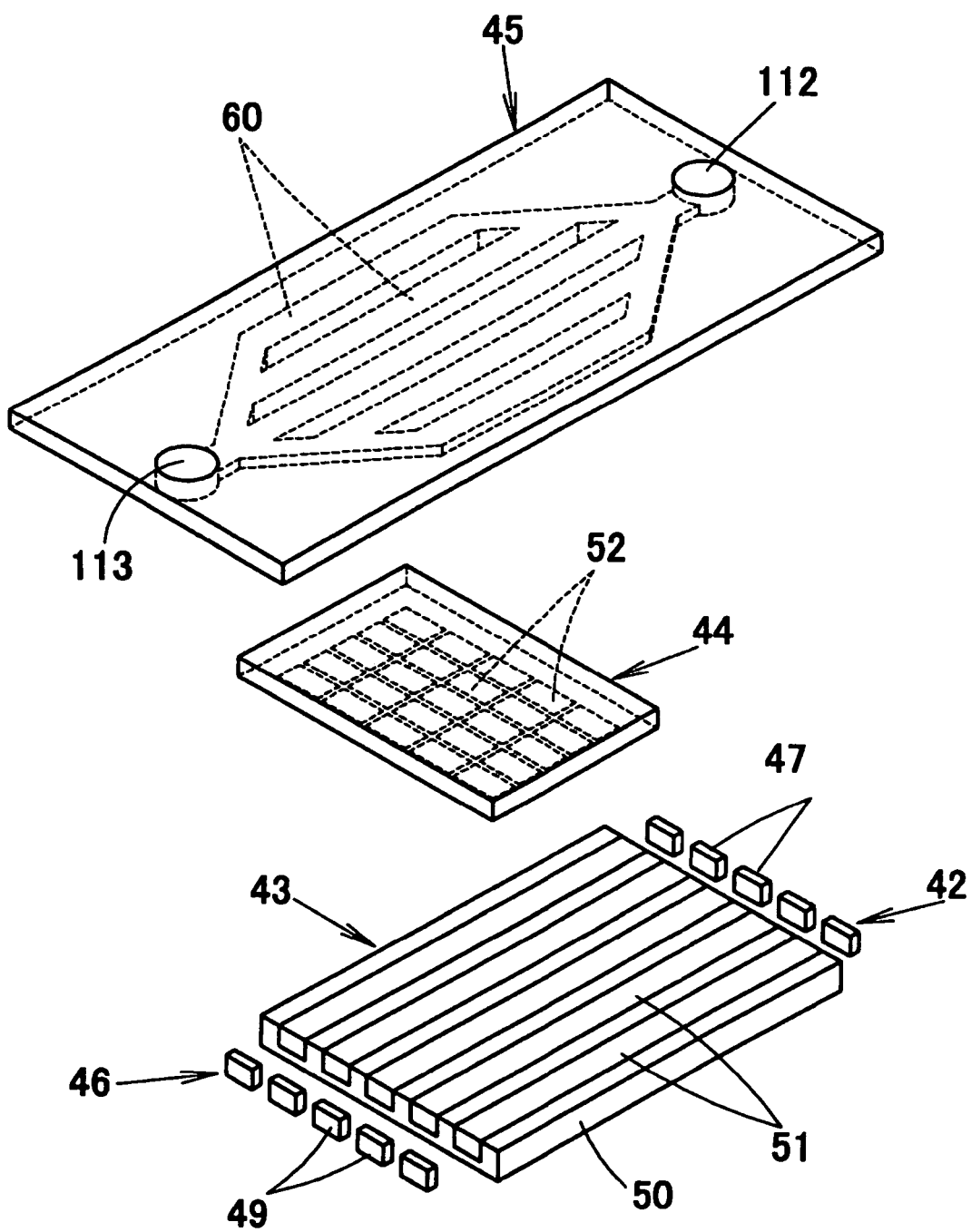

[Fig. 32]
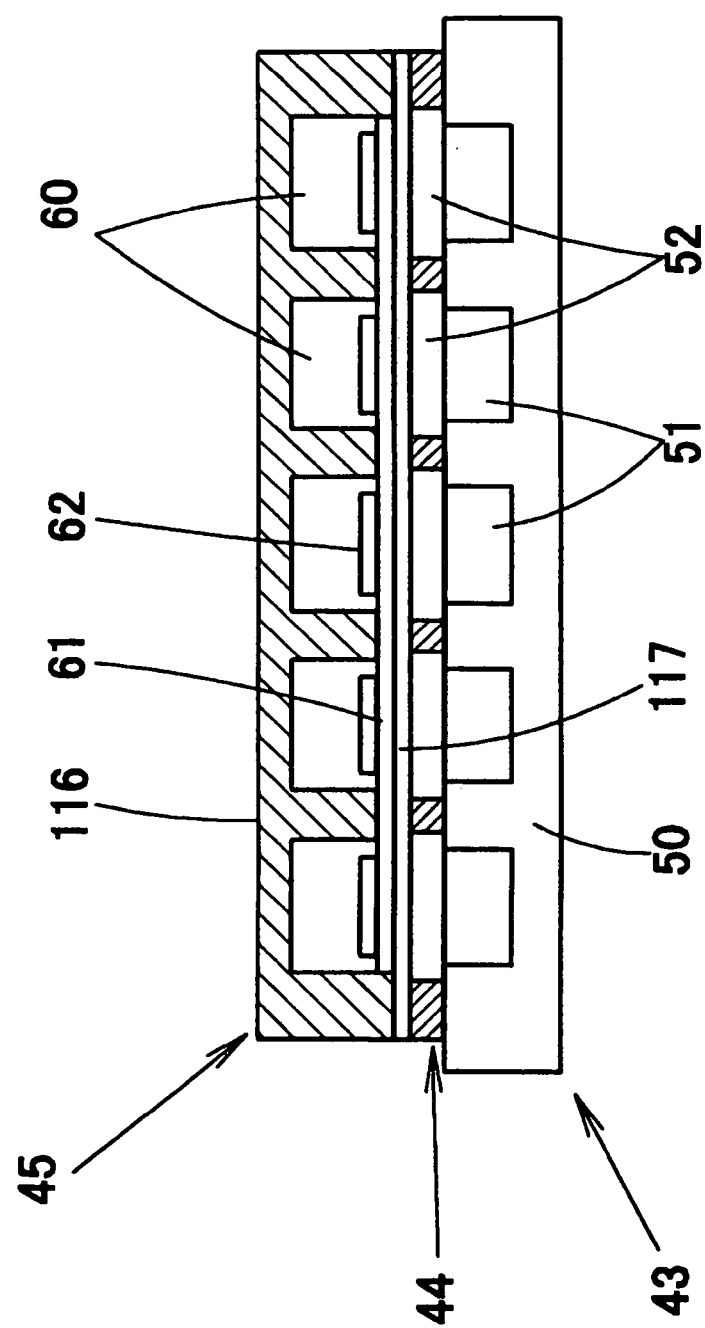

[Fig. 33]
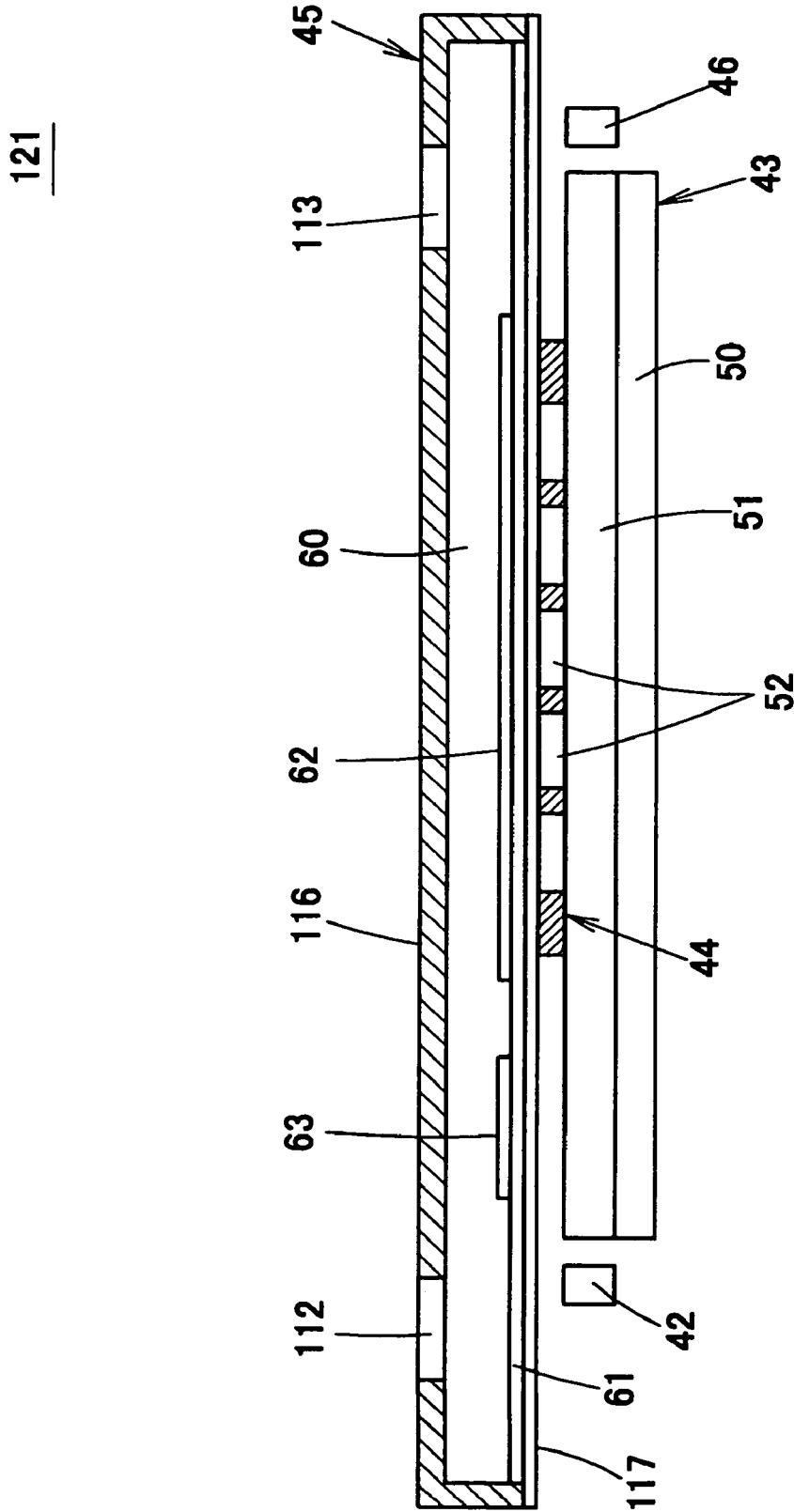

[Fig. 34]
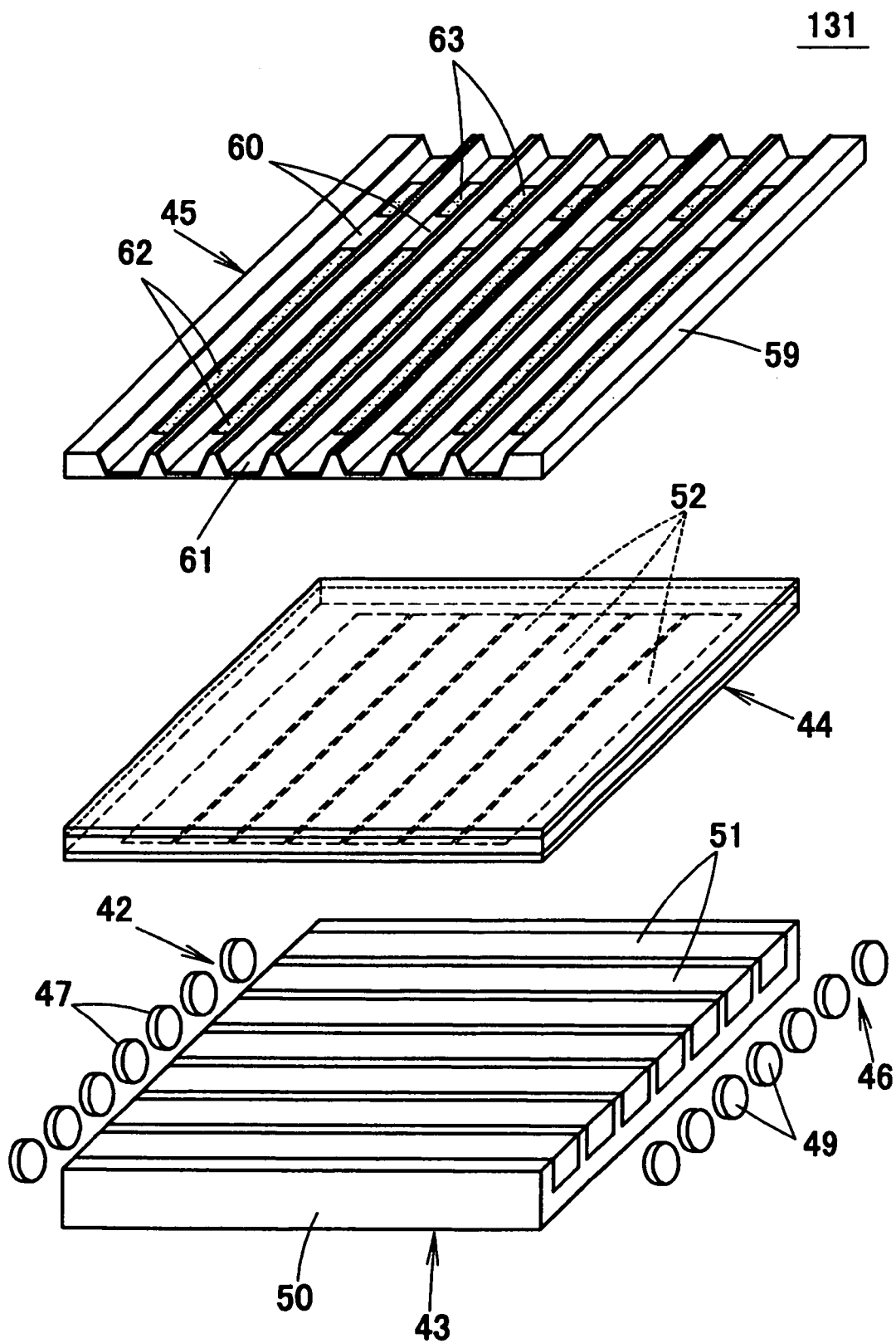

[Fig. 35]
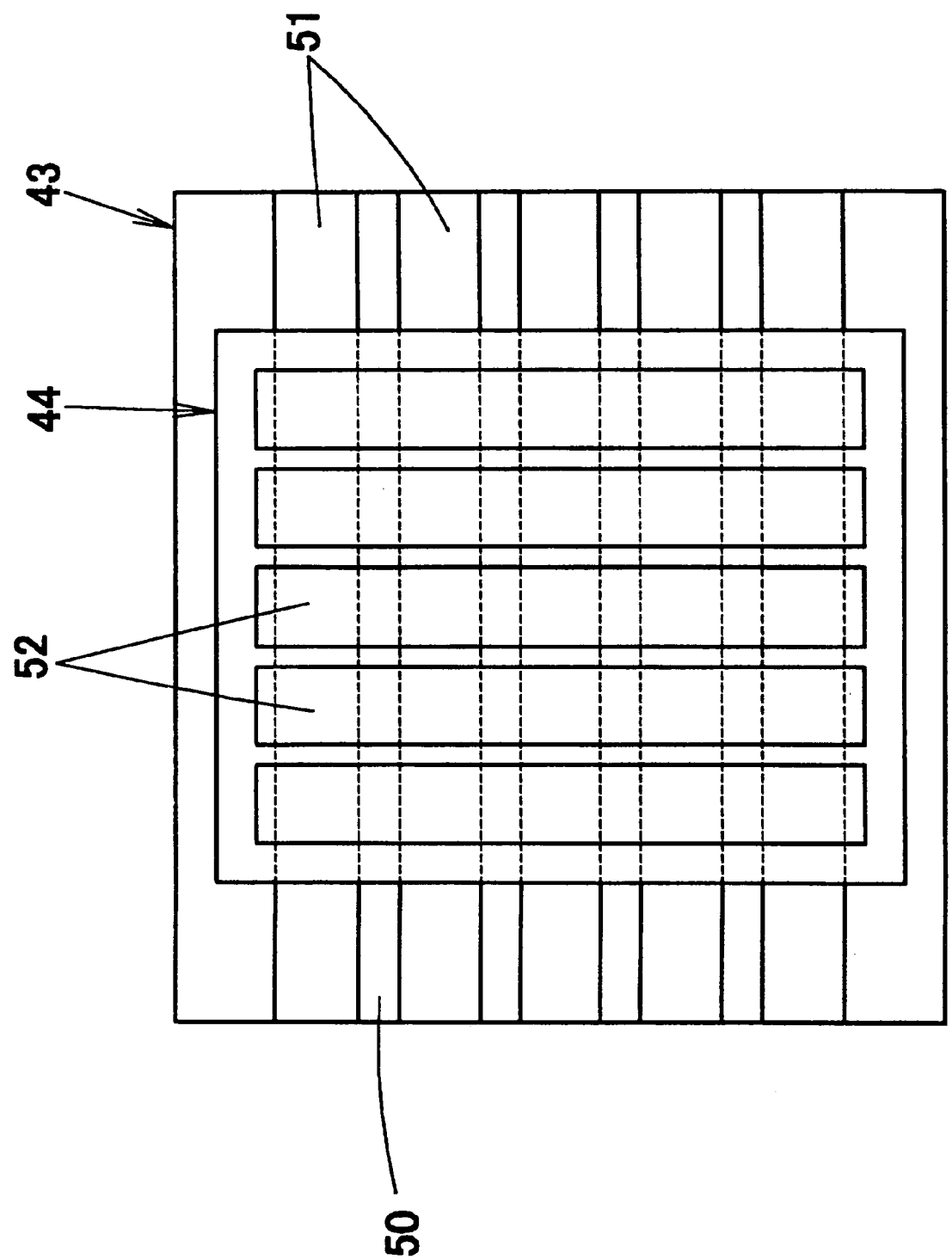

[Fig. 36]
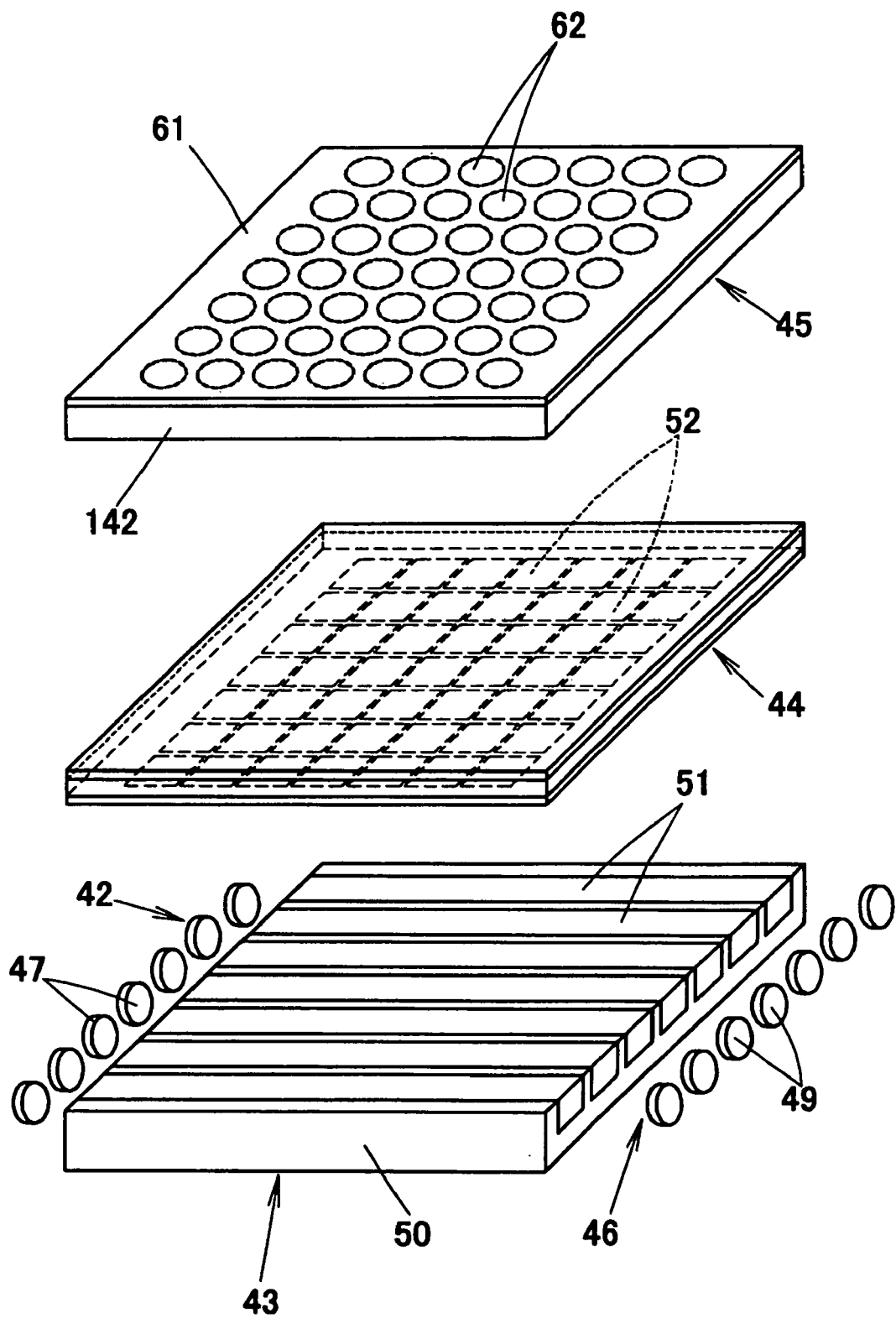

[Fig. 37]
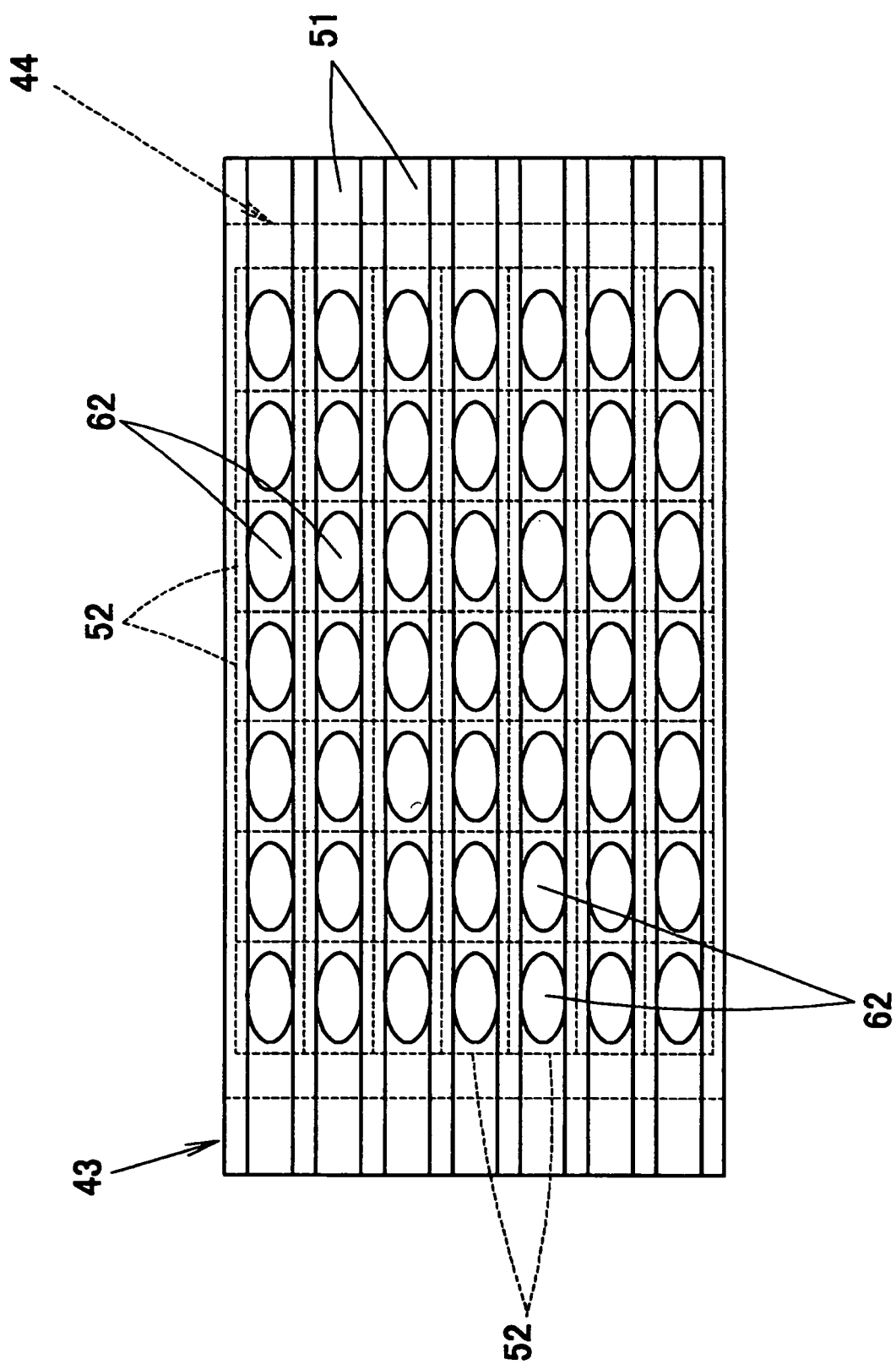

[Fig. 38]
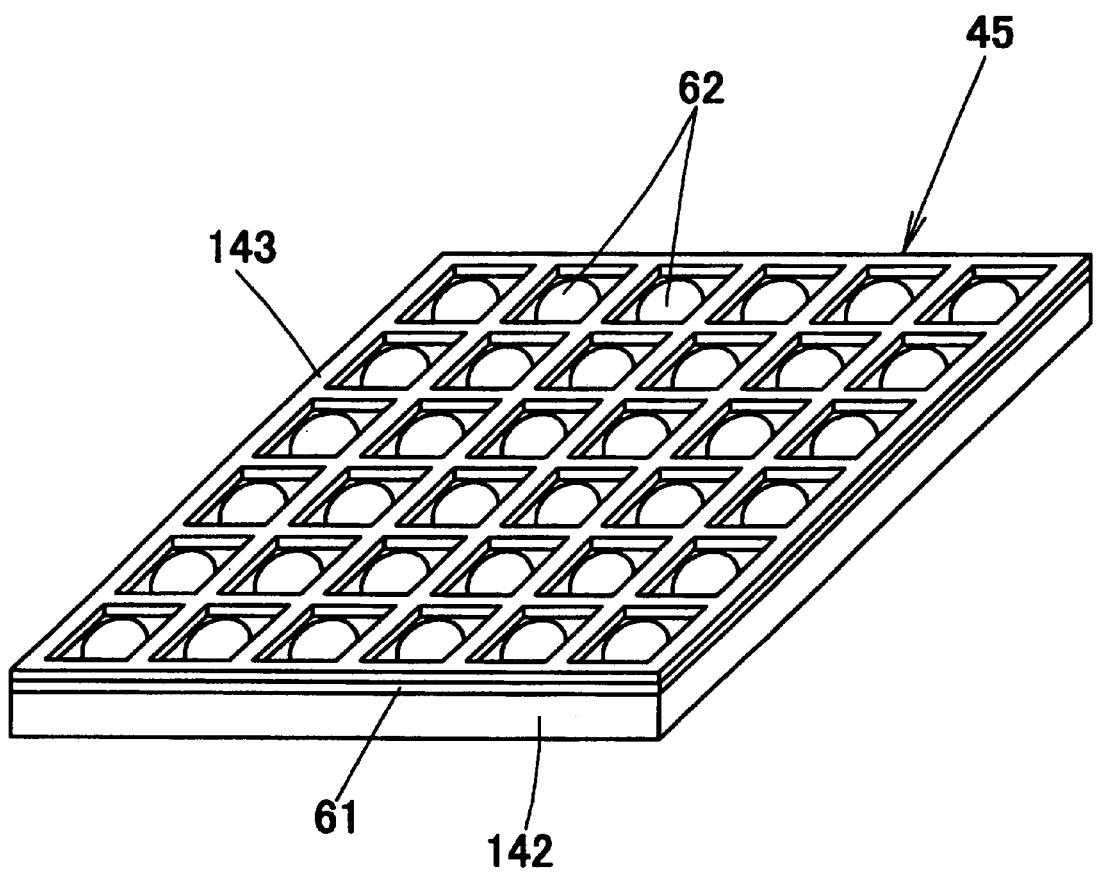

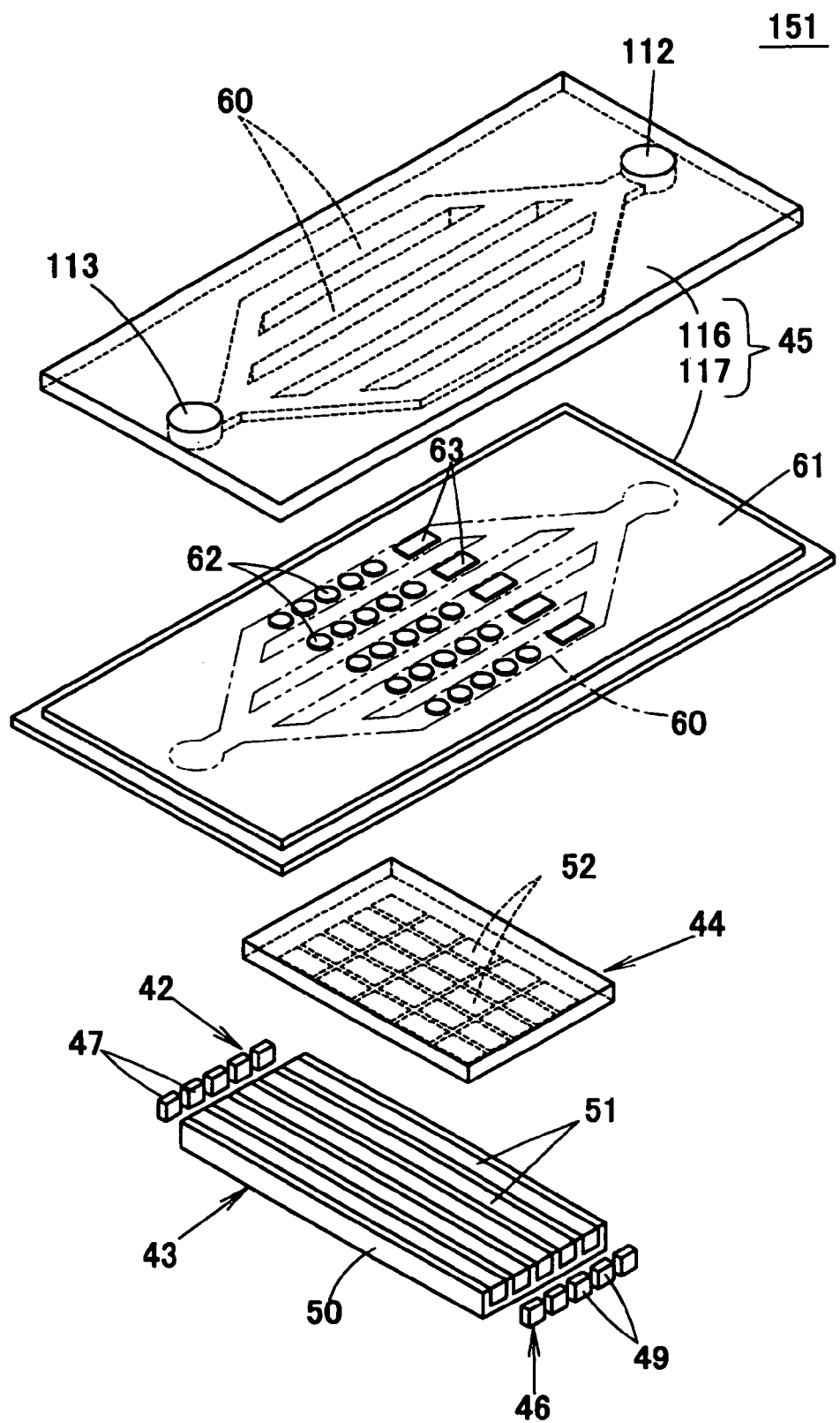
[Fig. 39]

[Fig. 40]
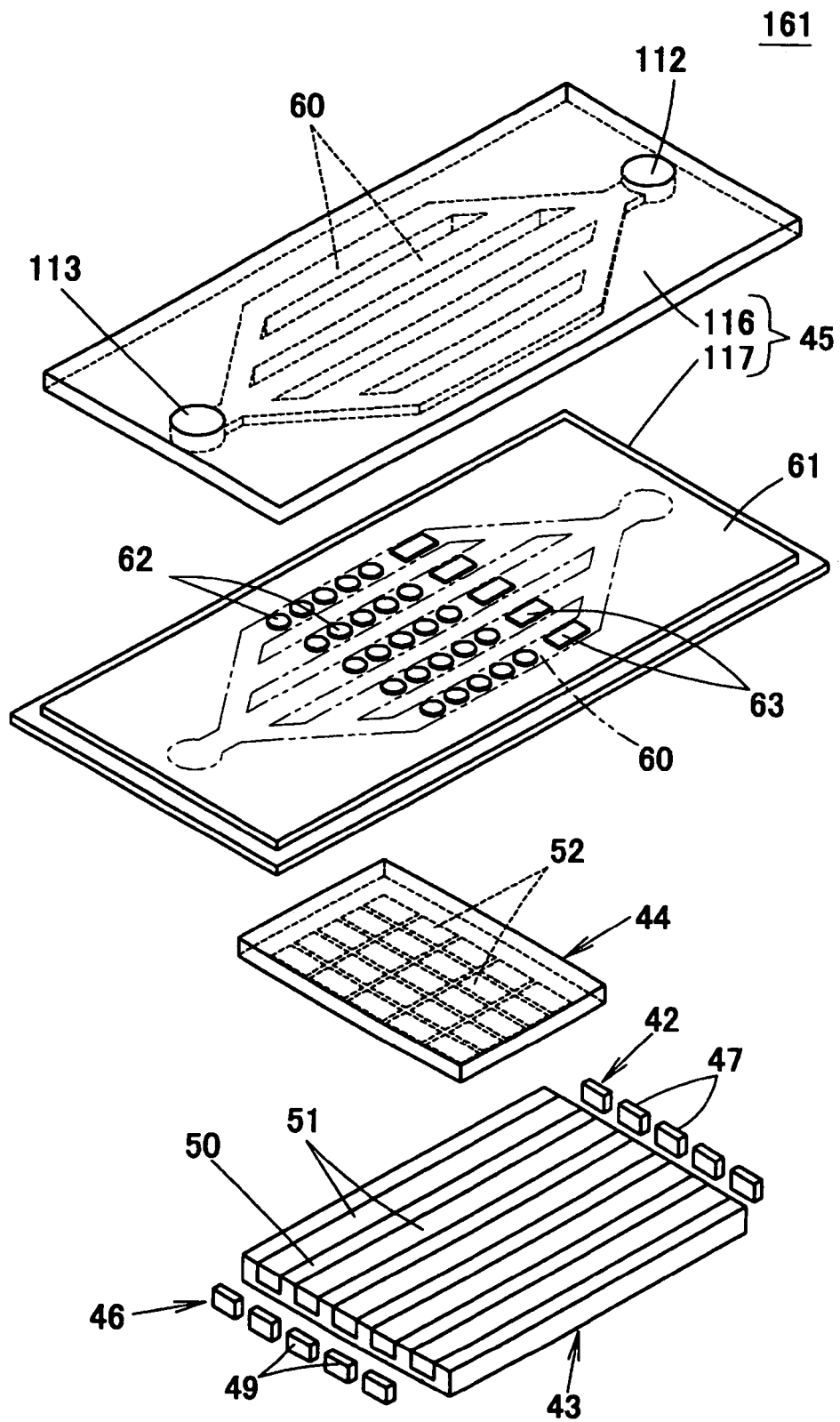

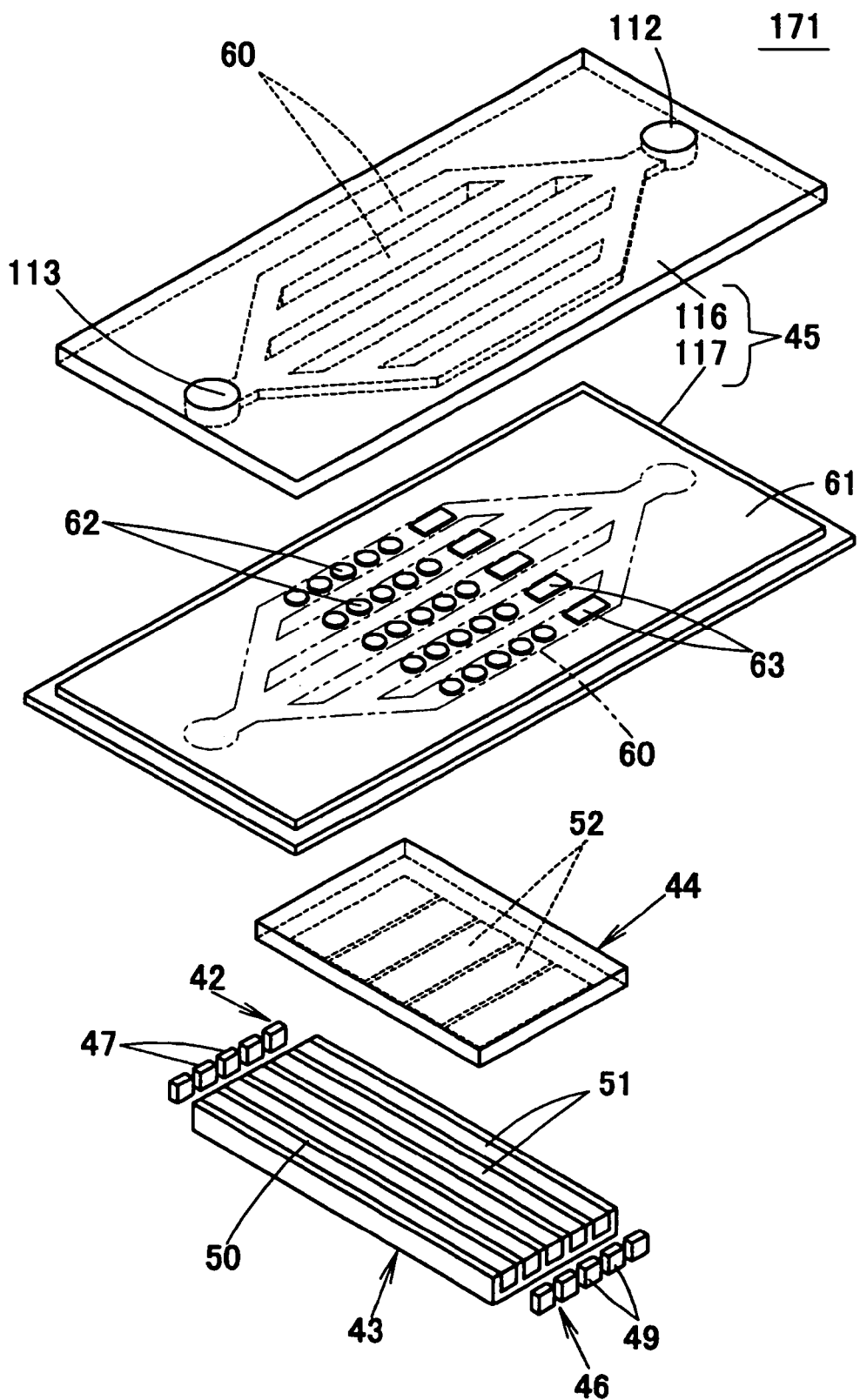
[Fig. 41]

[Fig. 42]
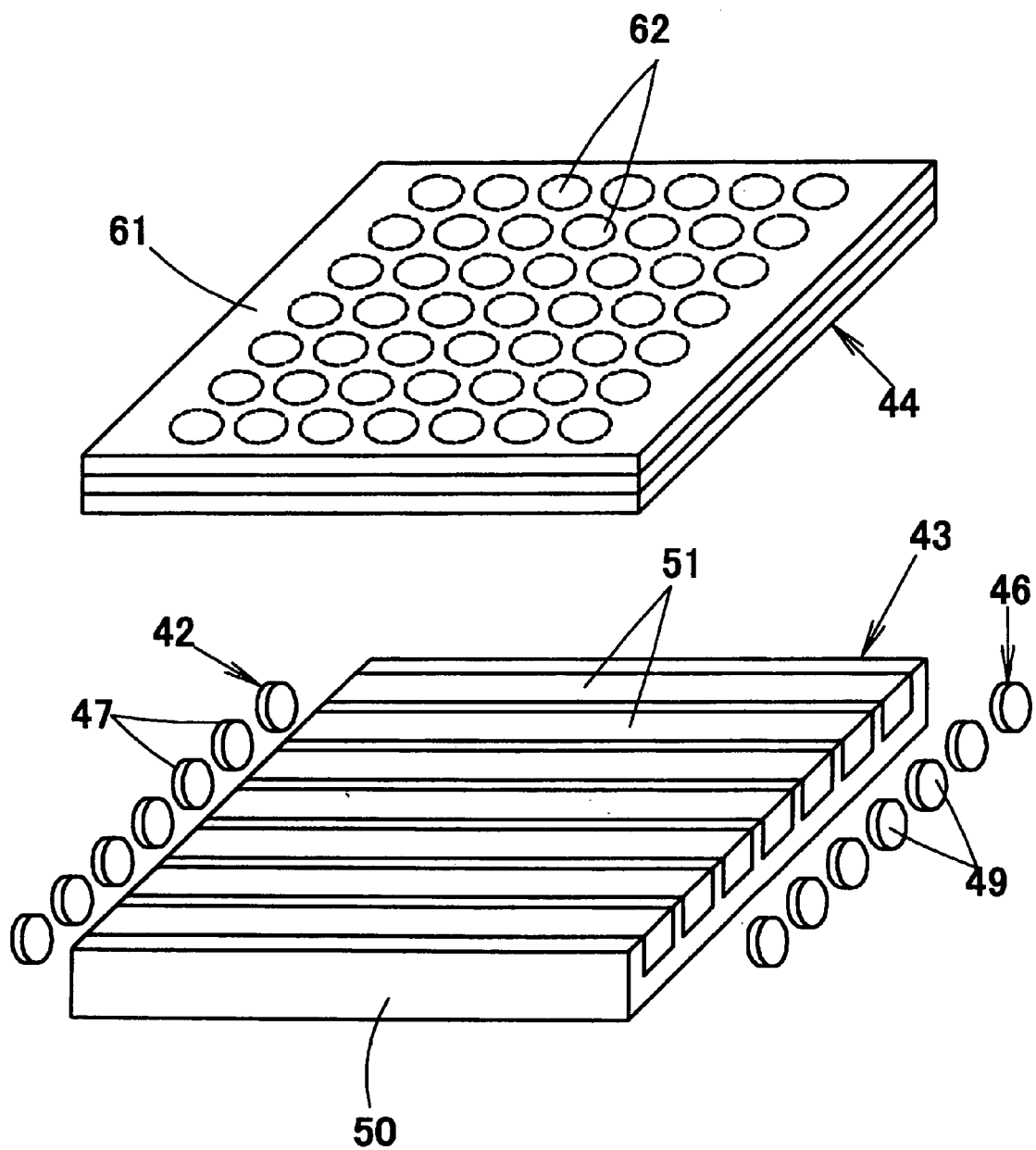

[Fig. 43]
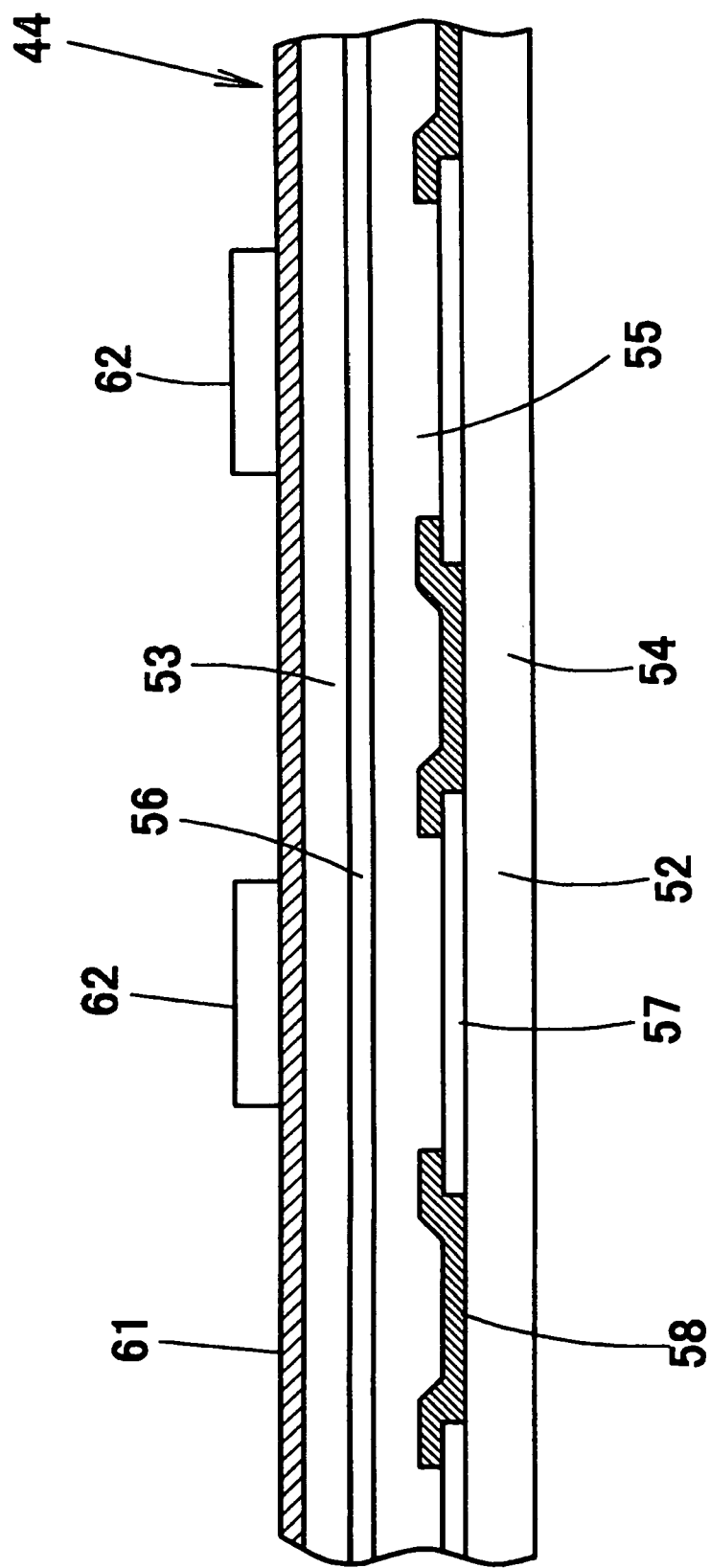

[Fig. 44]
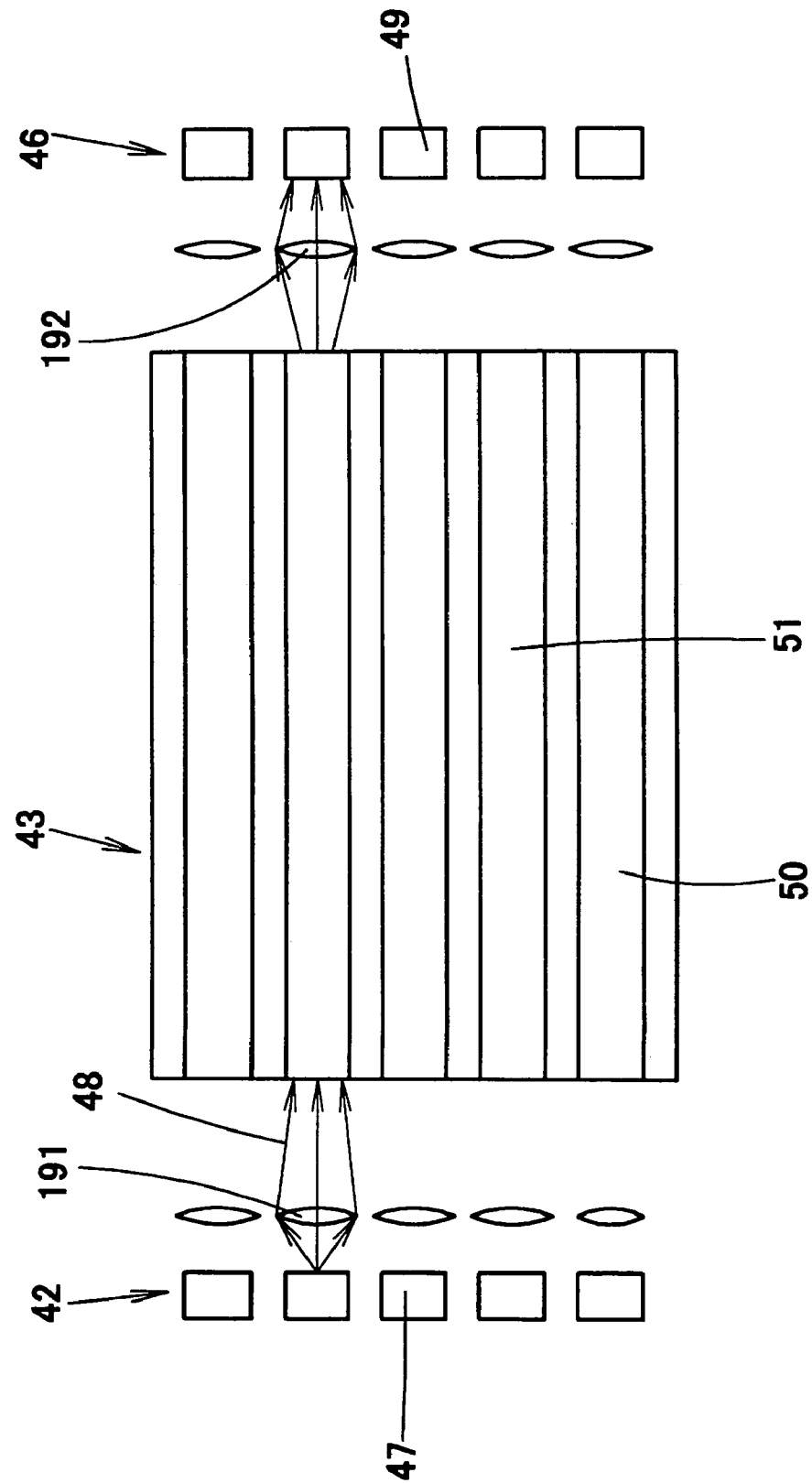

[Fig. 45]
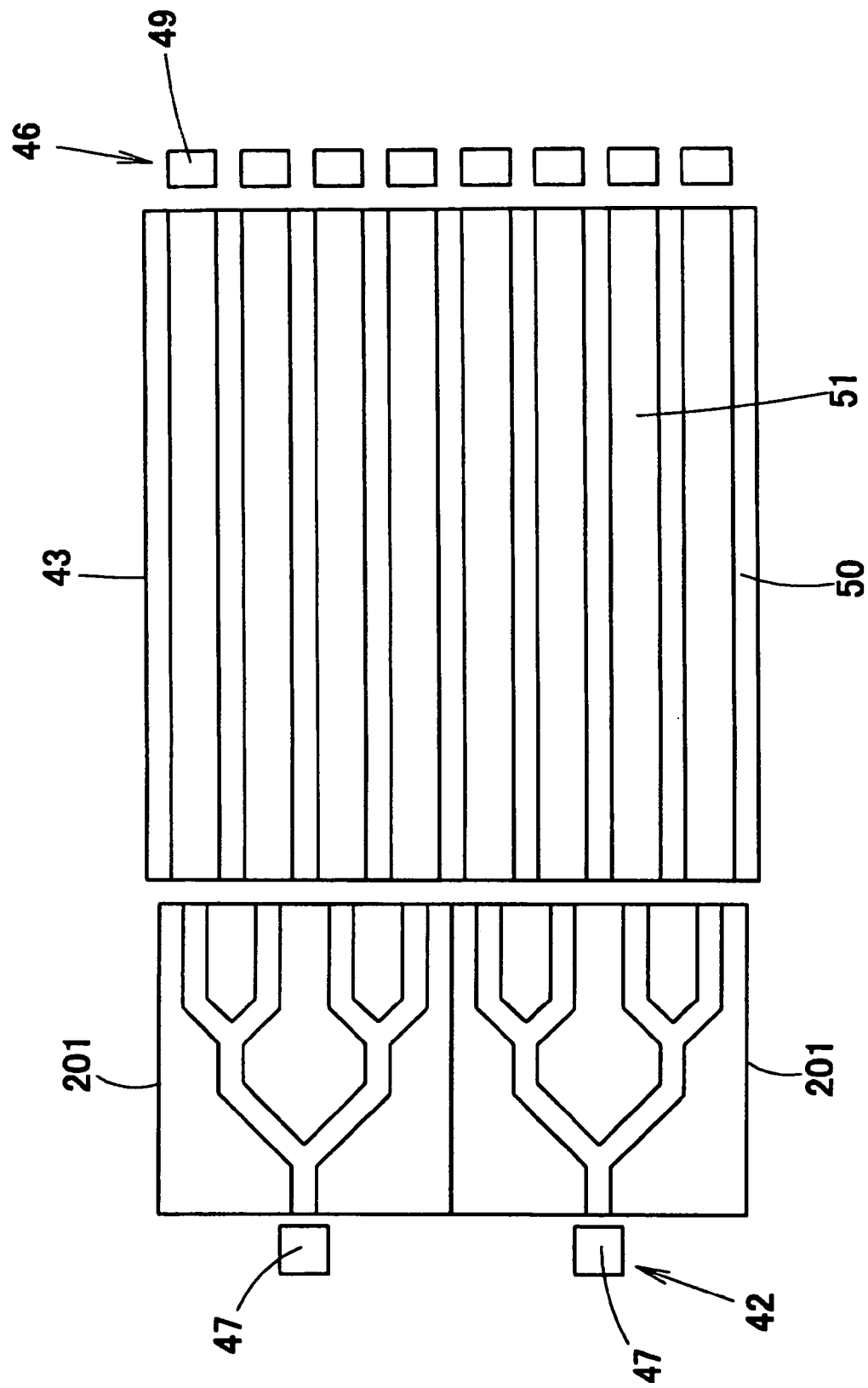

[Fig. 46]
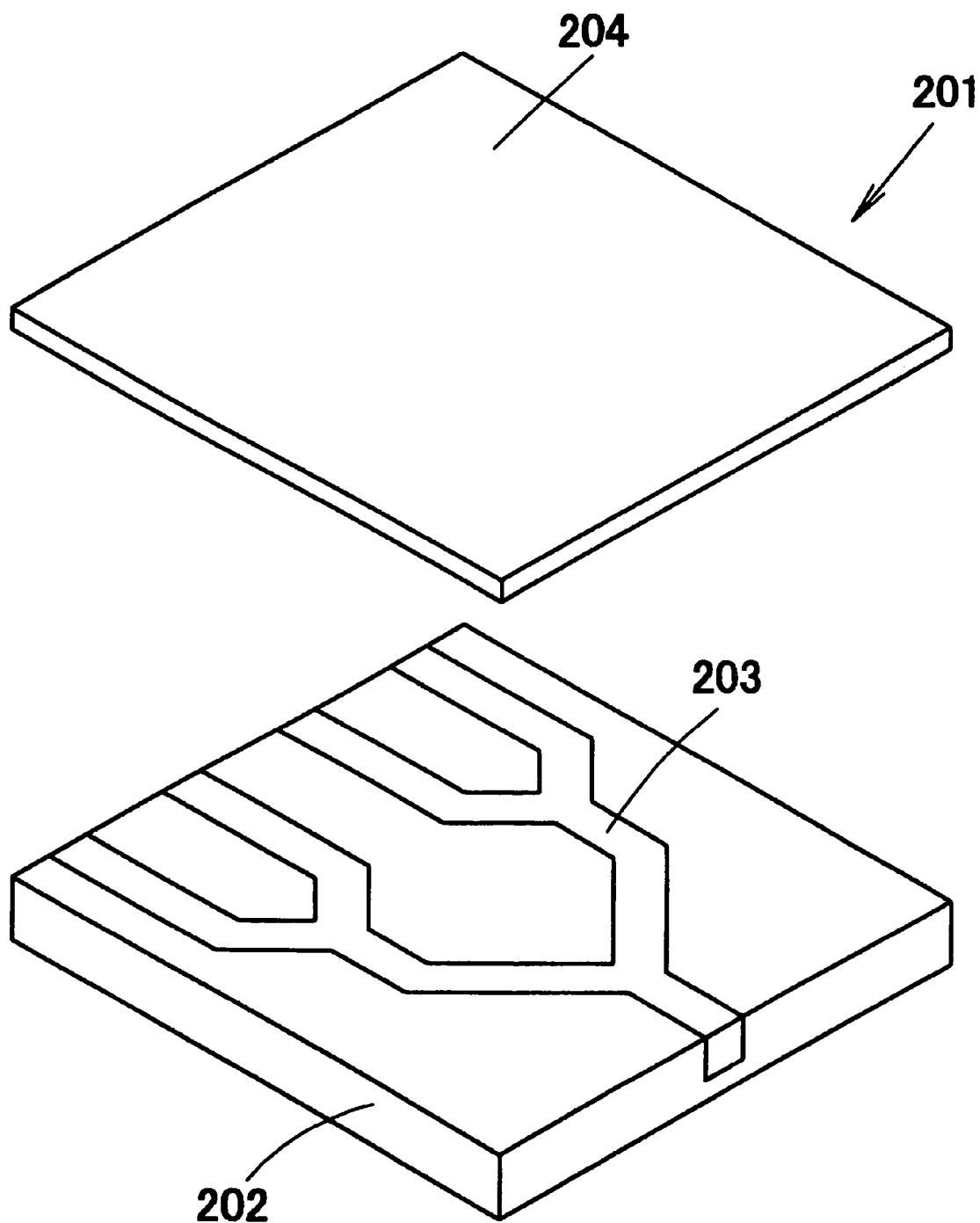

[Fig. 47]
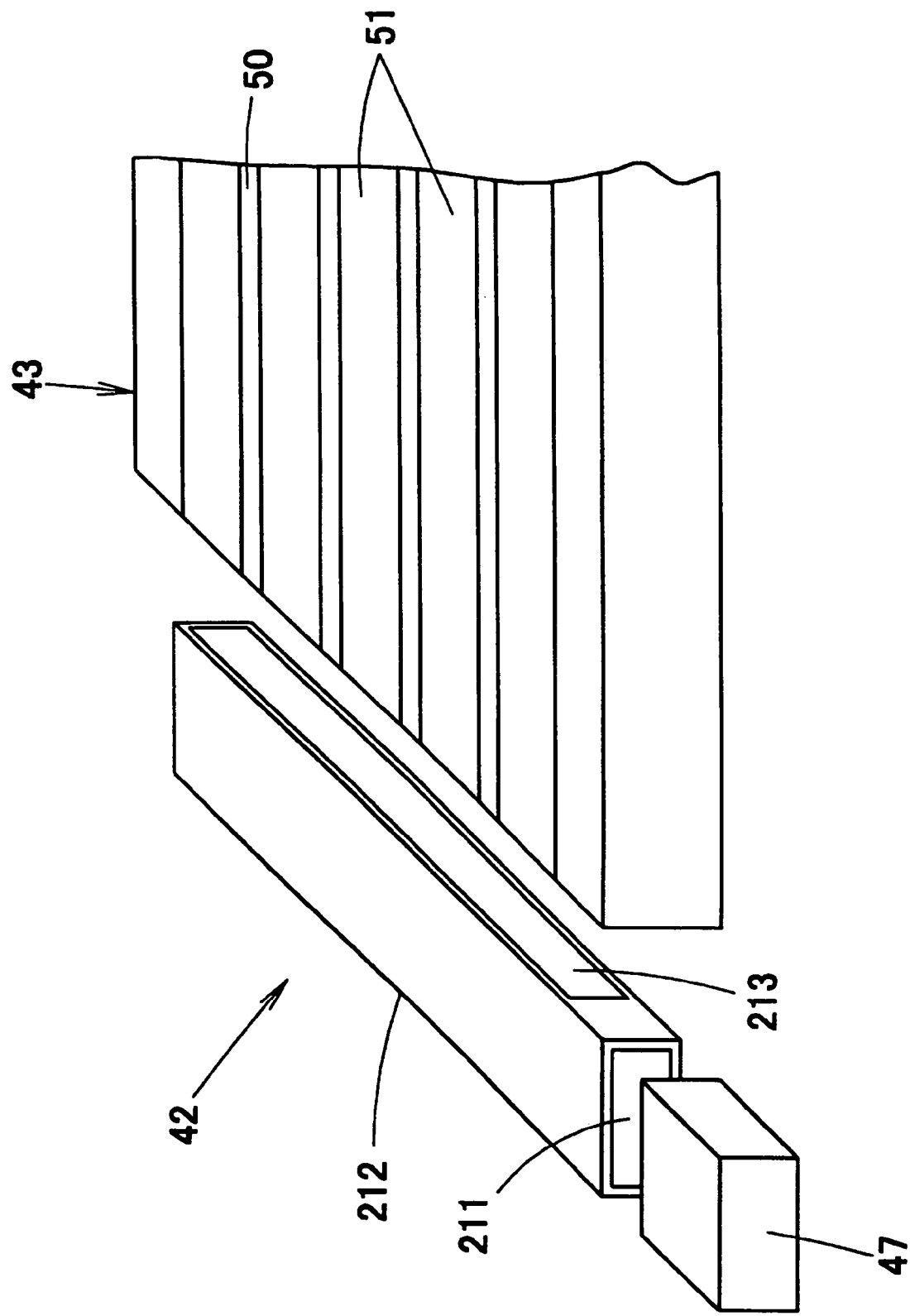

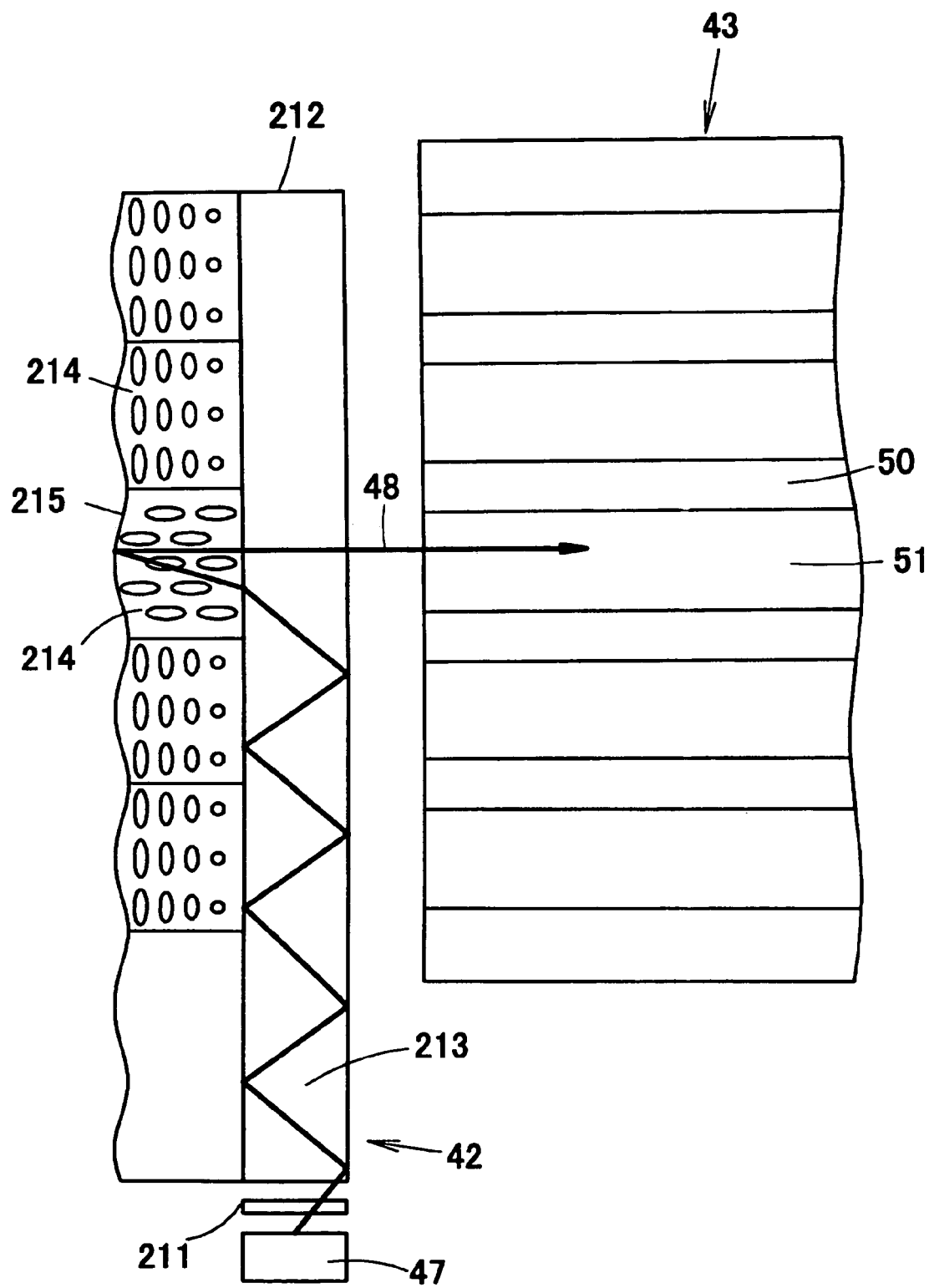
[Fig. 48]

OPTICAL ANALYZING UNIT AND OPTICAL ANALYZING DEVICE

TECHNICAL FIELD

The present invention relates to an optical analyzing device using surface plasmon resonance and an optical analyzing apparatus using the device.

BACKGROUND ART

Prior Art 1

An existing analyzing apparatus for analyzing a gene and a protein will be described below.

As a general analyzing apparatus for analyzing genes and the like, an analyzing apparatus disclosed in Japanese Patent Laid-Open No. 2000-131237 (patent document 1) is known. The analyzing apparatus is shown in FIG. 1. In the analyzing apparatus, known cDNA which is different from each other is applied in dots on a microarray chip 1. By dropping DNA marked with different fluorescent dyes onto the microarray chip 1, cDNA is hybridized to DNA to obtain a single molecule 2.

Excitation light 4 emitted from an excitation light source 3 is condensed by a collimator lens 5 and a condenser lens 6 and is applied to each of the single molecules 2 arranged on the microarray chip 1. The fluorescent light excited by the single molecule 2 is reflected by a polarization beam splitter 7 and received by a photomultiplier 8. On the other hand, the microarray chip 1 is mounted on a stage 9. By driving step motors 10 and 11 to move the stage 9, each of the single molecules 2 can be sequentially scanned. By obtaining the single molecule 2 to which the DNA is hybridized, the DNA is specified.

However, the analyzing apparatus is of a fluorescence detection type and has problems such as detection error caused by a fluorescent molecule, and deactivation of biomolecules such as DNA, protein, and the like accompanying a fluorescent molecule. In the analyzing apparatus, an optical system for fluorescence detection is large and expensive and, further, a driver for scanning is also large. As a result, the analyzing apparatus as a whole is large and expensive. In addition, it takes time to scan the excitation light 4, so that it is difficult to realize high throughput.

Prior Art 2

FIG. 2 shows another conventional analyzing apparatus disclosed in Japanese Patent Laid-Open No. 2001-255267 (Patent Document 2). In the analyzing apparatus, a plurality of kinds of antibodies are fixed on a metallic thin film 22 formed on the surface of a prism 21 and substances 25 to be measured are introduced to the antibodies. Light emitted in a lattice shape from a light source 23 is allowed to enter as p-polarized parallel beams one side of the prism 21. The light reflected by the metallic thin film 22 includes absorption caused by the surface plasmon resonance phenomenon and a two-dimensional light reception amount of the reflection light is received by a CCD camera 24.

In such an analyzing apparatus, an image 27 of an actual measurement surface 26 is distorted in the CCD camera 24 and the aspect ratio (the ratio of width to height) changes. Consequently, the aspect ratio of the image is corrected, thereby generating a corrected image 28. After that, image processing is performed and the substance 25 to be measured is analyzed.

The analyzing apparatus utilizing the surface plasmon resonance phenomenon has an advantage that an error caused by a fluorescent molecule does not occur. In the case where a change in resonance condition is small, a high-precision optical system is necessary. It causes a problem such that an optical system using a conventional bulk element is large and expensive. Since it is also necessary to perform image processing, there are also problems such that the apparatus is large and analysis time is long.

Prior Art 3

FIG. 3 shows further another conventional analyzing apparatus utilizing the surface plasmon resonance phenomenon, which uses an optical waveguide 33 in which a plurality of cores 32 are formed in cladding 31. On the cores 32, metallic thin films 34 are provided so as to be in contact with the cores 32. Different antibodies are fixed on the metallic thin films 34, a substance to be measured is supplied, p-polarized light is led to each of the cores 32, the spectrum of light emitted from each of the cores 32 is measured, and the substance to be measured is examined by using the surface plasmon resonance.

Since the analyzing apparatus uses the optical waveguide in place of the prism, the optical system used for the surface plasmon resonance analyzing apparatus can be miniaturized. In the analyzing apparatus, however, the number of tests performed at once is equal to the number of the cores 32, so that sufficient high throughput cannot be realized.

Patent document 1: Japanese Patent Laid-Open No. 2000-131237

Patent document 2: Japanese Patent Laid-Open No. 2001-255267

Patent document 3: Japanese Patent Laid-Open No. 2002-162346

In recent years, by testing genes and proteins of a person, grasp of his/her health conditions, early detection of a disease, further, tailor-made therapy, and the like are being realized more and more. However, for analysis of genes and proteins in the tests, a large-sized expensive apparatus, for example, an analyzing apparatus utilizing the surface plasmon resonance has to be used. Consequently, the tests and analysis are conducted mainly in research institutes. The number of apparatuses spread is limited and the analyzing apparatus is not widely spread. Therefore, further spread of such an analyzing apparatus in future is desired. To make the analyzing apparatus used at the consumer level, a small-sized cheap analyzing apparatus is in demand. A palm-sized or portable-sized analyzing apparatus which can be carried by a person is desired. An analyzing apparatus used in a hospital, a public institute, or the like is required to have high throughput which can test a large amount of samples at once.

In the prior arts 1 to 3, however, the analyzing apparatuses are large and very expensive, and their throughputs are not yet satisfactory. Further, affinity, interaction, equilibrium constant, and the like of genes, proteins, and the like cannot be measured with high precision.

DISCLOSURE OF THE INVENTION

Problems to be Solved by the Invention

The present invention has been achieved in view of the technical drawbacks and an object of the invention is to provide an optical analyzing device and an optical analyzing apparatus realizing reduction in size and cost and large improvement in throughput by using multiple channels. Another object is to provide an optical analyzing device and an optical analyzing apparatus capable of measuring affinity, interaction, equilibrium constant, and the like of genes, proteins, and the like with high precision.

An optical analyzing device of the present invention includes: a light source; a waveguide having a plurality of cores and guiding light from the light source in the cores while allowing the light to repeat reflection; a photodetector for receiving the light guided through the cores in the waveguide; a switch having a plurality of switching elements each of which can be switched between a state where an object to be measured is detected and a state where the object to be measured is not detected, and overlapping the waveguide so that the plurality of switching elements are arranged in the length direction of the cores; and a measurement object disposing area determined as a face in a position facing the waveguide via the switch. The switching elements may be independent on a core basis or may be provided across a plurality of cores.

In the optical analyzing device, only a switching element corresponding to a measurement portion in the measurement object disposing area is switched to the detection state among the switching elements arranged along a core corresponding to the measurement portion in the measurement object disposing area, and light emitted from the light source, guided in the core, and modulated in the measurement portion via the switching element in the detection state is detected by the detector, thereby enabling a change in the light intensity in the measurement portion and a fluorescent color to be detected. By detecting a change in light intensity or a fluorescent color, the king and amount of an object to be measured which is placed in the measurement portion can be measured, and characteristics such as intermolecular interaction, affinity, equilibrium constant, and the like of the object to be measured can be evaluated. Particularly, when gene, protein, or the like is used as an object to be measured, the device can be used as a biochip. A surface plasmon resonance analyzing apparatus can be constructed by the optical analyzing device and means (for example, analysis software or a computer system) for analyzing the kind, amount, or characteristic (such as physical characteristic, chemical characteristic, or biological characteristic) of the object to be measured on the basis of an output of the optical analyzing device by using the surface plasmon resonance phenomenon.

Since the waveguide (optical waveguide) is used for guiding light in the optical analyzing device of the present invention, as compared with a device for emitting light to a space, higher sensitivity can be achieved and measurement precision can be improved. Since the switch constructed by the switching elements is used, as compared with the technique of using multiple channels as measurement portions in the measurement object disposing area and a mechanical scan method, switch can be made at higher speed, a number of kinds of objects to be measured can be measured in short time, and the throughput improves largely. Further, by using the waveguide and the switch, the optical analyzing device can be miniaturized and the cost can be reduced by mass production.

In an embodiment of the optical analyzing device according to the invention, the device further includes a test board positioned in the measurement object disposing area. The test board has a plurality of channels in which a specimen flows, receptors are fixed in each of the channels, and cross regions of the channels and the cores overlap overlapped portions of the cores and the switching elements when viewed from the test board. In such an embodiment, while passing a specimen to the channels in which the receptors are fixed, by observing changes in the light intensity along the channel and the changes with time, affinity and intermolecular interaction between the receptor and a ligand contained in the specimen and equilibrium constant can be measured.

Further, since the plurality of channels are provided in the embodiment, in the case where the same receptors are fixed on a channel unit basis and receptors which are different from each other are fixed in the channels, the affinity and intermolecular interaction between the specimen and each of the plurality of kinds of receptors and equilibrium constant can be measured in a lump, so that the throughput improves. In the case where the same receptors are fixed on a channel unit basis, by injecting different specimens to the channels, a plurality of specimens can be tested at once, and the throughput can be improved.

Further, in the embodiment, when a metallic thin film is formed in the channel, and receptors are fixed on the metallic thin film, measurement using the surface plasmon resonance can be performed, and problems such as detection error caused by a fluorescent molecule, and deactivation of biomolecules accompanying a fluorescent molecule as in the case of fluorescent detection can be avoided.

In another embodiment of the optical analyzing device according to the invention, a plurality of objects to be measured which are different from each other are arranged two-dimensionally in the measurement object disposing area, and each of the objects to be measured is disposed just above each of the overlapped portions of the cores and the switching elements. In such an embodiment, a plurality of objects to be measured which are arranged two-dimensionally can be measured at high speed, so that the throughput in the measuring work is very high.

In the another embodiment, when a metallic thin film is formed in the measurement object disposing area and an object to be measured is fixed on the metallic thin film, measurement using the surface plasmon resonance can be performed and problems such as detection error caused by a fluorescent molecule, and deactivation of biomolecules accompanying a fluorescent molecule as in the case of fluorescent detection can be avoided.

The switch in the further another embodiment of the optical analyzing device according to the invention is disposed so that the switching elements are in contact with the cores. In the state where the object to be measured is not detected, light guided in the cores is reflected by the switching elements. In the state where the object to be measured is detected, light guided in the cores passes through the switching elements. Therefore, by making the switch elements in the transmission state, light guided in the core which is led to the measurement object and modulated can be returned to the core. By making the switching element in the reflection state, light can be prevented from being influenced by the measurement object.

When a liquid crystal device utilizing refractive index anisotropy of a liquid crystal is used as the switch, switching speed can be increased and the cost of the switch can be reduced.

The present invention also provides a light detecting method for detecting a change in light by using the optical analyzing device according to the invention. The method includes the steps of: preliminarily determining a measurement portion in the measurement object disposing area while sandwiching a switching element between the measurement portion and any of the cores; switching only the switching element corresponding to the measurement portion in the measurement object disposing area to a detection state among the switching elements arranged along the core corresponding to the measurement portion in the measurement object disposing area; and detecting light emitted from the light source, guided in the core, and modulated in the measurement portion via the switching element in the detection state by the detector.

In the light detecting method of the invention, in the case of conducting measurement by the optical analyzing device of the invention, only a measurement result of a specific measurement portion among the plurality of measurement portions arranged along the core can be separated to be obtained.

The above-described components of the present invention can be arbitrary combined as much as possible.

BRIEF DESCRIPTION OF THE DRAWINGS

FIG. 1 shows a schematic perspective view showing a conventional analyzing apparatus.

FIG. 2 shows a schematic view showing another conventional analyzing apparatus.

FIG. 3 shows a perspective view of a further another conventional analyzing apparatus utilizing the surface plasmon resonance phenomenon.

FIG. 4 shows an exploded perspective view showing the structure of an optical analyzing device according to a first embodiment of the present invention.

FIG. 5 shows a plan view of the optical analyzing device of the first embodiment.

FIG. 6 shows a cross section taken along the length direction of cores in the optical analyzing device of the first embodiment.

FIG. 7 shows a cross section taken along the length direction of channels in the optical device of the first embodiment.

FIG. 8 shows a cross section showing a part of a switch.

FIG. 9 shows a cross section showing a part of a test board.

FIG. 10 shows a schematic view showing receptors fixed to a channel.

FIG. 11 shows a block diagram showing a processor as a component of the plasmon resonance analyzing apparatus of the invention.

FIG. 12 shows an explanatory diagram showing a state where a specimen is supplied to the channel in the test board.

FIG. 13 shows an explanatory diagram showing propagation of light in the core when a switching window is off.

FIG. 14 shows an explanatory diagram showing propagation of light in the core when the switching window is on and no ligand binds to the receptors.

FIG. 15 shows an explanatory diagram showing propagation of light in the core when the switching window is on and ligands bind to the receptors.

FIG. 16 shows a time chart showing an example of a control method of the switch.

FIG. 17 shows a time chart showing another control method of the switch.

FIG. 18 shows a diagram showing a result of measurement of changes in signal intensity along a channel.

FIG. 19 shows an explanatory diagram showing a state where ligands bound to the receptors unbind from receptors and re-bind to other receptors on the downstream side when affinity and interaction between specific ligands and receptors is small.

FIG. 20 shows a diagram showing an example of a signal intensity curve and measurement amounts extracted from the curve.

FIGS. 21(a) to 21(f) show explanatory diagrams showing an example of a waveguide manufacturing method.

FIGS. 22(a) to 22(c) show explanatory diagrams showing processes for manufacturing the waveguide, subsequent to the process of FIG. 21(f).

FIGS. 23A to 23F show explanatory diagrams showing an example of a test board manufacturing method.

FIGS. 24(a) to 24(e) show diagrams illustrating another method of manufacturing the waveguide.

FIGS. 25(a) to 25(f) show diagrams illustrating another method of manufacturing the waveguide.

FIG. 26 shows an exploded perspective view showing the structure of an optical analyzing device according to a second embodiment of the invention.

FIG. 27 shows a plan view of the optical analyzing device of the second embodiment.

FIG. 28 shows a schematic view showing the internal structure of a channel in a test board.

FIG. 29(a) shows a cross section taken along a channel arrangement direction of a switch and a test board, and FIG. 29(b) is a cross section taken along the length direction of the channel.

FIG. 30 shows a schematic diagram showing another arrangement of receptors in the channels in the test board.

FIG. 31 shows an exploded perspective view showing the structure of an optical analyzing device according to a third embodiment of the invention.

FIG. 32 shows a cross section showing a section taken along the core and channel arrangement direction in the optical analyzing device of the third embodiment.

FIG. 33 shows a cross section taken along the length direction of the core and the channel in the optical analyzing device of the third embodiment.

FIG. 34 shows an exploded perspective view showing the structure of an optical analyzing device according to a fourth embodiment of the invention.

FIG. 35 shows a plan view showing the positional relation between switching windows and cores in the optical analyzing device of the fourth embodiment.

FIG. 36 shows an exploded perspective view showing the structure of an optical analyzing device according to a fifth embodiment of the invention.

FIG. 37 shows a plan view illustrating the positional relations of the components in the optical analyzing device of the fifth embodiment.

FIG. 38 shows a perspective view showing another configuration of a test board.

FIG. 39 shows an exploded perspective view showing the structure of an optical analyzing device according to a sixth embodiment of the invention.

FIG. 40 shows an exploded perspective view illustrating a modification of the sixth embodiment.

FIG. 41 shows an exploded perspective view illustrating another modification of the sixth embodiment.

FIG. 42 shows an exploded perspective view showing the structure of an optical analyzing device according to a seventh embodiment of the invention.

FIG. 43 shows a partly cutaway cross section showing the structure of a switch used in the optical analyzing device of the seventh embodiment.

FIG. 44 shows a plan view showing the configuration of a light source, a waveguide, and a detector used for an optical analyzing device according to an eighth embodiment of the invention.

FIG. 45 shows a plan view showing the configuration of a light source, a waveguide, and a detector used for an optical analyzing device according to a ninth embodiment of the invention.

FIG. 46 shows an exploded perspective view of an optical branching part used in the ninth embodiment.

FIG. 47 shows a perspective view showing the configuration of a light source used for an optical analyzing device according to a tenth embodiment of the invention.

FIG. 48 shows an explanatory diagram showing the functions of a modulator used in the light source in the tenth embodiment.

DESCRIPTION OF REFERENCE NUMERALS 42 light source
43 waveguide
44 switch
45 test board
46 detector
47 light emitting elements
49 light receiving elements
51 cores
52 switching windows
58 black matrix region
60 channels
61 metallic thin film
62 receptors
63 receptors for filtering
65 processor
79 specimen
80 nonspecific ligand
81 specific ligand
112 injection port
113 exhaust port

BEST MODES FOR CARRYING OUT THE INVENTION

Embodiments of the present invention will be described in detail hereinbelow with reference to the drawings. The invention is not limited to the following embodiments but can be properly designed and changed according to applications, objects, and various circumstances.

First Embodiment

A surface plasmon resonance analyzing apparatus (a kind of an optical analyzing apparatus) of the present invention has, mainly, an optical analyzing device (41) and a processor (65) for analyzing kind, amount, characteristics, and the like of an object to be tested on the basis of an output of the optical analyzing device using the optical plasmon resonance phenomenon. Schematically, in a first embodiment of the invention, the optical analyzing device includes a light source (42), a waveguide (43), a switch (44), a test board (45), and a detector (43). The waveguide has a plurality of cores (51) and guides light from the light source in the cores while allowing the light to be repeatedly reflected. A plurality of light emitting elements (47) constructing a light emission part are disposed so as to face one end faces of the cores, and a plurality of light receiving elements (49) constructing the detector are disposed so as to face the other end faces of the cores. Therefore, light emitted from the light emitting elements enters the cores and is guided while repeating reflection in the cores. On the other hand, the light which goes out from the other ends of the cores is received by the light receiving elements of the light detector.

The switch overlaps the waveguide. The switch has switching windows (52 corresponding to switching elements in claims) which can be switched between a state where the object to be measured is detected and a state where the object to be measured is not detected. The plurality of switching windows are arranged along the length direction of the cores, for example, in a lattice shape as a whole. The switch is disposed so that the switching windows are in contact with the cores of the waveguide. In the state where the object to be measured is not detected, light guided in the cores is reflected by the switching windows. In the detection state, light guided in the cores passes through the switching windows. Such a switch is constructed by, for example, a liquid crystal device using refractive index anisotropy of liquid crystal and can select whether guided light is total reflected by or passes through the switching windows. In a position facing the waveguide on the switch, a measurement object disposing area is determined as a plane. Therefore, in a measurement part in which the switching window is in the non-detection state, light guided through the core is reflected by the switching window and does not act with the measurement object disposing area. On the other hand, in a measurement part in which the switching window is in the detection state, light guided through the core passes through the switching window and acts with the measurement object disposing area. The affected light returns again to the inside of the core and is finally detected by the light detector.

The test board has a plurality of channels in which a specimen flows. A metallic thin film is formed in each of the channels, and receptors are fixed on the metallic thin film. The test board is disposed so that the switching windows overlap the cross regions of the channels and the cores when viewed from the direction perpendicular to the test board. The test board is disposed in the measurement object disposing area on the switch. It is particularly preferable to dispose the test board so that the face of the metallic thin film on which the receptors are fixed matches the face of the measurement object disposing area. The specimen is passed from one end of the channel in the test board to the other end. When a specific ligand is included in the specimen, the specific ligand is captured by the receptor. Therefore, when a switching window in the switch is in the detection state, mutual action occurs between light and the object to be measured (the specific ligand that binds to the receptor) in the measurement part corresponding to the switching window and the light is modulated. By detecting the modulated light by the light detector, the kind, amount, characteristic, and the like of the object to be measured can be evaluated.

The optical analyzing device can employ various measuring methods in accordance with the kinds of receptors fixed to measurement parts (the same receptors or different receptors), switching timing of the on-state of the switching window (the switching windows are sequentially set to the on state, the switching windows along the channel are simultaneously turned on, or the like), and the like. For example, the same receptors are fixed in the same channel in the test board, and receptors in different channels may be different from each other. In this case, the affinity between the receptors and a specific ligand can be known in the direction along the channels, so that changes in the interaction along the channels can be known, and the degree of affinity and interaction between the specific ligand and the receptors can be evaluated. By fixing different receptors in a plurality of channels, reactions to a plurality of receptors can be evaluated at once.

The outline of the surface plasmon resonance analyzing apparatus of the first embodiment has been described above. In the following, the surface plasmon resonance analyzing apparatus will be described concretely.

FIGS. 4 to 7 show the optical analyzing device of the first embodiment as a component of a surface plasmon resonance analyzing apparatus of the invention using the surface plasmon resonance phenomenon. FIG. 4 is an exploded perspective view showing the structure of an optical analyzing device 41. FIG. 5 is a plan view of the optical analyzing device 41. FIG. 6 is a cross section taken along the length direction of cores in the optical analyzing device 41. FIG. 7 is a cross section taken along the length direction of channels in the optical analyzing device 41. The optical analyzing device 41 includes a light source 42, a waveguide 43, a switch 44, a test board 45, and a detector 46.

The light source 42 is constructed by a plurality of light emitting elements 47 such as light emitting diodes (LED) or lamps. The light source 42 may be also constructed by a plurality of independent light emitting elements 47 or an LED array may be used. The detector 46 is constructed by a plurality of light receiving elements 49 such as photodiodes or phototransistors. The detector 46 may be also constructed by a plurality of independent light receiving elements 49 or a light receiving element array may be used.

In the waveguide 43, a plurality of linear grooves are formed in a plate-shaped cladding 50 made of transparent resin or glass having high refractive index, and a transparent resin having refractive index higher than that of the cladding 50 is buried in the grooves, thereby forming a plurality of cores 51 in parallel with each other. The cores 51 have the same sectional shape and the same sectional area. The light source 42 and the detector 46 are disposed at both ends of the waveguide 43 so that the light emitting elements 47 and the light receiving elements 49 face the ends of the cores 51.

The switch 44 having a panel shape has a plurality of switching windows 52 arranged two-dimensionally or in a lattice, and can independently switch each of the switching windows 52 between an transmission state and a non-transmission state by an electric signal. As shown in FIG. 5, the switch 44 is stacked and integrated on the top face of the waveguide 43, and the switching windows 52 in each line are disposed just above each of the cores 51 in the waveguide 43. The switching windows 52 in a line arranged on an arbitrary core 51 are disposed at predetermined pitch.

As the switch 44, for example, a liquid crystal device can be used such as a liquid crystal shutter using refractive index anisotropy of liquid crystal, in which the refractive index of a liquid crystal layer changes between the on state and the off state, and the refractive index of the liquid crystal layer in the transmission state is almost equal to that of the core 51. FIG. 8 is a cross section showing a part of such a switch 44. In the switch 44, a liquid crystal layer 55 is sealed between an outside substrate 53 and an inside substrate 54, a transparent electrode 56 is provided on the inner face of the outside substrate 53, and transparent open electrodes 57 and black matrix regions 58 are formed on the inner face of the inside substrate 54. The aperture electrodes 57 are divided in a lattice shape by the black matrix regions 58, and the part of each of the aperture electrodes 57 serves as the switching window 52. A voltage applied across the aperture electrodes 57 and the transparent electrode 56 can be turned on/off by controlling switching elements such as TFTs provided in the black matrix regions 58. The black matrix region 58 is a region coated with black coating which does not transmit light. Not only the switching elements but also wiring patterns connected to the switching elements, and the like are also provided for the black matrix regions 58.

Preferably, the inside substrate 54, the aperture electrodes 57, the transparent electrode 56, and the outside substrate 53 constructing the switch 44 are made of materials each having refractive index almost equal to that of the core 52 of the waveguide 43. The refractive index of the liquid crystal layer 55 changes according to application of voltage. When no voltage is applied across the transparent electrode 56 and the aperture electrode 57, the refractive index of the liquid crystal layer 55 is lower than that of the core 51. When voltage is applied, the refractive index of the liquid crystal layer 55 becomes almost equal to that of the core 51 (and vice versa). Therefore, in the case where the switching window 52 is off and no voltage is applied across the transparent electrode 56 and the aperture electrode 57, when light propagating in the core 51 is incident on the switching window 52, the light is total-reflected by the switching window 52. However, in the case where the switching window 52 is on and voltage is applied across the transparent electrode 56 and the aperture electrode 57, when the light propagating in the core 51 is incident on the switching window 52, the light passes through the switching window 52.

FIG. 9 is a cross section showing a part of the test board 45. The test board 45 is obtained by forming a plurality of parallel groove-shaped channels 60 in the top face of a supporting plate 59 made of a glass thin plate, a transparent resin board, or the like, and a metallic thin film 61 such as an Au thin film is formed on the whole supporting plate 59 or in each of the channels 60. Alternatively, the channels 60 may be formed by etching the top face of the supporting plate 59 made of a glass thin film, or the channels 60 may be formed at the time of resin-molding the supporting plate 59 made of a transparent resin plate. The refractive index of the supporting plate 59 is desirably equal to that of the core 51. After the metallic thin film 61 is formed in the channels 60 in the supporting plate 59, by thinning the bottom of the supporting plate 59 by etching or polishing, the bottom face of the metallic thin film 61 may be exposed from the bottom face of the test board 45. On the metallic thin film 61 in the channels 60, receptors 62 of different kinds according to purposes and a receptor 63 for filtering are fixed. The test board 45 is detachably adhered onto the switch 44 via matching oil and is disposed so that the length direction of the channels 60 (although not limited but desirably) crosses the length direction of the core 51 when viewed from above. The top face of the channel 60 is desirably covered with a cover member 64 such as cover glass.

FIG. 10 is a schematic diagram showing the receptors 62 and 63 fixed in the channel 60. At the end on the upstream side in the channel 60 and in the region on the outside of the switching window 52 in the switch 44, the filtering receptors (nonspecific filtering protein) 63 that bind to ligands (hereinbelow, called nonspecific ligands) other than a particular ligand (hereinbelow, called specific ligand) are fixed. In the region facing the switching window 52 on the downstream side, the receptors (probe protein) 62 that bind to the specific ligand are fixed.

FIG. 11 is a block diagram showing the configuration of a processor 65 as a component of the surface plasmon resonance analyzing apparatus of the present invention. The processor 65 is miniaturized by a configuration using a microcomputer, an IC, and the like. The processor 65 includes a light source driving circuit 66, a switch control circuit 67, a receiving circuit 68, an analog/digital (hereinbelow, A/D) converter 69, an analyzer 70, a main controller 71, storing means 72, an input interface 73, and an output interface 74. The light source driving circuit 66 controls so that each of the light emitting elements 47 of the light source 42 emits light with predetermined power. The switch control circuit 67 controls so as to sequentially turn on the switching windows 52 in the switch 44 in predetermined order on the basis of an instruction from the main controller 71. The receiving circuit 68 receives an analog signal output from the light receiving elements 49 in the detector 46, and the A/D converter 69 converts the analog signal to a digital signal, and transmits the digital signal to the analyzer 70. The main controller 71 is constructed by a microcomputer or the like and controls the components in a centralized manner. The storing means 72 has a rewritable storing medium such as a hard disk and stores analysis software for analyzing the kind of a specimen, a signal intensity curve, and the like. To the input interface 73, input devices such as a keyboard 75 and a mouse 76 and a communication line are connected. Data for analysis entered from the input devices is transmitted from the input interface 73 to the main controller 71 and stored in the storing means 72. The analyzer 70 calculates the signal intensity curve of the specimen and the kind, amount, and the like of a specific ligand contained in the specimen on the basis of the data received from the detector 46 via the receiving circuit 68 and the A/D converter 69. To the output interface 74, output devices such as a monitor 77 and a printer 78 are connected. A measurement result such as the signal intensity curve calculated by the analyzer 70 is displayed on the screen of the monitor 77 via the output interface 74 or output from the printer 78.

Next, a process of actually analyzing a specimen will be described. First, the test board 45 in which a plurality of kinds of receptors 62 according to purposes and the filtering receptors 63 are fixed to the channels 60 is prepared, the matching oil is applied on the under face of the test board 45, and the test board 45 is positioned and adhered onto the switch 44. When the state is viewed from above, as shown in FIG. 5, the switching windows 52 in the switch 44 are positioned in cross regions of the cores 51 and the channels 60, and the cross regions and the switching windows 52 correspond to each other in a one-to-one corresponding manner. As shown in FIG. 6, light 48 emitted from the light emitting element 47 in the light source 42 enters a corresponding core 51 from the end face, propagates in the core 51 while repeating total reflection by the interface of the core 51, goes out from the other end of the core 51, and is received by the light emitting element 49 in the detector 46. In reality, there is also a case that the light propagating in the core 51 is total-reflected a plurality of times by one switching window 52 different from the light 48 shown in FIG. 6.

As shown in FIG. 12, when a specimen 79 is supplied from one end of the channel 60 in the test board 45, the specimen 79 flows in the channel 60 from the upstream side to the downstream side. Since the filtering receptors 63 are fixed on the upstream side in the channel 60, nonspecific ligands 80 (impurity) included in the specimen 79 supplied to the channel 60 bind to the filtering receptors 63 and are therefore eliminated from the specimen 79. To the fixed positions of the receptors 62, the specimen 79 from which most of the nonspecific ligands 80 are eliminated is supplied. When the specific ligand 81 reaches the receptor 62, the specific ligand 81 binds to the receptor 62.

In the case where a certain switching window 52 is off, as shown in FIG. 13, the light propagating in the core 51 is total-reflected by the interface of the core 51 in the switching window 52. Consequently, the signal propagating in the core 51 is not influenced by the state of the receptor 62, and the intensity of the light propagating in the core 51 does not change.

In contrast, when a certain switching window 52 is on, as shown in FIGS. 14 and 15, the light propagating in the core 51 passes through the switching window 52, is reflected by the metallic thin film 61 on the test board 45, the light reflected by the metallic thin film 61 is influenced by the surface plasmon resonance phenomenon, and the intensity of light detected by the detector 46 changes (hereinbelow, a change amount of the intensity of the light will be called signal intensity). However, in the case where the specific ligand 81 does not bind to the receptor 62 as shown in FIG. 14, a change in the signal intensity caused by the surface plasmon resonance phenomenon is small. In contrast, in the case where the specific ligand 81 binds to the receptor 62 as shown in FIG. 15, a change in the signal intensity caused by the surface plasmon resonance phenomenon is large. Particularly, the light 48 is reflected by the metallic thin film 61 a plurality of times via the switching window 52 which is on, so that the light 48 is amplified and a large change can be detected, or variations of the presence/absence in the binding in the area can be averaged, and stable detection can be performed.

Therefore, by sequentially turning on the switching windows 52 along the channel 60, changes in the signal intensity in the direction along the channel 60 can be detected in each of the channels 60. As typical patterns of sequentially turning on the switching windows 52 in the direction along the channel 60, there are a pattern as shown in FIG. 16 and a pattern as shown in FIG. 17.

"m" pieces of cores 51 arranged in parallel are numbered as M=1, 2, 3, . . . m and "n" pieces of channels 60 arranged so as to cross the m cores 51 are numbered as N=1, 2, 3, . . . n, and the switching window 52 positioned at the intersection between the core 51 of number M and the channel 60 of number N is expressed as (M, N) (refer to FIG. 5). In the method shown in FIG. 16, the switching windows 52 of M=1 to m arranged in the direction parallel with the channel 60 are simultaneously on/off controlled, and the line N of the switching windows 52 to be turned on are sequentially switched in the length direction of the core 51. According to the method, the signal intensity in the channels 60 is detected by the light receiving elements 49, and the measurement data can be transmitted as parallel data from the detector 46 to the receiving circuit 68.

In the method shown in FIG. 17, the switching windows 52 are turned on one by one, and the position where the switching window 52 is on is scanned. According to the method, the signal intensity in each of the channels 60 is detected by the light receiving elements 49 and the measurement data can be transmitted as serial data from the detector 46 to the receiving circuit 68.

FIG. 18 is a diagram showing a result of measurement of the change in the signal intensity along a channel 60 as described above. As shown in FIG. 12, the filtering receptors 63 are fixed near the position of injection of the specimen 79 and the nonspecific ligand 80 is captured here. Therefore, in FIG. 18, the peak of the signal intensity by the nonspecific ligand 80 appears near the position of injection of the specimen 79 (in reality, there are no switching windows 52 so that the signal intensity is not detected). Since the nonspecific ligand 80 is captured here, it hardly reaches the area where the receptors 62 are fixed, and the signal intensity by the nonspecific ligand 80 is hardly multiplexed on the signal intensity in the area of the receptor 62. Therefore, the signal intensity by the nonspecific ligand 80 and that by the specific ligand 81 can be separated from each other, erroneous detection of the specific ligand 81 can be reduced, and detection precision can be improved.

In the case where affinity and interaction between the specific ligand 81 and the receptor 62 is great, the specific ligand 81 which reaches to the area where the receptor 62 is fixed immediately binds to the receptor 62. Consequently, the peak by the specific ligand 81 appears on the side close to the injection position of the specimen 79 as a signal intensity curve indicated by bold solid line in FIG. 18. On the other hand, when affinity and interaction between the specific ligand 81 and the receptor 62 is small, the specific ligand 81 which reaches the area where the receptor 62 is fixed gradually binds to the receptor 62 while moving the area. Consequently, the peak by the specific ligand 81 moves to the far side from the injection position of the specimen 79 and becomes gentle (that is, the height of the peak is low, and the width of the peak is widened) like a signal intensity curve indicated by a thin broken line in FIG. 18.

In the case where affinity and interaction between the specific ligand 81 and the receptor 62 is small, as shown in FIG. 19, the specific ligand 81 once bound to the receptor 62 is easily separated from the receptor 62, and the separated specific ligand 81 flows in the channel 60 and re-binds to another receptor 62. Therefore, at the time of observing changes with time of the signal intensity curve along the channel 60, in the case where there affinity and interaction between the specific legend 81 and the receptor 62 is great, a change in the signal intensity curve is small even after lapse of time. In the case where affinity and interaction is small, with lapse of time, the peak position of the signal intensity curve moves to the downstream side. The smaller the affinity and interaction is, the higher the peak movement speed is. From the signal intensity curve in a state where the change stops, an equilibrium constant can be obtained.

Conventionally, by observing the rise speed of the signal intensity when the ligand binds to the receptor and the fall speed of the signal intensity when the ligand separates from the receptor, affinity and interaction between the ligand and the receptor can be measured. However, sufficient accuracy cannot be obtained.

As described above, the surface plasmon resonance analyzing apparatus of the first embodiment of the present invention is constructed by the optical analyzing device 41 and the processor 65. By the surface plasmon resonance analyzing apparatus, from the shape (static characteristic) of the signal intensity curve in the direction along the channel 60 and a change (dynamic characteristic) of the shape of the signal intensity curve, the affinity and the interaction between the specific ligand 81 and the receptor 62 can be evaluated. Particularly, as shown in FIG. 20, from peak height H, half width B, peak position L from the specimen injection position, peak movement speed V, and the like with respect to the specific ligand 81, affinity and interaction of the specific ligand 81 can be quantified. Therefore, the affinity and interaction can be measured from various physical quantities, and affinity between the ligand 81 and the receptor 62 or interaction between proteins can be analyzed with high accuracy.

In the surface plasmon resonance analyzing apparatus, the receptors 62 of different kinds are fixed in the plurality of channels 60. Consequently, by passing the same specimen 79 to the channels 60, affinity and interaction between a specific ligand 81 and the various receptors 62 can be simultaneously measured and compared. On the contrary, by fixing the same kind of receptors 62 in the channels 60 and passing the specimen 79 containing different specific ligands 81 to the channels 60, affinity and interaction of a plurality of kinds of specific ligands 81 can be measured at once.

In the first embodiment, it is also possible to fix the same receptors 62 in the channels 60 and pass different kinds of the specimens 79 to the channels 60.

Since the amount of the specific ligands 81 which bind to the receptors 62 in the channel 60 is proportional to the area below the signal intensity curve as shown in FIG. 20, by calculating the area, the amount of binding with the receptors 62 of the specific ligand 81 can be obtained. Since the receptors 62 in the channels 60 are different from each other, by comparing the intensities of signals from the receptors 62, the kind of the specific ligand 81 can be specified.

According to the invention, by making light propagate from the light source 42 to the detector 46 by using the optical waveguide (waveguide 43), the optical analyzing device 41 can be miniaturized. Further, by providing the switch 44 in which the switching windows 52 are arranged on the waveguide 43, affinity and interaction of genes or proteins can be measured. Therefore, the surface plasmon resonance analyzing apparatus can be miniaturized and low manufacture cost can be realized.

Next, a method of manufacturing the waveguide 43 and the test board 45 used in the optical analyzing device 41 will be described. FIG. 21 is an explanatory diagram showing an example of a method of manufacturing the waveguide 43. In the manufacturing method, first, a master 82 of cladding is manufactured by photolithography, plasma etching such as DRIE (Deep Reactive Ion Etching), laser processing, cutting, or the like (FIG. 21(a)). A nickel alloy or the like is deposited on the master 82 by the electroforming method to manufacture a stamper 83 (FIG. 21(b)), and the stamper 83 is peeled off from the master 82 (FIG. 21(c)). After that, an UV curable resin 85 is dropped onto a base glass 84 (FIG. 21(d)) and is pressed with the stamper 83 to spread the UV curable resin 85 between the base glass 84 and the stamper 83. Further, the UV curable resin 85 is irradiated with ultraviolet ray via the base glass 84 and is cured (FIG. 21(e)), and the stamper 83 is peeled off, thereby obtaining the cladding 50 (FIG. 21(f)).

After that, a core resin 86 such as an UV curable resin or the like is dropped on the cladding 50 (FIG. 22(a)) and is pressed with a press glass 87 so that the core resin 86 is filled in the grooves in the cladding 50. Further, the core resin 86 is cured by irradiation of ultraviolet rays or the like to form the cores 51 (FIG. 22(b)), and the press glass 87 is peeled off, thereby obtaining the waveguide 43 (FIG. 22(c)). The base glass 84 may remain on the under face of the cladding 50.

FIG. 23 is an explanatory diagram showing an example of the method of manufacturing the test board 45 which is manufactured by the stamper method in a manner similar to the waveguide 43. Specifically, a master 88 of the supporting plate 59 is manufactured by photolithography, plasma etching such as DRIE, laser processing, cutting, or the like (FIG. 23A). A nickel alloy or the like is deposited on the master 88 by the electroforming method to manufacture a stamper 89 (FIG. 23B). After that, an UV curable resin 91 is dropped onto a base glass 90 and is pressed with the stamper 89 to spread the UV curable resin 91 between the base glass 90 and the stamper 89. The UV curable resin 91 is irradiated with ultraviolet ray via the base glass 90 and is cured (FIG. 23C), and the stamper 89 is peeled off, thereby obtaining the supporting plate 59 having the channels 60 (FIG. 23D).

Subsequently, the metallic thin film 61 such as an Au thin film is formed on the inner face of the channels 60 in the supporting plate 59 or on the entire top face of the supporting plate 59 by vacuum evaporation or the like (FIG. 23E) and the receptors 62 and 63 are fixed on the metallic thin film 61 in each of the channels 60, thereby obtaining the test board 45 (FIG. 23F). Although the top of the channels 60 in the test board 45 may open, it is preferable that the top of the channel 60 be closed by overlaying the cover member 64 on the supporting plate 59 as shown in FIG. 23F.

FIG. 24 is a diagram illustrating another method of manufacturing the waveguide 43. In the method, first, a resist 93 is applied on a glass substrate 92 (FIG. 24(a)). An exposure mask 94 having openings in regions corresponding to the regions of the grooves in the cladding 50 is disposed so as to closely face the resist 93, and the resist 93 is exposed via openings 95 in the exposure mask 94 (FIG. 24(b)). After that, by developing the resist 93 on the glass substrate 92, the exposed parts are removed, thereby opening windows 96 in the resist 93 (FIG. 24(c)). An etchant is brought into contact with the glass substrate 92 via the windows 96 to partially etch the glass substrate 92, thereby forming a plurality of grooves 97 in the glass substrate 92 (FIG. 24(d)). By peeling off the resist 93 on the glass substrate 92, the cladding 50 is obtained (FIG. 24(e)). After the cladding 50 is manufactured, the cores 51 are filled in the grooves in the cladding 50 to manufacture the waveguide 43 by the same processes as the processes of FIGS. 22(a) to 22(c).

FIG. 25 is a diagram illustrating a method of manufacturing the test board 45 in a manner similar to the second manufacturing method of the waveguide 43. In the method, a resist 99 is applied on a glass substrate 98 (FIG. 25(a)). An exposure mask 100 having openings in regions corresponding to the regions of the channels 60 is disposed so as to closely face the resist 99, and the resist 99 is exposed via openings 101 in the exposure mask 100 (FIG. 25(b)). After that, by developing the resist 99 on the glass substrate 98, the exposed parts are removed, thereby opening windows 102 in the resist 99 (FIG. 25(c)). An etchant is brought into contact with the glass substrate 98 via the windows 102 to partially etch the glass substrate 98, thereby forming the plurality of channels 60 in the glass substrate 98 (FIG. 25(d)). By peeling off the resist 99 on the glass substrate 98, the supporting plate 59 having the channels 60 is obtained (FIG. 25(e)). After the supporting plate 59 is manufactured, the metallic thin film 61 is formed on the inner face of the channels 60 or on the entire top face of the supporting plate 59, thereby forming the test board 45 (FIG. 25(f)).

Second Embodiment

An optical analyzing device according to a second embodiment of the invention will now be described. Since the configuration of the processor 65 is similar to that in the first embodiment, the description will not be repeated.

The optical analyzing device of the second embodiment is characterized by the test board 45. Specifically, in the test board 45 used in the second embodiment, although a plurality of channels are disposed in parallel with each other in a part facing the switch 43, one ends of the channels are gathered to an injection port 112, and the other ends are gathered to an exhaust port 113. According to the second embodiment, injection and collection of specimens can be facilitated.

FIG. 26 is an exploded perspective view showing the structure of an optical analyzing device 111 in the second embodiment of the present invention, and FIG. 27 is a plan view of the structure. In the second embodiment, the structures of the light source 42, the waveguide 43, the switch 44, and the detector 46 are similar to those in the first embodiment. The plurality of channels 60 are formed in the test board 45, and the injection port 112 for supplying the specimen 79 into the channels 60 and the exhaust port 113 for exhausting the specimen 79 flowed through the channels 60 to the outside are opened in the top face of the test board 45. The injection port 112 is branched by a branch part 114 to the channels 60 and, on the opposite side of the channels 60, the channels 60 are merged by a merging part 115 to the exhaust port 113.

In a manner similar to the first embodiment, when viewed from above, the channels 60 and the cores 51 cross each other and the switching windows 52 in the switch 44 are positioned in the cross regions of the channels 60 and the cores 51.

FIG. 28 is a schematic diagram showing the internal structure of the channel 60. In the positions close to the injection port 112 in the channels 60, the filtering receptors 63 are fixed. On the downstream side of the receptors 63, different kinds of receptors 62 are fixed. Preferably, the densities of the receptors 62 in the channels 60 are equal to each other. The specimen 79 injected from the injection port 112 is branched in the branch part 114 and flows to the channels 60. The specimen 79 passes through the filtering receptors 63 and the various receptors 62, flows to the merging part 115, and is discharged to the outside or collected from the exhaust port 113. Therefore, according to the second embodiment, the specimen 79 can be supplied in a lump to the channels 60, the analyzing work is simplified, and the throughput improves.

The filtering receptors 63 may be disposed in a part before the branch to the plurality of channels 60 in the branch part 114 (in the part where the channel is still one). With the configuration, variations in removal of nonspecific ligands among the channels 60 can be suppressed.

FIGS. 29(a) and 29(b) are cross sections of the switch 44 and the test board 45. FIG. 29(a) shows a section along the arrangement direction of the channels 60, and FIG. 29(b) shows a section along the length direction of the channel 60. The test board 45 is mainly made of a cover member 116 and a supporting plate 117. The cover member 116 is made of a resin mold or glass (the material of the cover member 116 is not limited). In the under face of the cover member 116, the channels 60, the branch part 114, and the merging part 115 are recessed, and the injection port 112 and the exhaust port 113 are open at the end of the branch part 114 and the end of the merging part 115. The supporting plate 117 is formed in a plate shape or film shape by transparent resin or glass plate, and the metallic thin film 61 such as an Au thin film is formed on the top face of the supporting plate 17 by vacuum evaporation or the like. For the supporting plate 117, it is desirable to use a material having the same refractive index as that of the core 51. On the metallic thin film 61, the filtering receptors 63 and the various receptors 62 are preliminarily fixed in the positions corresponding to the channels 60 (refer to FIG. 28). The test board 45 is manufactured by attaching the supporting plate 117 to the under face of the cover member 116 so as to seal the under face of the cover member 116, and the receptors 63 and 62 are enclosed in the channels 60. It is also possible to omit the supporting plate 117 and close the under face of the cover member 116 only with the metallic thin film 61. Alternatively, it is also possible to form the metallic thin film 61 on the top face of the switch 44 and cover the under face of the cover member 116 with the switch 44.

The test board 45 manufactured in such a manner is placed on the switch 44 via the matching oil. At this time, the filtering receptor 63 is positioned deviated from any of the switching windows 52 in the switch 44, and the receptors 62 are disposed so as to extend from one end of the switching windows 52 in a line to the other end.

As obvious from the above-described configuration, the surface plasmon resonance analyzing apparatus of the second embodiment can also measure affinity and interaction of a specific ligand with high accuracy. In addition, it is easy to supply the specimen 79 in the second embodiment, so that the usability of the surface plasmon resonance analyzing apparatus further improves.

The receptor 62 fixed in the channel 60 does not always have to extend long as shown in FIG. 28. As shown in FIG. 30, the receptor 62 in one channel 60 may be divided into a plurality of receptors 62 and the receptors 62 may be disposed in positions corresponding to the switching windows 52. In the latter case, desirably, densities and areas of the receptors 62 (that is, the number of receptors 62) among the receptors 62 are the same (if the ratio of the numbers of receptors is known, they do not always have to be the same).

Third Embodiment

An optical analyzing device according to a third embodiment of the invention will now be described. Since the configuration of the processor 65 is similar to that in the first embodiment, the description will not be repeated.

The optical analyzing device of the third embodiment is characterized by the orientation of the test board 45. Specifically, the test board 45 used in the third embodiment is disposed on the switch 43 so that the channels in the test board 45 are parallel with the cores 51 in the waveguide 43 and the channels 60 are positioned above the cores. It will be concretely described below.

FIG. 31 is an exploded perspective view showing the structure of an optical analyzing device 121 in the third embodiment of the present invention. FIG. 32 is a cross section taken along the arrangement direction of the cores 51 and the channels 60 in the optical analyzing device 121, and FIG. 33 is a cross section taken along the length direction of the cores 51 and the channels 60 in the optical analyzing device 121. Although the test board 45 is disposed so that the channels 60 in the test board 45 and the cores 51 in the waveguide 43 cross each other in the first and second embodiments, in the optical analyzing device 121 of the third embodiment, the test board 45 is disposed so that the length direction of the channels 60 is parallel with the cores 51 in the waveguide 43.

Although the test board 45 described in the second embodiment is shown in the third embodiment, the test board 45 as used in the first embodiment may be alternatively used. The test board 45 is disposed so that the channels 60 are parallel with the cores 51. As shown in FIGS. 32 and 33, the channels 60 are positioned above the cores 51 via the switching windows 52. Also in the case where the channels 60 and the cores 51 are parallel with each other, by sequentially turning on the switching windows 52 along the channel 60, the state where specific ligands bind to the receptors 62 can be measured along the channel 60. Consequently, the signal intensity curve along the channel 60 can be obtained, the affinity and interaction of specific ligands, the kind and amount of the specific ligands, and the like can be measured.

Fourth Embodiment

An optical analyzing device according to a fourth embodiment of the invention will now be described. Since the configuration of the processor 65 is similar to that of the first embodiment, the description will not be repeated.

The optical analyzing device of the fourth embodiment is characterized by the structure of the switch 43. Specifically, in the switch 43 used in the fourth embodiment, a plurality of switching windows 52 each having a rectangular shape are disposed along the short-side direction. The switching windows 52 are disposed so as to cross the length direction of the channels 60, and the length in the long-side direction of the switching window 52 is longer than the length in the width direction of the entire channel 60. It will be concretely described below.

FIG. 34 is an exploded perspective view showing the structure of an optical analyzing device 131 in the fourth embodiment of the invention. In the optical analyzing device 131 according to the fourth embodiment, each of the switching windows 52 in the switch 44 has a rectangular shape. The length in the long-side direction is longer than the width of the plurality of cores 51 as a whole, and the plurality of switching windows 52 are arranged in the short-side direction. The direction of the channels 60 in the test board 45 may be parallel with or orthogonal to the cores 51.

In the optical analyzing device 131, the switching windows 52 are arranged at predetermined pitch only in one direction. By making (preferably, though not limited) the length direction of the core 51 cross the long-side direction of the switching window 52, the cross regions of the cores 51 and the switching windows 52 are arranged in matrix, so that signal intensity can be obtained from an arbitrary cross region. Therefore, by sequentially switching the switching windows 52 to be turned on, a signal intensity obtaining method as shown in FIG. 16 in the first embodiment can be realized. By sequentially switching the switching windows 52 to be turned on and sequentially taking signals from the light receiving elements 49, the signal intensities in the cross regions can be sequentially obtained in a time sharing manner, so that the signal intensity obtaining method as shown in FIG. 17 in the first embodiment can be realized. Therefore, the surface plasmon resonance analyzing apparatus can also analyze the interaction and affinity between proteins or the kind, amount, and the like of a specific ligand with high accuracy.

Fifth Embodiment

An optical analyzing device according to a fifth embodiment of the invention will now be described. The optical analyzing device of the fifth embodiment is characterized by the structure of a measurement object disposing area or the structure of the test board 45. Specifically, in the fifth embodiment, a plurality of receptors which are different from each other are arranged two-dimensionally in the measurement object disposing area, and each of the receptors is positioned just above each of the overlap parts of the cores and the switching windows 52. In the fifth embodiment, the test board does not have channels. In the embodiment, the metallic thin film 61 is formed on the surface of the test board 45 corresponding to the measurement object disposing area, a plurality of receptors which are different from each other are arranged two-dimensionally on the metallic thin film 61, and each of the receptors is positioned just above the overlap part of the core and the switching window 52. It will be concretely described below.

FIG. 36 is an exploded perspective view showing the structure of an optical analyzing device 141 in the fifth embodiment of the invention. FIG. 37 is a plan view illustrating the positional relations of the components of the optical analyzing device 141. The optical analyzing device 141 includes the light source 42, the waveguide 43, the switch 44, the test board 45, and the detector 46. The light source 42 is constructed by a plurality of light emitting elements 47 such as light emitting diodes (LED) or lamps. The light source 42 may be also constructed by a plurality of independent light emitting elements 47 or an LED array may be used. The detector 46 is constructed by a plurality of light receiving elements 49 such as photodiodes or phototransistors. The detector 46 may be also constructed by a plurality of independent light receiving elements 49, or a light receiving element array may be used.

In the waveguide 43, a plurality of linear grooves are formed in a plate-shaped cladding 50 made of transparent resin or glass having high refractive index, and a transparent resin having refractive index higher than that of the cladding 50 is buried in the grooves, thereby forming a plurality of cores 51 in parallel with each other. The cores 51 have the same sectional shape and the same sectional area. The light source 42 and the detector 46 are disposed at both ends of the waveguide 43 so that the light emitting elements 47 and the light receiving elements 49 face the ends of the cores 51.

The switch 44 having a panel shape has a plurality of switching windows 52 arranged two-dimensionally or in a lattice, and can independently switch each of the switching windows 52 between a transmission state and a non-transmission state by an electric signal. The switch 44 is stacked and integrated on the top face of the waveguide 43, and the switching windows 52 in lines parallel with the cores 51 are disposed just above the cores 52 in the waveguide 43. The switching windows 52 in a line arranged over an arbitrary core 51 are disposed at predetermined pitch. The switch 44 has the same structure as that of the switch 44 described in the first embodiment (refer to FIG. 8).

The test board 45 is obtained by forming the metallic thin film 61 such as an Au thin film on almost the entire surface of a supporting plate 142 made of a glass plate or a transparent resin film. On the metallic thin film 61, the receptors 62 are fixed at equal intervals in the vertical and horizontal directions. All the receptors 62 fixed on the test board 45 are different kinds of receptors. The test board 45 is detachably bonded on the switch 44 via matching oil.

The receptors 62 fixed on the test board 45 may be divided one by one. FIG. 38 shows the test board 45 in which the receptors 62 are partitioned one by one by a frame 143. The test board 45 is obtained by forming the metallic thin film 61 on the supporting plate 142, applying a photosensitive resin on the metallic thin film 61, etching the photosensitive resin into a lattice shape by photolithography, and providing the frame 143 having a plurality of rectangular spaces. By partitioning the receptors 62 with the frame 143, when the specimen 79 is supplied to the receptors 62, the specimens 79 supplied to the receptors 62 do not mix each other, so that test precision can be improved.

In a manner similar to the first embodiment, the surface plasmon resonance analyzing apparatus has the processor 65 as shown in FIG. 11. By controlling the cores 51 in the switch 44 as shown in FIG. 16 or 17, the degree of affinity of each of the receptors 62 and a specific ligand and signal intensity can be detected (refer to FIGS. 13 to 15).

In a state where the switch 44 is placed on the waveguide 43 and the test board 45 is placed on the switch 44, the switching windows 52 in the switch 44 are arranged on the cores 51 as shown in FIG. 37, and the receptors 62 in the test board 45 are positioned on the switching windows 52. Therefore, the specimen 79 containing the specific ligand 81 is supplied to each of different kinds of the receptors 62. By sequentially switching the on state of the switching windows 52 and detecting the signal intensity by the light receiving elements 49, the reactions with the receptors 62 can be tested in a lump, and the kind and the amount of the specific ligand can be measured. For example, when the number of the cores 51 is 100 and the number of the switching windows 52 is 100×100, the reactions between the specimen 79 and 10,000 kinds of receptors 62 can be analyzed at once by the surface plasmon resonance analyzing apparatus. Thus, throughput can be largely improved.

Sixth Embodiment

An optical analyzing device according to a sixth embodiment of the invention will now be described. Since the configuration of the processor 65 is similar to that of the first embodiment, the description will not be repeated. The optical analyzing device of the sixth embodiment is characterized by the test board 45. Specifically, the optical analyzing device is characterized by the point that the test board 45 itself used in the sixth embodiment is the same as the test board 45 of the second embodiment but the kinds of the receptors 62 arranged in one channel 60 are all different from each other. It will be concretely described below.

FIG. 39 is an exploded perspective view showing the structure of an optical analyzing device 151 in the sixth conventional art. In the sixth embodiment, the test board 45 having the same structure as that shown in FIG. 30 of the second embodiment is used. Although the receptors 62 in one channel 60 are all of the same kind in FIG. 30, the kinds of the receptors 62 in the sixth embodiment are all different from each other, and the receptors 62 in the same channel 60 are also all different from each other.

In the surface plasmon resonance analyzing apparatus, the receptors 62 of different kinds are arranged in the channels 60, so that supply of the specimen 79 to the receptors 62 is facilitated, and throughput further improves.

The test board 45 having the channels 60 may be disposed so that, like the optical analyzing device 161 shown in FIG. 40, the direction of the channels 60 is parallel with the cores 51 in the waveguide 43. The switch 44 is not limited to the configuration in which the switching windows 52 are arranged in a lattice shape but may have a configuration in which the switching windows 52 each having a rectangular shape are arranged in the length direction of the core 51 like in the optical analyzing device 171 shown in FIG. 41.

Seventh Embodiment

An optical analyzing device according to a seventh embodiment of the present invention will now be described. The optical analyzing device of the seventh embodiment is characterized by the structure of the measurement object disposing area. Specifically, in the fifth embodiment, a plurality of receptors different from each other are arranged two-dimensionally in the measurement object disposing area, and the receptors are positioned just above the overlap parts of the cores and the switching windows 52. The switch 44 and the test board 45 are formed integrally and the test board 45 does not have channels. In the seventh embodiment, the top face of the switch 44 is the measurement object disposing area, the metallic thin film 61 is formed on the top face of the switch 44, a plurality of receptors which are different from each other are arranged two-dimensionally on the metallic thin film 61, and the receptors are positioned just above the overlap parts of the cores and the switching windows 52. It will be concretely described below.

FIG. 42 is an exploded perspective view showing the structure of an optical analyzing device 181 in the seventh embodiment. FIG. 43 is a partly cutaway cross section showing the structure of the switch 44 used in the optical analyzing device 181. In the seventh embodiment, the metallic thin film 61 such as an Au thin film is formed directly on the top face of the switch 44 (that is, the top face of the outside substrate 53) in which a plurality of windows 52 are arranged, and different kinds of the receptors 62 are fixed on the metallic thin film 61. It is also possible to omit the outside substrate 53 and the transparent electrode 56 of the switch 44, directly seal the top face of the liquid crystal layer 55 with the metallic thin film 61, and apply a voltage to the liquid crystal layer 55 by the metallic thin film 61 and the aperture electrode 57.

In the embodiment, the switch 44 can be configured such that the switch 44 and the test board 45 are integrated, therefore the structure can be simplified and the manufacturing cost of the whole can be decreased. Since the receptors 62 are fixed directly to the switch 44, the positioning of the receptors 62 and the switching windows 52 is facilitated.

Eighth Embodiment

An optical analyzing device according to an eighth embodiment of the present invention will now be described. The optical analyzing device of the eighth embodiment is characterized by the structure of the light source 42 and the detector 46. Specifically, the eighth embodiment is characterized in that a condenser lens 191 is disposed between each of the light emitting elements 47 in the light source 42 and an end face of each of the cores 51, and a condenser lens 192 is disposed between each of the light receiving elements 49 of the detector 46 and the other end face of the core 51. It will be concretely described below.

FIG. 44 is a plan view showing the configuration of the light source 42, the waveguide 43, and the detector 46 used for the optical analyzing device in the eighth embodiment of the invention. In the surface plasmon resonance analyzing apparatus according to the eighth embodiment, the condenser lens 191 is disposed between each of the light emitting elements 47 of the light source 42 and an end face of a core 51, and the condenser lens 192 is disposed between each of the light receiving elements 49 of the detector 46 and the other end face of the core 51.

By providing the condenser lenses 191 for the light source 42, light emitted from the light emitting elements 47 can be condensed and the condensed light can enter the cores 51, so that efficiency of light utilization improves. By providing the condenser lenses 192 for the detector 46, the light emitted from the cores 51 can be condensed and the condensed light can be incident on the light emitting elements 49, so that signal intensity detection precision can be improved.

Ninth Embodiment

An optical analyzing device according to a ninth embodiment of the present invention will now be described. The optical analyzing device of the ninth embodiment is characterized by the structure of the light source 42 in which the required number of light emitting elements 47 is reduced. It will be concretely described below.

FIG. 45 is a plan view showing the configuration of the light source 42, the waveguide 43, and the detector 46 used for the optical analyzing device according to the ninth embodiment of the invention. In the ninth embodiment, optical branching parts 201 are inserted between the light source 42 and the waveguide 43. As shown in FIG. 46, the optical branching part 201 is constructed by an optical waveguide. A core 203 having a plurality of branches is buried in a lower cladding layer 202, and the top face of the core 203 is covered with an upper cladding layer 204. The refractive index of the core 203 is higher than that of the lower and upper cladding layers 202 and 204. The light emitting element 47 faces an end face on the side where the core 203 is not branched, and end faces of the cores 51 in the waveguide 43 face the end faces on the branched side of the cores 203.

According to the ninth embodiment, light emitted from one light emitting element 47 is branched in the optical branching part 201 and the branched light can be sent to the cores 51 in the waveguide 43, so that the number of light emitting elements 47 in the light source 42 can be decreased, power consumption in the light source 42 can be suppressed and, further, the manufacture cost can be reduced.

Although two optical branching parts 201 are used in FIG. 45, by increasing the degree of branching of the optical branching part 201, the device can be constructed by the light source 42 including one light emitting element 47 and one optical branching part 201. The optical branching part 201 can be also constructed integrally with the waveguide 43. On the light reception side as well, the number of light receiving elements 49 may be decreased by using an optical coupler having a structure similar to that of the optical branching part.

Tenth Embodiment

An optical analyzing device according to a tenth embodiment of the present invention will now be described. The optical analyzing device of the tenth embodiment is characterized by the structure of the light source 42 in which the required number of light emitting elements 47 is decreased. It will be concretely described below.

FIG. 47 is a perspective view showing the configuration of the light source 42 used for the optical analyzing device according to the tenth embodiment of the invention. The light source 42 includes one light emitting element 47, a polarization element 211 such as a polarization filter, and a modulator 212. As shown in FIG. 48, the modulator 212 has, on its front face, a light guide 213 made of a transparent resin or glass having high refractive index, a plurality of liquid crystal shutters 214 are arranged on the rear face of the light guide 213, and a reflection surface 215 is provided in the rear face of each of the liquid crystal shutters 214. In the modulator 212, the liquid crystal shutters 214 are disposed so as to face the cores 51, and the light emitting element 47 faces a side face of the light guide 213 via the polarization element 211.

When the light emitting element 47 emits light, the light emitted from the light emitting element 47 passes through the polarization element 211 and becomes linearly polarized light. The linearly polarized light enters the light guide 213 of the modulator 212. The light that enters the light guide 213 is guided in the light guide 213 while repeating total reflection. The liquid crystal shutter 214 reflects light in the off state and transmits light in the on state. Consequently, the light guided in the light guide 213 passes while being reflected by the liquid crystal shutters 214 in the off state. However, when the light reaches the liquid crystal shutter 214 in the on state, it enters the liquid crystal shutter 214 and is reflected by the reflection surface 215. The reflection light passes through the liquid crystal shutter 214 and the light guide 213 and goes out from the front face of the modulator 212. The light that goes out from the front face of the modulator 212 enters the corresponding core 51 in the waveguide 43 and propagates in the core 51. Therefore, by sequentially switching the liquid crystal shutters 214 to the on state, light for measurement can sequentially enter the cores 51 from the modulator 212.

By using such a light source, power consumption of the light source 42 is suppressed and the light source 42 can be miniaturized.

Although not shown, it is also possible to construct the light source by the light emitting elements and micro mirrors and guide light emitted from the light emitting element 47 to a core by controlling the angle of the micro mirrors.

Others

The optical analyzing devices and the optical analyzing apparatuses each including the optical device and the processor according to the invention can be used as an optical analyzing apparatus other than a surface plasmon resonance analyzing apparatus. By using any of the optical analyzing apparatuses to measure a light signal from a sample, the presence/absence, amount, intermolecular interaction, affinity, equilibrium constant, and the like of a target substance (gene, DNA, or the like) in the sample can be evaluated. For example, in the case of constructing the optical analyzing apparatus as a fluorescence detection type optical analyzing apparatus, when sample DNA marked with a fluorescent dye or the like is passed to a channel in a test board in which probe DNA is adhered at high density, DNA complementary to each other binds. Therefore, by detecting a signal in each of the positions on the test board, the presence or absence or the degree of interaction between each of the probe DNA and the sample DNA can be evaluated. By using the method, determination of gene arrangement, detection of the presence/absence of a specific gene, measurement of an expression level of a specific gene, and the like can be performed.

Other uses of the analyzing method according to the invention include analysis of SNP (single nucleotide polymorphism), recognition of a pathway or state of metabolism, absorption, and excretion of a substance given to a laboratory mouse, measurement of ion concentration in a cell, identification or functional analysis of a protein, and the like. The analyzing method according to the invention can be also used for a medical checkup for checking health conditions of a person, a test for personal security, and the like.

The invention claimed is:

1. An optical analyzing device comprising:
    a light source;
    a waveguide having a plurality of cores and guiding light from the light source in the cores while allowing the light to repeat reflection;
    a photodetector for receiving the light guided through the cores in the waveguide;
    a switch having a plurality of switching elements each of which can be switched between a state where an object to be measured is detected and a state where the object to be measured is not detected, and overlapping the waveguide so that the plurality of switching elements are arranged in the length direction of the cores; and
    a measurement object disposing area determined as a face in a position facing the waveguide via the switch.

2. The optical analyzing device according to claim 1, further comprising a test board positioned in the measurement object disposing area,
    wherein the test board has a plurality of channels in which a specimen flows,
    receptors are fixed in each of the channels, and
    cross regions of the channels and the cores overlap overlapped portions of the cores and the switching elements when viewed from the test board.

3. The optical analyzing device according to claim 2, wherein the same receptors are fixed in each channel, and receptors which are different from each other are fixed in the channels.

4. The optical analyzing device according to claim 2, wherein a metallic thin film is formed in the channel, and receptors are fixed on the metallic thin film.

5. A surface plasmon resonance analyzing apparatus comprising:
    an optical analyzing device according to claim 4; and
    means for analyzing kind, amount, characteristic, and the like of an object to be tested on the basis of an output of the optical analyzing device by using surface plasmon resonance phenomenon.

6. The optical analyzing device according to claim 1, wherein a plurality of objects to be measured which are different from each other are arranged two-dimensionally in the measurement object disposing area, and
    each of the objects to be measured is disposed just above each of the overlapped portions of the cores and the switching elements.

7. The optical analyzing device according to claim 6, wherein a metallic thin film is formed in the measurement object disposing area, and an object to be measured is fixed on the metallic thin film.

8. A surface plasmon resonance analyzing apparatus comprising:
    an optical analyzing device according to claim 7; and
    means for analyzing kind, amount, characteristic, and the like of an object to be tested on the basis of an output of the optical analyzing device by using surface plasmon resonance phenomenon.

9. The optical analyzing device according to claim 1, wherein the switch is disposed so that the switching elements are in contact with the cores, in the state where the object to be measured is not detected, light guided in the cores is reflected by the switching elements and, in the state where the object to be measured is detected, light guided in the cores passes through the switching elements.

10. The optical analyzing device according to claim 9, wherein the switch is constructed by a liquid crystal device utilizing refractive index anisotropy of a liquid crystal, and whether guided light is total-reflected or passed can be selected with respect to each of the switching elements.

11. An optical analyzing apparatus comprising:
    an optical analyzing device according to claim 1; and
    means for analyzing kind, amount, characteristic, and the like of an object to be tested on the basis of an output of the optical analyzing device.

12. A biochip using the optical analyzing device according to claim 1.

13. A light detecting method for detecting a change in light by using an optical analyzing device according to claim 1, comprising the steps of:

preliminarily determining a measurement portion in the measurement object disposing area while sandwiching a switching element between the measurement portion and any of the cores;

switching only the switching element corresponding to the measurement portion in the measurement object disposing area to a detection state among the switching elements arranged along the core corresponding to the measurement portion in the measurement object disposing area; and detecting light emitted from the light source, guided in the core, and modulated in the measurement portion via the switching element in the detection state by the detector.

14. A method of analyzing an object to be measured, for evaluating kind, amount, or characteristic of an object to be measured by using the light detecting method according to claim 13.

* * * * *